United States Patent
George et al.

(10) Patent No.: US 11,638,552 B2
(45) Date of Patent: May 2, 2023

(54) PROSTATE GLOVE, FINGERTIP OPTICAL ENCODER, CONNECTOR SYSTEM, AND RELATED METHODS

(71) Applicant: MEDICAMETRIX, INC., Wayland, MA (US)

(72) Inventors: Joseph James George, Amherst, NH (US); Christopher LaFarge, Wayland, MA (US)

(73) Assignee: MedicaMetrix, Inc., Lowell, MA (US)

( * ) Notice: Subject to any disclaimer, the term of this patent is extended or adjusted under 35 U.S.C. 154(b) by 842 days.

(21) Appl. No.: 15/386,894

(22) Filed: Dec. 21, 2016

(65) Prior Publication Data
US 2017/0172486 A1 Jun. 22, 2017

Related U.S. Application Data

(60) Provisional application No. 62/378,809, filed on Aug. 24, 2016, provisional application No. 62/366,738, (Continued)

(51) Int. Cl.
*A61B 5/107* (2006.01)
*A61B 5/00* (2006.01)
(Continued)

(52) U.S. Cl.
CPC .......... *A61B 5/4381* (2013.01); *A61B 5/1076* (2013.01); *A61B 5/6806* (2013.01); (Continued)

(58) Field of Classification Search
CPC ..... A61B 5/107; A61B 5/0084; A61B 5/0086; A61B 5/1076; A61B 6/00; A61B 5/1079; (Continued)

(56) References Cited

U.S. PATENT DOCUMENTS

| 3,904,269 A | 9/1975 | Lebduska et al. |
| 4,817,601 A | 4/1989 | Roth et al. |
| (Continued) |

FOREIGN PATENT DOCUMENTS

| WO | 00/13591 A1 | 3/2000 |
| WO | 2005/021049 A2 | 3/2005 |
| (Continued) |

OTHER PUBLICATIONS

[No Author Listed] Fiber Optics Light Glove. Designboom. Sep. 28, 2007, 1 page, Retrieved from <http://www.designboom.com/project/fiber-optics-light-glove/>.
(Continued)

*Primary Examiner* — Jon Eric C Morales
(74) *Attorney, Agent, or Firm* — Brown Rudnick LLP; Matthew P. York

(57) ABSTRACT

Systems and methods are provided herein that generally involve measuring a prostate or other object. In some embodiments, a finger clip having a roller ring or wheel rotatably mounted thereto is disposed within an inflatable membrane. The roller ring can include a measurement pattern positioned opposite to optical fibers configured to receive light reflected from the measurement pattern. A user can put on the finger clip, position the membrane in proximity to a rectal wall overlying a prostate, and inflate the membrane. As the user slides their finger across the inside of the membrane, which is pressed against the rectal wall, the roller ring can rotate with respect to the fibers such that the fibers move relative to the measurement pattern. A controller can sense light reflected through the fibers from the reference pattern and calculate or estimate various attributes of the prostate based on the reflected light.

30 Claims, 35 Drawing Sheets

Related U.S. Application Data filed on Jul. 26, 2016, provisional application No. 62/271,009, filed on Dec. 22, 2015.

(51) Int. Cl.
 *A61B 1/07* (2006.01)
 *G02B 6/38* (2006.01)

(52) U.S. Cl.
 CPC .......... *A61B 5/6826* (2013.01); *G02B 6/3885* (2013.01); *G02B 6/3893* (2013.01); *A61B 5/1073* (2013.01); *A61B 5/1079* (2013.01); *A61B 5/6873* (2013.01); *A61B 5/6885* (2013.01); *A61B 5/7246* (2013.01); *G02B 6/3821* (2013.01)

(58) Field of Classification Search
 CPC ................ A61B 5/4381; A61B 5/6806; A61B 2562/225; A61B 2562/227; B33Y 80/00; B33Y 70/00
 USPC ........................................ 600/587, 478, 477
 See application file for complete search history.

(56) References Cited

U.S. PATENT DOCUMENTS

| | | | |
|---|---|---|---|
| 4,995,119 A | 2/1991 | Codkind | |
| 5,059,477 A | 10/1991 | Henriksen | |
| 5,097,252 A | 3/1992 | Harvill et al. | |
| 5,196,247 A | 3/1993 | Wu et al. | |
| 5,265,181 A | 11/1993 | Chang | |
| 5,279,309 A | 1/1994 | Taylor et al. | |
| 5,304,171 A | 4/1994 | Gregory et al. | |
| 5,423,090 A | 6/1995 | Gimbel | |
| 5,423,332 A | 6/1995 | Zirps et al. | |
| 5,582,620 A | 12/1996 | Hirsch | |
| 5,867,831 A | 2/1999 | Husain | |
| 5,922,018 A | 7/1999 | Sarvazyan | |
| 5,965,276 A | 10/1999 | Shlenker et al. | |
| 6,142,959 A | 11/2000 | Sarvazyan et al. | |
| 6,360,116 B1 | 3/2002 | Jackson, Jr. et al. | |
| 6,428,531 B1 | 8/2002 | Visuri et al. | |
| 6,709,142 B2 | 3/2004 | Gyori | |
| 6,743,165 B2 | 6/2004 | Mosel et al. | |
| 6,829,421 B2 | 12/2004 | Forbes et al. | |
| 7,254,842 B2 | 8/2007 | Becerra et al. | |
| 7,309,319 B2 | 12/2007 | Kellett et al. | |
| 7,354,202 B1 | 4/2008 | Luger | |
| 7,359,742 B2 | 4/2008 | Maser et al. | |
| 7,582,056 B2 | 9/2009 | Noguchi et al. | |
| 7,662,113 B2 | 2/2010 | Pearl et al. | |
| 8,092,372 B2 | 1/2012 | Machida | |
| 8,104,097 B2 | 1/2012 | Hamann | |
| 8,694,079 B1 | 4/2014 | LaFarge | |
| 8,838,214 B2 | 9/2014 | LaFarge | |
| 9,339,172 B2 | 5/2016 | Slenker et al. | |
| 9,387,305 B2 | 7/2016 | Courtney et al. | |
| 9,402,547 B2 | 8/2016 | LaFarge | |
| 9,402,564 B2 | 8/2016 | LaFarge | |
| 9,538,952 B2 | 1/2017 | LaFarge | |
| 2003/0009087 A1 | 1/2003 | Keirsbilck | |
| 2003/0210259 A1 | 11/2003 | Liu et al. | |
| 2004/0017981 A1 | 1/2004 | Jovanovich et al. | |
| 2004/0213445 A1 | 10/2004 | Lee et al. | |
| 2005/0021013 A1 | 1/2005 | Visuri et al. | |
| 2006/0026737 A1 | 2/2006 | Chen | |
| 2006/0052663 A1 | 3/2006 | Koitabashi | |
| 2006/0069721 A1 | 3/2006 | Dowling | |
| 2006/0106294 A1 | 5/2006 | Maser et al. | |
| 2006/0116552 A1 | 6/2006 | Noguchi et al. | |
| 2006/0122538 A1 | 6/2006 | Kellett et al. | |
| 2006/0129070 A1 | 6/2006 | Pearl et al. | |
| 2007/0244363 A1 | 10/2007 | Sano et al. | |
| 2007/0293792 A1 | 12/2007 | Sliwa et al. | |
| 2008/0167527 A1 | 7/2008 | Slenker et al. | |
| 2008/0200926 A1 | 8/2008 | Verard et al. | |
| 2008/0306387 A1 | 12/2008 | Schutz et al. | |
| 2009/0023996 A1 | 1/2009 | Fujikura | |
| 2009/0068443 A1 | 3/2009 | Curtet et al. | |
| 2009/0069721 A1 | 3/2009 | Kellett et al. | |
| 2009/0209813 A1 | 8/2009 | Lubowski et al. | |
| 2010/0256461 A1 | 10/2010 | Mohamedali et al. | |
| 2010/0262020 A1 | 10/2010 | Backman et al. | |
| 2010/0305400 A1 | 12/2010 | Onoda et al. | |
| 2011/0009699 A1 | 1/2011 | Slenker et al. | |
| 2011/0172563 A1 | 7/2011 | Kellett et al. | |
| 2011/0302694 A1 | 12/2011 | Wang et al. | |
| 2013/0023770 A1 | 1/2013 | Courtney et al. | |
| 2013/0031696 A1 | 2/2013 | Jundt | |
| 2014/0121529 A1 | 5/2014 | LaFarge | |
| 2014/0121533 A1 | 5/2014 | LaFarge | |
| 2014/0121534 A1 | 5/2014 | LaFarge | |
| 2014/0121535 A1 | 5/2014 | LaFarge | |
| 2014/0121536 A1 | 5/2014 | LaFarge | |
| 2014/0121562 A1 | 5/2014 | LaFarge | |
| 2014/0121563 A1* | 5/2014 | LaFarge ............... | A61B 5/6806 600/587 |
| 2017/0007203 A1 | 1/2017 | Courtney et al. | |

FOREIGN PATENT DOCUMENTS

| | | |
|---|---|---|
| WO | 2005/051191 A1 | 6/2005 |
| WO | 2009/067573 A2 | 5/2009 |

OTHER PUBLICATIONS

[No Author Listed] Industrial Fiber Optics, SK-20; 0.5mm Optical Fiber High Performance Plastic Optical Fiber, Jul. 10, 2010. https://web.archive.org/web/20100710185724/http://i-fiberoptics.com/fiber-detail.php?id=122 (1 page).

[No Author Listed] ProstaMetric, www.medicametrix.com, MedicaMetrix, Inc., published on Jun. 28, 2016, retrieved on Apr. 17, 2017 from <http://web.archive.org/web/20160628212041/http://www.medicametrix.com/?page_id=1918>, 2 pages.

Eri, L.M., et al., Accuracy and repeatability of prostate vol. measurements by transrectal ultrasound. Prostate Cancer and Prostatic Diseases, 2002;5:273-8.

Extended European Search Report for Application No. 13852114.1, dated May 11, 2016 (6 pages).

International Application No. PCT/US04/039664—International Search Report, Written Opinion, and IPRP.

International Application No. PCT/US08/084112—International Search Report, Written Opinion, and IPRP.

International Search Report and Written Opinion for Application No. PCT/US2013/063986 dated Apr. 11, 2014 (19 Pages).

Invitation to Pay Additional Fees for Application No. PCT/US2016/068051, dated Mar. 7, 2017 (2 pages).

International Search Report and Written Opinion for Application No. PCT/US2016\068051, dated May 4, 2017 (11 Pages).

U.S. Appl. No. 13/663,875, filed Oct. 30, 2012, Double Membrane Prostate Glove.

U.S. Appl. No. 13/663,877, filed Oct. 30, 2012, Prostate Glove With Measurement Grid.

U.S. Appl. No. 13/663,879, filed Oct. 30, 2012, Grid for Measurement Prostate Volume.

U.S. Appl. No. 13/663,881, filed Oct. 30, 2012, Prostate Glove With Receiver Fibers.

U.S. Appl. No. 13/663,883, filed Oct. 30, 2012, Finger Clip for Prostate Glove.

U.S. Appl. No. 13/663,888, filed Oct. 30, 2012, Connector for Use With a Prostate Measurement System.

U.S. Appl. No. 13/663,890, filed Oct. 30, 2012, Controller for Measurement Prostate Volume

* cited by examiner

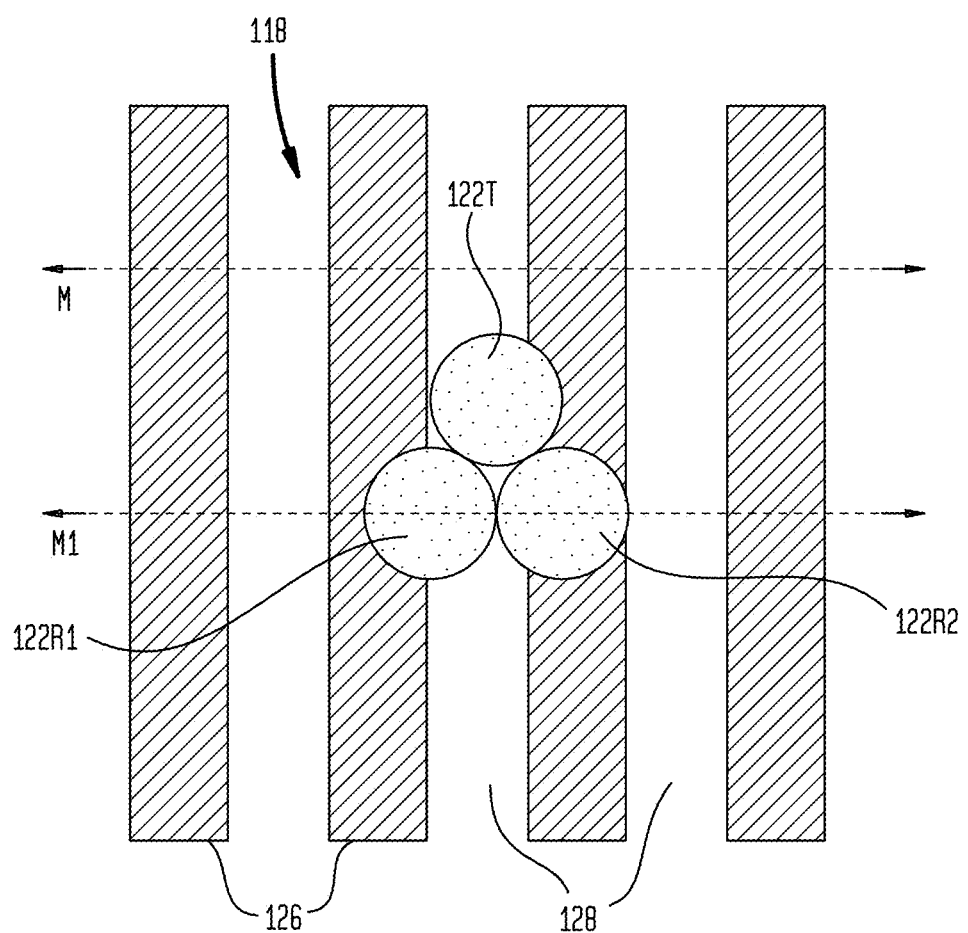

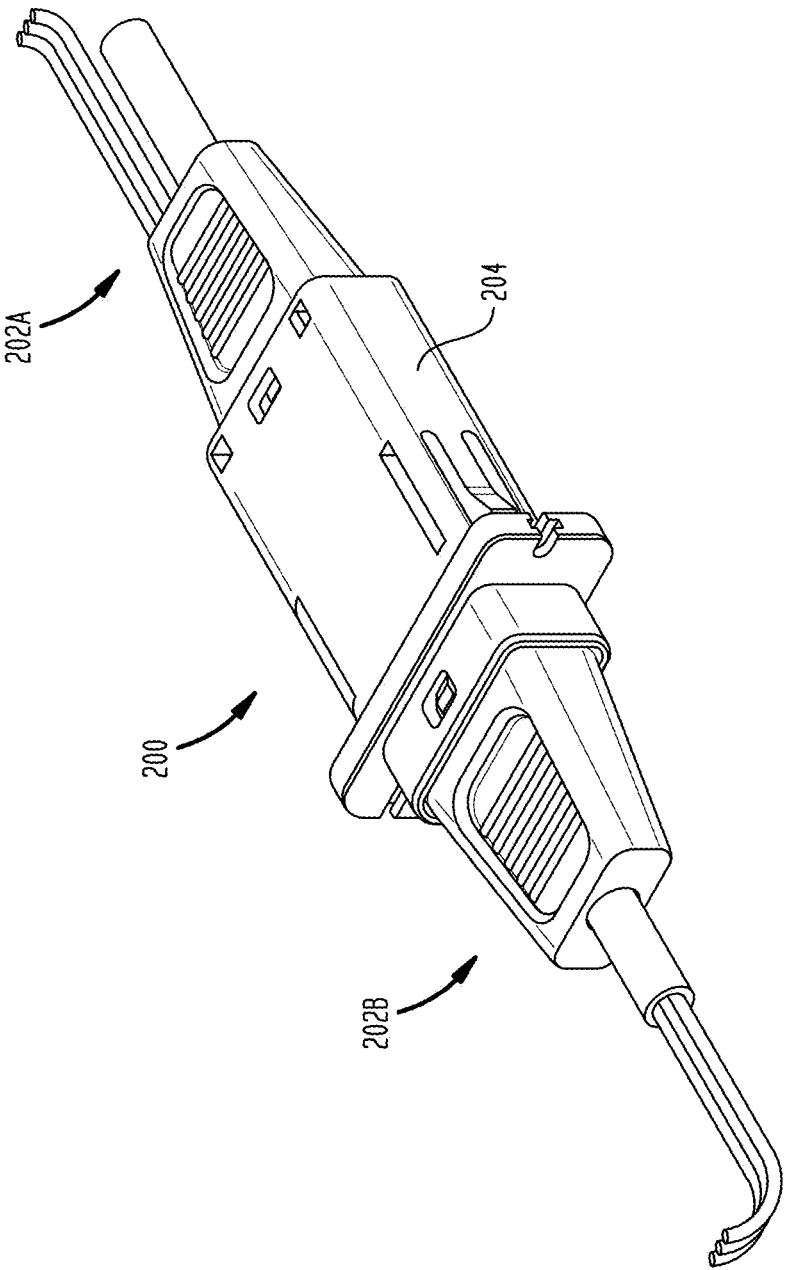

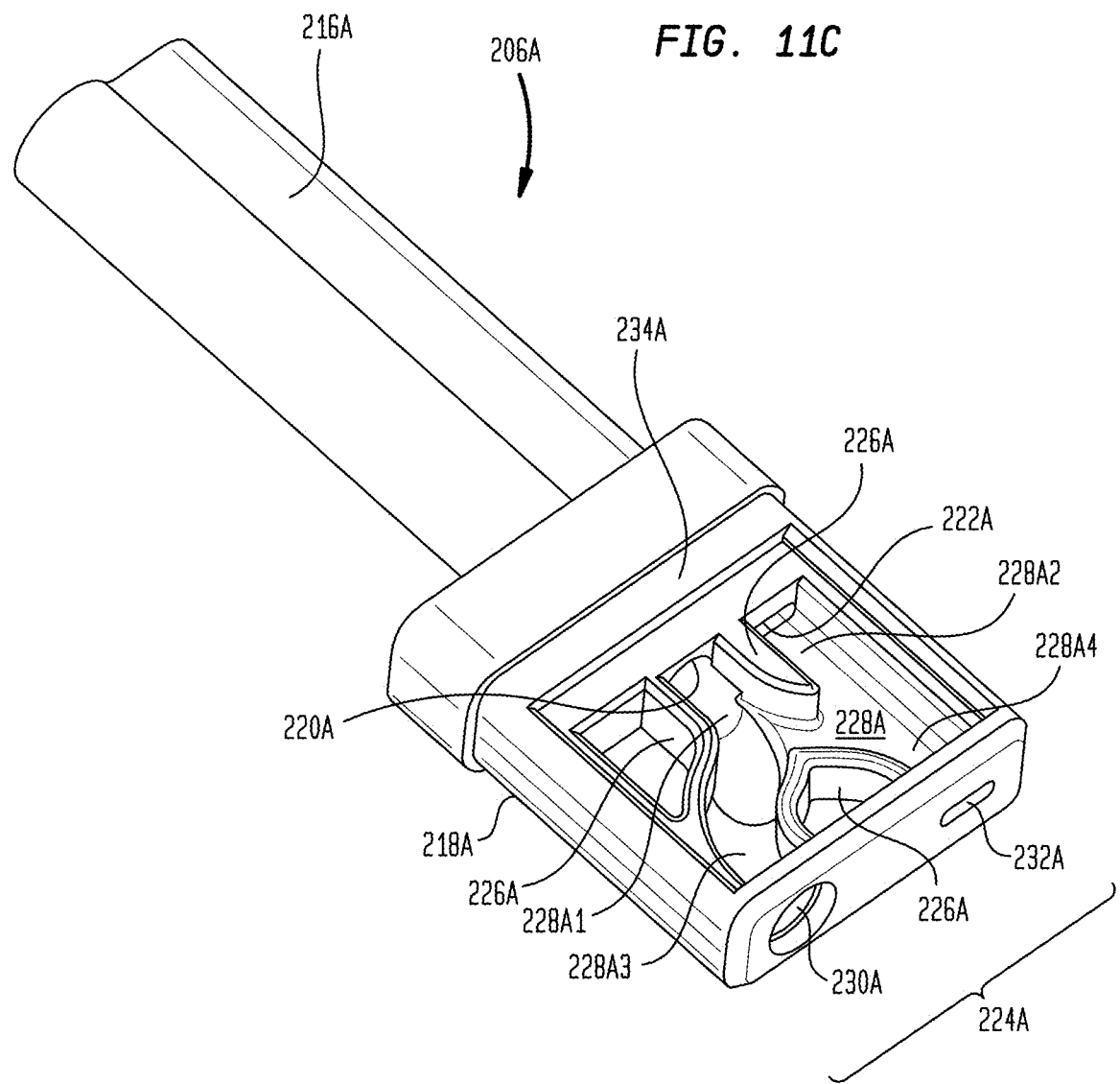

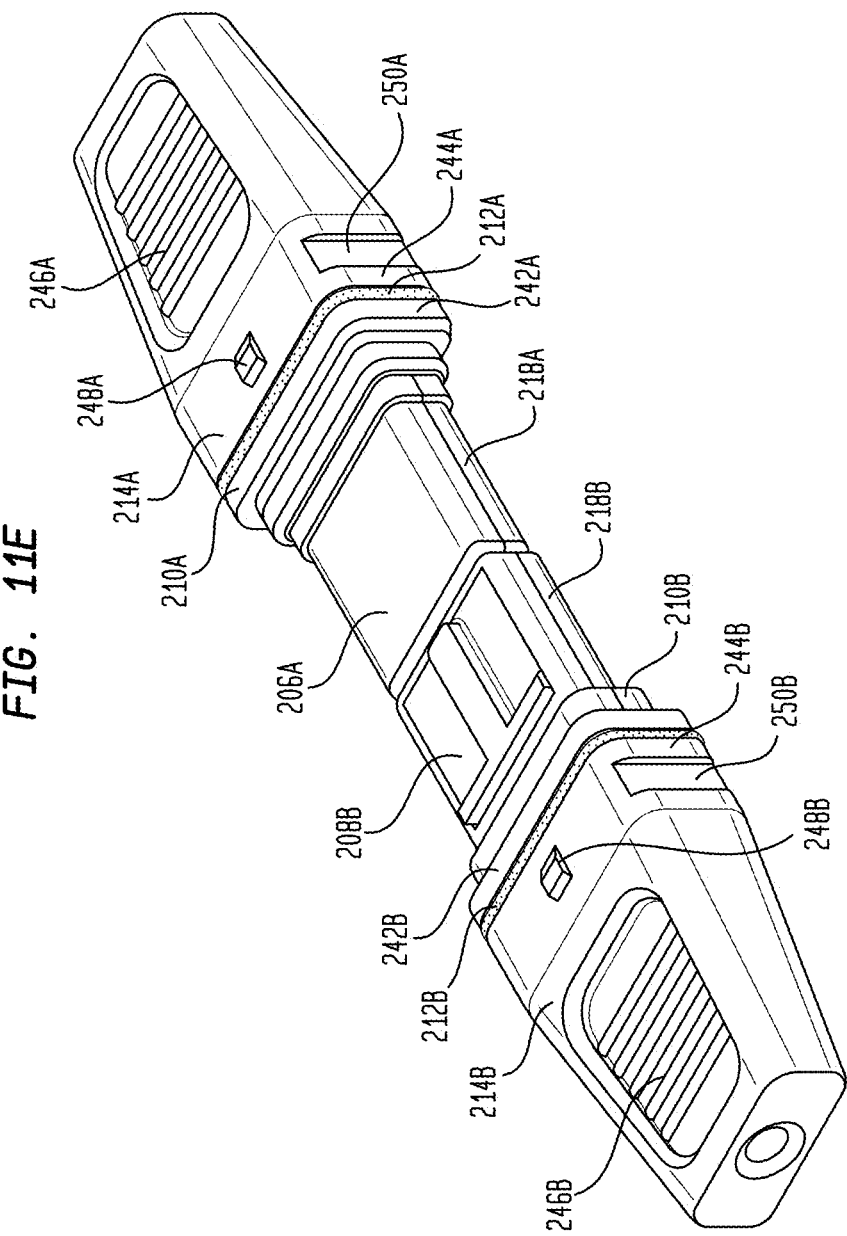

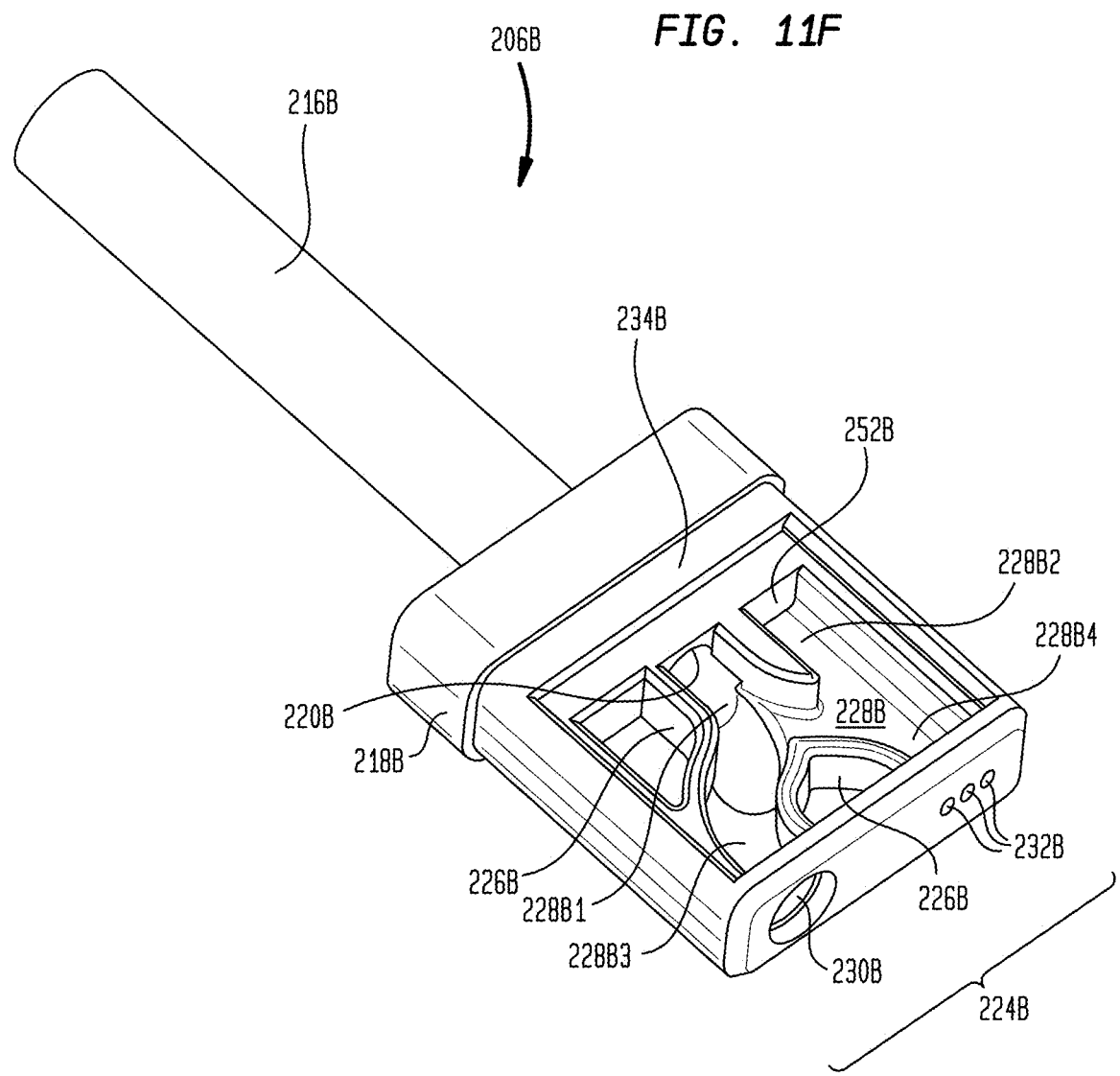

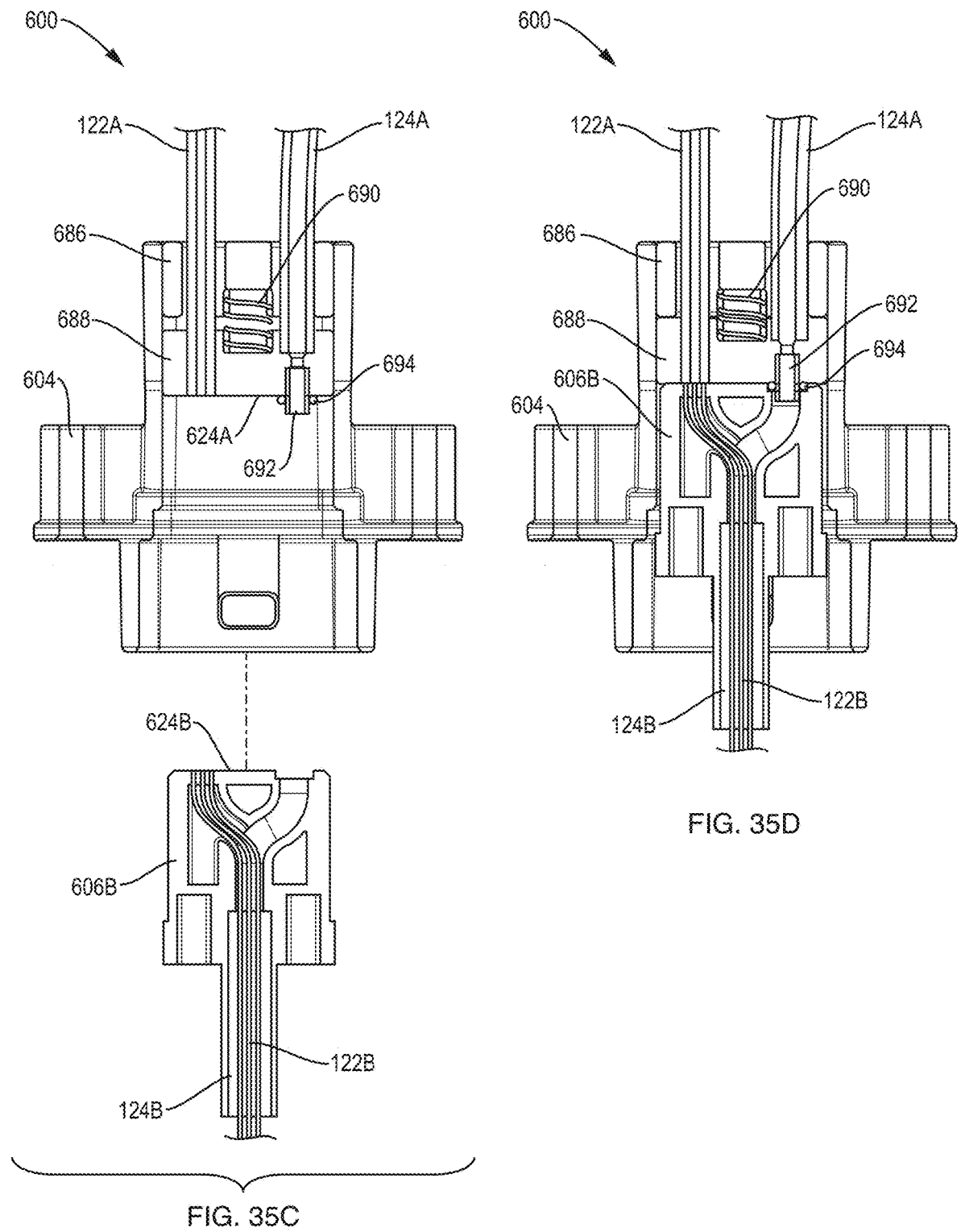

PROSTATE GLOVE, FINGERTIP OPTICAL ENCODER, CONNECTOR SYSTEM, AND RELATED METHODS

CROSS-REFERENCE TO RELATED APPLICATIONS

This application claims priority to U.S. Provisional Application No. 62/271,009 filed on Dec. 22, 2015 and entitled "PROSTATE GLOVE," U.S. Provisional Application No. 62/366,738 filed on Jul. 26, 2016 and entitled "PROSTATE GLOVE," and U.S. Provisional Application No. 62/378,809 filed on Aug. 24, 2016 and entitled "PROSTATE GLOVE, FINGERTIP OPTICAL ENCODER, CONNECTOR SYSTEM, AND RELATED METHODS," each of which is hereby incorporated by reference in its entirety.

FIELD

The present disclosure relates to systems and methods for measuring or evaluating an object. In some embodiments, systems and methods for measuring the prostate are provided.

BACKGROUND

Prostate problems are widespread in the male population, especially the older male population. In particular, benign prostatic hyperplasia (BPH) and prostate cancer are common in men over 50 years of age. Indeed, prostate cancer is the second most common cancer in men in the United States. Each year, there are more than 200,000 new cases and more than 30,000 deaths. However, if prostate cancer is detected early and treated effectively, the chance of survival improves significantly. Unfortunately, conventional methods for detecting prostate problems are wanting as many early stage cancers go undetected.

While ultrasound systems have been developed to diagnose prostate problems, such systems are very expensive. Most ultrasound imaging is performed by radiologists at an outside facility, or at the practitioner's office on a contract basis with a portable ultrasound unit. The technology and interpretation is difficult to master, requiring a time-consuming learning curve. Consequently, no routine examining system or technique exists which provides a high degree of accuracy in measuring prostate volume, nor is the required repeatability of results achieved.

Thus, the digital rectal examination continues to be the modality of choice for monitoring the prostate even though the process is very subjective. The standard exam is done by inserting a finger into the rectum and palpating or feeling the palpable surface of the prostate. The physical characteristics of the prostate size, contour, consistency, symmetry, and the presence or absence of nodularity, are assessed and recorded by attempting to translate the physician's subjective impressions into a written record. This method of data collection is inexact and makes comparisons from exam to exam very difficult.

Exemplary methods and devices for measuring the prostate are disclosed in U.S. Pat. No. 7,309,319, entitled "APPARATUS AND METHOD FOR MEASURING THE DIMENSIONS OF THE PALPABLE SURFACE OF THE PROSTATE," U.S. Publication No. 2009/0069721, entitled "APPARATUS AND METHOD FOR MEASURING THE DIMENSIONS OF THE PALPABLE SURFACE OF THE PROSTATE," U.S. Publication No. 2011/0172563, entitled "APPARATUS AND METHOD FOR MEASURING THE DIMENSIONS OF THE PALPABLE SURFACE OF THE PROSTATE," U.S. Pat. No. 8,694,079, entitled "DOUBLE MEMBRANE PROSTATE GLOVE," U.S. Publication No. 2014/0121562, entitled "PROSTATE GLOVE WITH MEASUREMENT GRID," U.S. Publication No. 2014/0121534, entitled "GRID FOR MEASURING PROSTATE VOLUME," U.S. Publication No. 2014/0121563, entitled "PROSTATE GLOVE WITH RECEIVER FIBERS," U.S. Pat. No. 8,838,214, entitled "FINGER CLIP FOR PROSTATE GLOVE," U.S. Publication No. 2014/0121535, entitled "CONNECTOR FOR USE WITH A PROSTATE MEASUREMENT SYSTEM," and U.S. Publication No. 2014/0121536, entitled "CONTROLLER FOR MEASURING PROSTATE VOLUME," each of which is hereby incorporated by reference in its entirety.

SUMMARY

Systems and methods are provided herein that generally involve measuring a prostate or other object. In some embodiments, a finger clip having a roller ring or wheel rotatably mounted thereto is disposed within an inflatable membrane. The roller ring can include a measurement pattern positioned opposite to optical fibers configured to receive light reflected from the measurement pattern. A user can put on the finger clip, position the membrane in proximity to a rectal wall overlying a prostate, and inflate the membrane. As the user slides their finger across the inside of the membrane, which is pressed against the rectal wall, the roller ring can rotate with respect to the fibers such that the fibers move relative to the measurement pattern. A controller can sense light reflected through the fibers from the reference pattern and calculate or estimate various attributes of the prostate based on the reflected light.

In some embodiments, a measurement device includes a ring that defines a measurement pattern on a surface thereof; a finger clip on which the ring is rotatably mounted; and one or more optical fibers mounted in the finger clip such that the ring rotates with respect to the fibers as the ring rotates relative to the finger clip and such that the fibers are held at a substantially fixed distance from the measurement pattern as the ring rotates relative to the finger clip.

The device can include an inflatable membrane disposed over the finger clip. The inflatable membrane can include a textured or knurled outer surface. The inflatable membrane can include a constraint member configured to control the direction and/or degree to which the inflatable membrane inflates when an inflation medium is delivered to an interior thereof. The constraint member can include a band that extends along a dorsal surface of the membrane, across a closed distal end of the membrane, and returns along a ventral surface of the membrane. The device can include an inflation tube in which the fibers are disposed, the inflation tube being configured to deliver an inflation medium to an interior of an inflatable membrane disposed over the finger clip. The measurement pattern can be formed on or coupled to a proximal-facing surface of the ring. The finger clip can include a finger clip cap on which the ring is rotatably mounted and a finger clip base in which the fibers are fixedly mounted. The device can include a shroud coupled to the finger clip to cover a dorsal portion of the ring. The device can include a proximal sleeve configured to form a seal between an inflatable membrane disposed over the finger clip and a finger of a user. The finger clip can include a base portion having an axle on which the ring is rotatably mounted. The finger clip can include a fiber guide in which the fibers are fixedly mounted. The finger clip can include a locking pin that retains the ring on the axle. A surface of the ring that engages a membrane during a measurement can be disposed distal to a distal-most extent of a user's finger when the measurement device is worn by the user. A rotation axis of the ring can be oriented at an oblique angle with respect to a longitudinal axis of a base portion of the finger clip. A rotation axis of the ring can be oriented at an oblique angle with respect to a longitudinal axis of a user's finger when the user's finger is disposed in the finger clip. The oblique angle can be between about 40 degrees and about 50 degrees. The ring and the finger clip can be disposed in a closed volume defined between a digit extension of a glove and an outer membrane disposed over the digit extension. The digit extension can be coupled to the glove by first and second rings. The membrane can be sealed to the first ring. The digit extension can be sealed to the first ring. The glove can be sealed to the second ring. The second ring can be rotatable with respect to the first ring. The one or more optical fibers can include a first transmitting fiber configured to direct light generated by an external light source onto the measurement pattern; a first receiver fiber configured to direct light reflected by the measurement pattern to a first external optical detector; and a second receiver fiber configured to direct light reflected by the measurement pattern to a second external optical detector. An output window of the first transmitting fiber, an input window of the first receiver fiber, and an input window of the second receiver fiber can be disposed adjacent to one another in a delta configuration.

In some embodiments, a method of measuring a prostate includes positioning a finger clip having a ring rotatably mounted thereto in proximity to a rectal wall adjacent the prostate, the finger clip having at least one optical fiber coupled thereto and a membrane disposed therearound to form a closed volume; inflating the closed volume such that the membrane contacts the rectal wall; and rolling the ring along an interior surface of the membrane from a first lateral margin of the prostate to a second lateral margin of the prostate, thereby rotating a measurement pattern of the ring past a distal end of the at least one optical fiber and generating information indicative of a distance traveled by the at least one optical fiber with respect to the measurement pattern.

The method can include using at least one processor to correlate the information indicative of a distance traveled by the at least one optical fiber with a palpable surface width of the prostate. The method can include using at least one processor to correlate the palpable surface width of the prostate with a volume of the prostate.

In some embodiments, a connector system includes a connector housing; a slider disposed in the connector housing and configured to translate with respect to the connector housing, a distal end of the slider defining a first mating interface; a first fluid lumen extending through the slider from an opening at the proximal end of the slider to an opening formed in the first mating interface; a first set of optical fibers extending through the slider and terminating at the first mating interface; a connector body having proximal and distal ends, the proximal end defining a second mating interface; a second fluid lumen extending through the connector body from an opening formed in the second mating interface to an opening at the distal end of the connector body; a second set of optical fibers extending through the connector body and terminating at the second mating interface; wherein the connector housing is configured to maintain the first mating interface in alignment with the second mating interface such that the first set of optical fibers is in optical communication with the second set of optical fibers and the first fluid lumen is in fluid communication with the second fluid lumen.

The system can include a base disposed in the connector housing and a spring that biases the slider away from the base. The base can be non-movably coupled to the housing and the first fluid lumen and the first set of optical fibers can be configured to slide within the base. Insertion of the connector body into the housing can cause the slider to translate proximally and compress the spring, the spring thereby urging the first mating interface into contact with the second mating interface. The system can include a nipple in fluid communication with the first fluid lumen and protruding distally from the slider. The system can include a gasket disposed around the nipple. The first fluid lumen and the first set of optical fibers can be configured to translate with the slider relative to the housing. The slider can include a projection slidably received within a track formed in the housing.

In one aspect, an examination device is provided that includes a glove configured to be removably disposed around a human hand, the glove having a digit extension configured to receive a human digit of a human hand disposed within the glove. The device can include a membrane disposed over at least a portion of the digit extension, the membrane and the digit extension forming a closed volume therebetween. The device can also include a reference pattern disposed within the closed volume, and at least one optical fiber extending into the closed volume and in optical communication with the reference pattern, the optical fiber being configured to move relative to the reference pattern.

An inflation tube can extend into the closed volume through which an inflation medium can be supplied to inflate the membrane relative to the digit extension. In one embodiment, the at least one fiber can extend through the inflation tube. In certain aspects, the membrane can be in the form of an elongate tubular body having a closed distal end and a proximal end that is sealed circumferentially around the digit extension. The membrane can be sealed to the digit extension, for example, using an adhesive. In other aspects, the optical fiber can be coupled to the digit extension and the reference pattern can be coupled to the membrane. In an exemplary embodiment, the at least one optical fiber can include a first transmitting fiber configured to direct light generated by an external light source onto the reference pattern, and a first receiver fiber configured to direct light reflected by the reference pattern to a first external optical detector. The at least one optical fiber can further include a second receiver fiber configured to direct light reflected by the reference pattern to a second external optical detector. The first transmitter fiber, the first receiver fiber, and the second receiver fiber can extend through an inflation tube configured to supply an inflation medium to the closed volume.

In another aspect, an examination device is provided that includes a glove configured to be removably disposed around a human hand, an inflatable membrane sealed around at least a portion of the glove to define a closed volume between the membrane and the glove, a reference pattern coupled to a surface of the membrane, and at least one optical fiber extending into the closed volume and coupled to the glove such that the at least one optical fiber is movable with the portion of the glove relative to the membrane, the at least one optical fiber being in optical communication with the reference pattern.

The at least one optical fiber can include a first transmitter fiber, a first receiver fiber, and a second receiver fiber. The device can include an inflation tube in fluid communication with the closed volume for delivering an inflation fluid into the closed volume to inflate the membrane relative to the glove. The at least one optical fiber can extend through the inflation tube.

In another aspect, a method of measuring a prostate is provided that includes positioning a digit extension of a glove in proximity to a rectal wall adjacent the prostate, the digit extension having at least one optical fiber coupled thereto and a membrane disposed therearound to form a closed volume. The method can also include inflating the closed volume relative to the digit extension such that the membrane contacts the rectal wall, and moving the at least one optical fiber across a reference pattern disposed within the closed volume from a first lateral margin of the prostate to a second lateral margin of the prostate, thereby generating information indicative of a distance traveled by the at least one optical fiber.

The method can include using at least one processor to correlate the information indicative of a distance traveled by the at least one optical fiber with a palpable surface width of the prostate. The method can include using at least one processor to correlate the palpable surface width of the prostate with a volume of the prostate. The at least one optical fiber can be coupled to the digit extension, the reference pattern can be coupled to the membrane, and moving the at least one optical fiber can include moving the digit extension relative to the membrane.

In another aspect, an examination device is provided that includes an inflatable membrane defining an enclosed volume, and a substrate coupled to an interior surface of the membrane and having a plurality of reference lines formed on the substrate and arranged along a measurement axis. The substrate can be configured such that, when the inflatable membrane is inflated, a spacing between the plurality of reference lines remains constant.

The indicia can be printed on the substrate. The substrate can include or be formed of polyethylene. The substrate can be attached to the membrane only along a central axis of the substrate. The central axis can extend perpendicular to the measurement axis. The substrate can be attached to the membrane only at a center point of the substrate. The substrate can be attached to the membrane using at least one of an adhesive and a weld. The substrate can have a thickness between about 0.5 mils and about 6.0 mils. The substrate can have a thickness of about 2 mils. The device can include an optical fiber extending into the enclosed volume defined by the membrane. The membrane can be disposed over a digit extension of a glove.

In another aspect, a method of manufacturing an examination device is provided that includes attaching a substrate to a membrane such that the membrane is stretchable independently from the substrate, the substrate having a reference pattern comprising a plurality of indicia formed on the substrate and spaced along a measurement axis. The method can include positioning the membrane over a digit extension of a glove configured to be removably disposed around a human hand, and sealing a perimeter of the membrane to the glove such that the digit extension is independently movable relative to the reference pattern.

The substrate can be attached to the membrane only along a central axis of the substrate, the central axis extending perpendicular to the measurement axis. The indicia can be printed on the substrate. The substrate can be attached to the membrane only at a center point of the substrate. The substrate can be attached to the membrane using at least one of an adhesive and a weld. The method can include coupling an optical fiber to the glove such that a terminal end of the optical fiber extends between the membrane and the glove.

In another aspect, a method of measuring a prostate is provided that includes positioning a membrane in proximity to a rectal wall adjacent a prostate. The method can include inflating the membrane such that the membrane contacts the rectal wall, wherein a substrate attached to an interior surface of the membrane has a plurality of reference lines formed thereon, the reference lines defining a space therebetween that remains constant as the membrane is inflated. The method can include moving at least one optical fiber extending into an interior volume of the membrane across the plurality of reference lines to generate information indicative of a distance traveled by the at least one optical fiber.

The membrane can be disposed around a digit extension of a glove, and inflating the membrane can expand an interior volume between the glove and the membrane.

In another aspect, an examination device is provided that includes a glove configured to be removably disposed over a human hand, a membrane disposed over a portion of the glove and defining an enclosed volume between the glove and the membrane, and a reference pattern comprising a plurality of indicia disposed on the membrane and arranged along a measurement axis.

The indicia can be printed on the membrane. The indicia can be printed on a substrate coupled to the membrane. A spacing between the plurality of indicia as measured along the measurement axis can be configured to remain constant upon inflation and deflation of the membrane. The plurality of indicia can include lines extending perpendicular to the measurement axis. The lines can be separated by spaces having a width as measured along the measurement axis that is equal to a width of the lines as measured along the measurement axis. The lines can be separated by spaces having a width as measured along the measurement axis that is less than half of a width of the lines as measured along the measurement axis. The device can include an optical fiber extending into the enclosed volume, the lines being separated by spaces having a width as measured along the measurement axis that is less than a diameter of the optical fiber. The lines can have a width as measured along the measurement axis of approximately 0.7 mm and the lines can be separated by spaces having a width as measured along the measurement axis of approximately 0.3 mm. The plurality of indicia can define a uniform series of alternating dark and light portions. The plurality of indicia can extend along a portion of the substrate having a width a measured along the measurement axis of about 2 inches and a height as measured along an axis perpendicular to the measurement axis of about 1.5 inches.

In another aspect, an examination device is provided that includes an inflatable membrane configured to be disposed over and sealed around a digit extension of a glove for a human hand, the membrane defining an enclosed volume. The device can include a non-inflatable substrate coupled to an interior surface of the inflatable membrane, the non-inflatable substrate having a reference pattern disposed thereon, the reference pattern comprising a plurality of indicia arranged along a measurement axis.

The plurality of indicia can extend substantially parallel to one another. The plurality of indicia can define a uniform series of alternating dark and light portions. The plurality of indicia can be separated by spaces having a width that is equal to a width of the lines. The plurality of indicia can be separated by spaces having a width that is less than half of a width of the lines. The device can include an optical fiber extending into the enclosed volume, the plurality of indicia being separated by spaces having a width that is less than a diameter of the optical fiber. The plurality of indicia can have a width of approximately 0.7 mm and the lines can be separated by spaces having a width of approximately 0.3 mm.

In another aspect, an examination device is provided that includes a membrane defining an interior volume, a reference pattern disposed within the interior volume of the membrane, an illumination fiber extending into the interior volume of the membrane and configured to transmit light to the reference pattern through an output window, a first receiving fiber extending into the interior volume of the membrane and configured to receive light reflected from the reference pattern through a first input window, and a second receiving fiber extending into the interior volume of the membrane and configured to receive light reflected from the reference pattern through a second input window.

The output window can be formed in a terminal distal end of the illumination fiber, the first input window can be formed in a terminal distal end of the first receiving fiber, and the second input window can be formed in a terminal distal end of the second receiving fiber. The output window, the first input window, and the second input window can be disposed adjacent to one another in a delta configuration. The reference pattern can include a plurality of indicia arranged along a measurement axis and the first input window and the second input window can be arranged in a line that is substantially parallel to the measurement axis. The plurality of indicia can include a series of lines spaced equally along the measurement axis. The illumination fiber, the first receiving fiber, and the second receiving fiber can be configured to transmit near infrared light. The illumination fiber, the first receiving fiber, and the second receiving fiber can each have a diameter of approximately 0.5 mm.

In another aspect, a method of measuring an object is provided that includes positioning a reference pattern in proximity to an object, the reference pattern comprising alternating light and dark spaces arranged along a measurement axis, and positioning an optical receiver comprising an illumination fiber and first and second receiver fibers over the reference pattern such that an output window of the illumination fiber is aimed at the reference pattern and such that an input window of the first receiving fiber and an input window of the second receiving fiber are disposed along a line that is substantially parallel to the measurement axis. The method can include moving the optical receiver along the line relative to the reference pattern, and detecting a change in direction of movement of the optical receiver by measuring the light received by the first receiving fiber in time relation to the light received by the second receiving fiber.

In another aspect, an examination device is provided that includes a glove having a digit extension, a membrane disposed over at least a portion of the digit extension, the membrane and the digit extension forming a closed volume therebetween, and a finger clip attached to the digit extension and disposed within the closed volume. The device can include at least one illumination optical fiber and at least one receiving optical fiber extending into the closed volume and through the finger clip, and an inflation tube extending into the closed volume and configured to introduce an inflation medium into the closed volume.

The finger clip can be attached to the digit extension such that it extends along a dorsal surface of the digit extension and down across a distal tip of the digit extension. The at least one illumination optical fiber and the at least one receiving optical fiber can extend through the inflation tube. The inflation tube can terminate proximal to a proximal end of the finger clip. The at least one illumination optical fiber and the at least one receiving optical fiber can extend through an open channel formed in the finger clip and through a tunnel oriented substantially perpendicular to the open channel. The at least one illumination optical fiber and the at least one receiving optical fiber can terminate at a distance from a distal end of the tunnel. The distance can be between about 0.25 mm and about 0.5 mm. The digit extension can be or can include a forefinger extension.

In another aspect, a method of making an examination device is provided that includes forming an open channel in a finger clip, wherein the finger clip is configured to be disposed on a user's finger, and forming a through hole in the finger clip approximately perpendicular to the open channel such that the through hole intersects the open channel and provides a working connection from the open channel to a distal end of the finger clip. The method can include positioning at least one fiber optic within the open channel and the through hole such that an optical window formed in a terminal distal end of the fiber optic is aimed in a direction configured to be perpendicular to a dorsal surface of a user's finger.

The at least one fiber optic can include at least one illumination fiber optic and at least one receiving fiber optic. The finger clip and the open channel can be formed by injection molding. The finger clip can be formed from injection molded, soft-durometer urethane. The method can include routing the at least one fiber optic through an inflation tube that terminates proximal to a proximal end of the finger clip.

In another aspect, a method of measuring an object is provided that includes positioning a digit extension of a glove around a user's hand such that a finger clip attached to the digit extension extends along a dorsal surface of a digit of the user's hand and down across a distal tip of the digit. The method can include positioning the digit extension in proximity to an object, inflating a membrane disposed around the digit extension to inflate the membrane relative to the digit extension and to position a reference pattern coupled to the membrane at a distance apart from a distal tip of the finger clip, and moving the distal tip of the finger clip relative to the reference pattern to generate information indicative of a distance traveled by the distal tip of the finger clip relative to the reference pattern.

In another aspect, a connector system is provided that includes a first connector body having proximal and distal ends, the distal end defining a first mating interface, a first fluid lumen extending through the first connector body from an opening at the proximal end of the first connector body to an opening formed in the first mating interface, and a first set of optical fibers extending through the first connector body and terminating at the first mating interface. The connector system can include a second connector body having proximal and distal ends, the proximal end defining a second mating interface, a second fluid lumen extending through the second connector body from an opening formed in the second mating interface to an opening at the distal end of the second connector body, and a second set of optical fibers extending through the second connector body and terminating at the second mating interface. The connector system can include a connector housing configured to maintain the first mating interface in alignment with the second mating interface such that the first set of optical fibers is in optical communication with the second set of optical fibers and the first fluid lumen is in fluid communication with the second fluid lumen.

The connector housing can be formed integrally with at least one of the first connector body and the second connector body. When mated, the first fluid lumen and the second fluid lumen can form a continuous fluid-tight passage having proximal and distal terminal ends. The first set of optical fibers can enter the fluid-tight passage at a location other than the proximal and distal terminal ends. The first set of optical fibers can extend through less than an entire length of the first fluid lumen. The second set of optical fibers can extend through the second fluid lumen and through a tube coupled to the distal end of the second connector body. The first set of optical fibers can extend from the proximal end of the first connector body into an interior of the first fluid lumen. The system can include a first key coupled to the first connector body and configured to cooperate with a corresponding recess formed in the connector housing such that the first connector body can only be inserted into the connector housing in one orientation. The system can include a first strain relief overmold disposable over the first connector body and a second strain relief overmold disposable over the second connector body.

In another aspect, an examination system is provided that includes a glove having a digit extension, a membrane disposed over at least a portion of the digit extension, the membrane and the digit extension forming a closed volume therebetween, and an inflation tube extending into the closed volume and configured to receive an inflation fluid for inflating the membrane. The system can include at least one optical fiber extending through the inflation tube and into the closed volume, and a connector coupled to a proximal end of the inflation tube, the connector including an inflation lumen extending from the inflation tube to a mating interface, wherein an optical opening of the at least one optical fiber terminates at the mating interface.

The system can include a first key coupled to the connector and configured to allow the connector to mate to a second connector in only one orientation.

In another aspect, an examination system is provided that includes an optical receiver coupled to at least one optical fiber, an inflation medium supply coupled to an inflation tube, and a connector coupled to a distal end of the inflation tube, the connector including an inflation lumen extending from the inflation tube to a mating interface, wherein an optical opening of the at least one optical fiber terminates at the mating interface.

The at least one optical fiber can enter the inflation lumen at a location within the connector. The system can include a light source coupled to the at least one optical fiber. The system can include at least one processor configured to interpret signals output from the optical receiver. The inflation medium supply can include at least one of a pump and a tank of compressed air.

In another aspect, a system for estimating the volume of a prostate is provided that includes a processor programmed to provide a sensor input module configured to receive information indicative of light reflected from a reference pattern as an optical fiber is moved across the reference pattern from a first prostate lateral margin to a second prostate lateral margin. The processor can be programmed to provide a distance measuring module configured to convert the received information into a prostate palpable surface width ($PS_W$), and a volume estimation module configured to estimate a volume (V) of the prostate based on the palpable surface width ($PS_W$).

The volume estimation module can estimate the volume (V) as $V=PS_W^3 \times k$, wherein k is a constant. The constant k can be between about 0.35 and about 0.45. The constant k can be about 0.3926991. The processor can be programmed to provide an error detection module configured to detect that a measurement error has occurred when the received information indicates that a direction of movement of the optical fiber changed during a measurement. The processor can be programmed to provide a display module configured to drive a display to display the estimated volume (V). The processor can be programmed to provide an inflation control module configured to actuate a pump or a control valve to inflate a membrane disposed around a digit extension of a glove to a predetermined pressure or with a predetermined volume of air. The processor can be programmed to provide an RFID interface module configured to receive information indicative of an RFID signature of a disposable unit and to determine whether the disposable unit is an authenticated disposable unit.

In another aspect, a method of estimating the volume of a prostate is provided that includes moving an optical fiber across a reference pattern from a first lateral margin of a prostate to a second lateral margin of the prostate to generate information indicative of light reflected from the reference pattern. The method can include using at least one processor to convert the generated information into a prostate palpable surface width ($PS_W$), and using the at least one processor to estimate a volume (V) of the prostate based on the palpable surface width ($PS_W$).

The method can include estimating the volume (V) as $V=PS_W^3 \times k$, wherein k is a constant. The constant k can be between about 0.35 and about 0.45. The constant k can be about 0.3926991. The method can include using the at least one processor to detect that a measurement error has occurred when the generated information indicates that a direction of movement of the optical fiber changed during a measurement. The method can include using the at least one processor to drive a display to display the estimated volume (V). The method can include using the at least one processor to actuate a pump or a control valve to inflate a membrane disposed around a digit extension of a glove to a predetermined pressure or with a predetermined volume of air. The method can include using the at least one processor to receive information indicative of an RFID signature of a disposable unit and to determine whether the disposable unit is an authenticated disposable unit.

BRIEF DESCRIPTION OF THE DRAWINGS

The invention will be more fully understood from the following detailed description taken in conjunction with the accompanying drawings, in which:

FIG. 7C is a schematic view of the position and orientation of optical fiber windows relative to a reference pattern;

FIG. 11A is a perspective view of a connector system;

FIG. 11C is a perspective view of a first connector body;

FIG. 11E is a perspective view of a connector system;

FIG. 11F is a perspective view of a second connector body;

FIG. 35C is a sectional top view of the connector system of FIG. 35A in a disconnected state;

FIG. 35D is a sectional top view of the connector system of FIG. 35A in a connected state;

DETAILED DESCRIPTION

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments.

Systems and methods are provided herein that generally involve measuring a prostate or other object. In some embodiments, a finger clip having a roller ring or wheel rotatably mounted thereto is disposed within an inflatable membrane. The roller ring can include a measurement pattern positioned opposite to optical fibers configured to receive light reflected from the measurement pattern. A user can put on the finger clip, position the membrane in proximity to a rectal wall overlying a prostate, and inflate the membrane. As the user slides their finger across the inside of the membrane, which is pressed against the rectal wall, the roller ring can rotate with respect to the fibers such that the fibers move relative to the measurement pattern. A controller can sense light reflected through the fibers from the reference pattern and calculate or estimate various attributes of the prostate based on the reflected light.

Systems and methods are provided herein that generally involve measuring a prostate or other object. In some embodiments, a reference pattern is positioned adjacent to the object to be measured and light reflected from the reference pattern is measured or interpreted to estimate various attributes of the object, such as its volume. For example, a membrane can be sealed over a glove to form a closed volume. The closed volume can be configured to be expanded via an inflation tube, and a reference pattern can be disposed within the closed volume along with one or more optical fibers. In use, a user can put on the glove, position the membrane in proximity to a rectal wall overlying a prostate, and inflate the membrane. As the user slides their finger across the rectal wall, the optical fibers move relative to the reference pattern and a controller senses light reflected through the fibers from the reference pattern. The controller can calculate or estimate various attributes of the prostate based on the reflected light, such as the palpable surface width or volume.

System Overview

Figure 1:
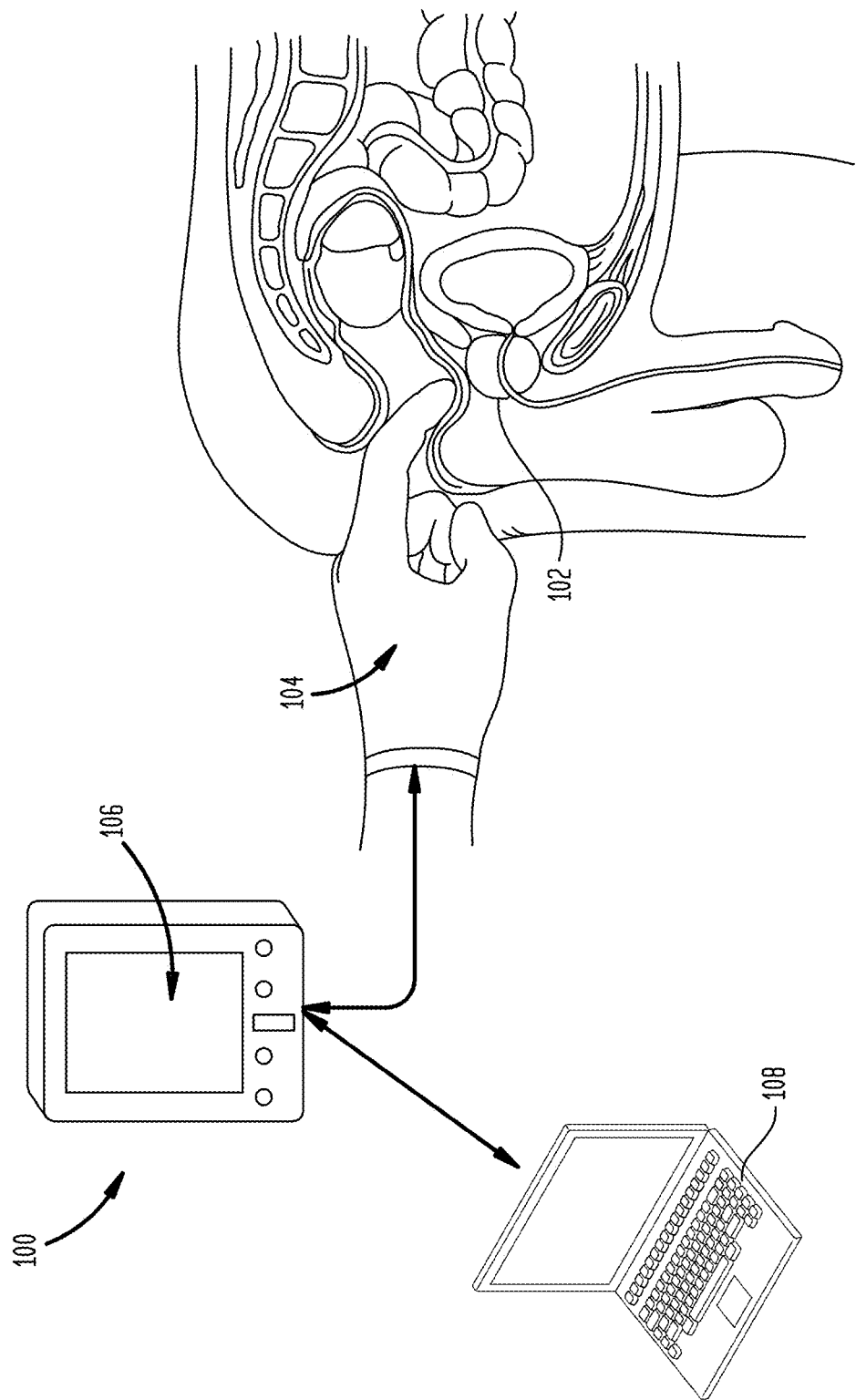
FIG. 1 is a schematic view of an examination system and a patient.

FIG. 1 illustrates an exemplary embodiment of an examination system 100 for measuring an object (e.g., a prostate 102). The system 100 can include a measurement assembly 104 configured to provide information indicative of a dimension of the object to a controller 106. The controller 106 can be configured to estimate one or more properties or conditions of the object based on the information provided by the measurement assembly 104. The controller 106 can also be coupled to a computer system 108 for storing or further processing the information.

Figure 2:
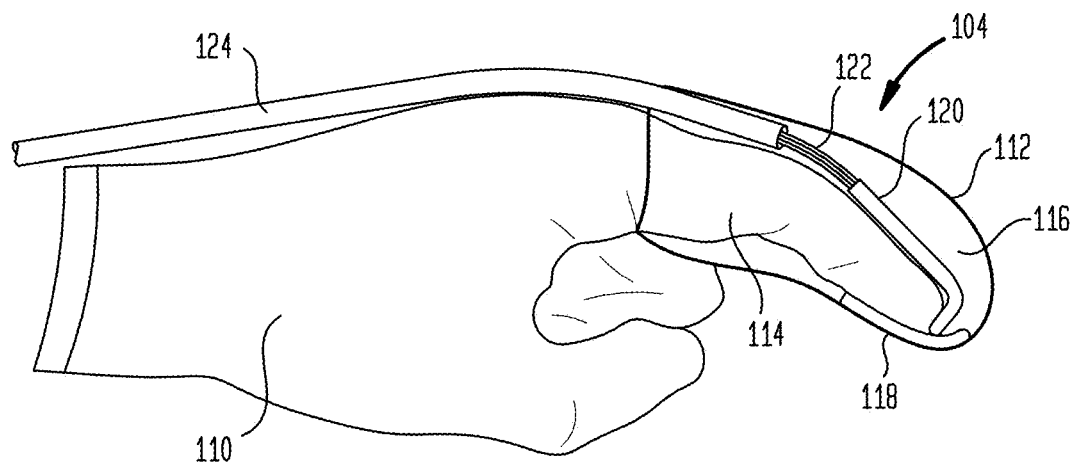
FIG. 2 is a partially-transparent side view of a measurement assembly.

As shown in FIG. 2, the measurement assembly 104 can include a glove 110 with a membrane 112 disposed over a digit extension 114 thereof to define a closed volume 116 between the glove 110 and the membrane 112. A reference pattern 118 can be formed on or coupled to an interior surface of the membrane 112 such that the reference pattern is disposed within the closed volume 116. The assembly 104 can also include a finger clip 120 coupled to the digit extension 114 beneath the membrane 112. One or more optical fibers 122 can be mounted in a channel or lumen formed in the finger clip 120. The optical fibers 122 can be configured to transmit light generated by a light source in the controller 106 to the reference pattern 118, and to transmit light reflected from the reference pattern to an optical sensor in the controller. The assembly 104 can also include an inflation tube 124 extending into the closed volume 116 and configured to supply an inflation medium to the closed volume to inflate the membrane 112 and expand the closed volume, or to extract an inflation medium from the closed volume to deflate the membrane 112 and reduce the closed volume. The optical fibers 122 can extend through the inflation tube 124, and a suitable connector can be provided at a proximal end of the inflation tube for coupling the inflation tube and the optical fibers to the controller 106. In some embodiments, the measurement assembly 104 can be disposable, e.g., adapted for a single use or for use with a single patient, whereas the controller 106 can be reusable.

In an exemplary method of operation, the measurement assembly 104 can be worn by a user (e.g., disposed over the user's hand). The user can then position the membrane 112 in proximity to an area to be measured (e.g., a patient's rectal wall, adjacent the prostate). The membrane can be inflated using the controller 106. With the membrane 112 remaining substantially stationary and the light source activated, the user can swipe their gloved finger and the finger clip 120 attached thereto from a first lateral margin of the prostate to a second lateral margin of the prostate. As the finger clip 120 moves across the prostate, light reflected from the reference pattern 118 can be transmitted to the controller 106, where it can be processed to determine or estimate various properties of the prostate, such as the palpable surface width of the prostate or the volume of the prostate.

Measurement Assembly

Glove

Figure 3:
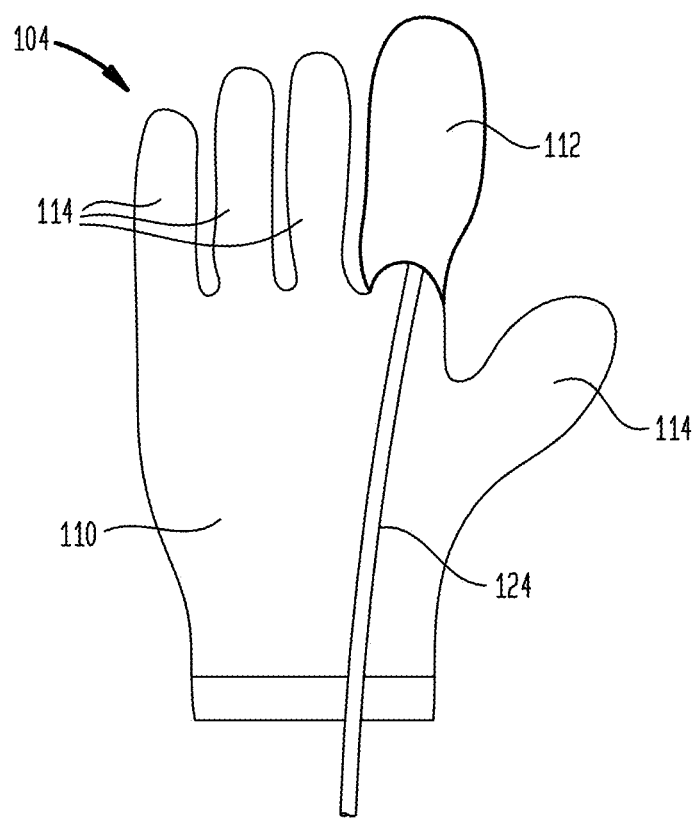
FIG. 3 is a top view of a measurement assembly.

FIG. 3 illustrates a top view of the measurement assembly 104. As shown, the measurement assembly 104 can include a glove 110 with one or more digit extensions 114 corresponding to, and configured to receive, the fingers of a human hand. The glove 110 can thus be configured to be removably disposed around a human hand or a portion thereof. The glove 110 can be formed from any of a variety of materials suitable for use in a medical environment, including latex, natural rubber latex, neoprene, nitrile, vinyl, Vytex, and so forth. In some embodiments, the glove 110 can be a standard exam glove or surgical glove. In the illustrated embodiment, a complete glove is shown (e.g., a glove having five digit extensions and configured to envelop the entirety of a human hand). It will be appreciated, however, that in some embodiments less than a complete glove can be used. For example, the glove can be in the form of a finger cot configured to cover only a single finger or portion thereof. In other embodiments, the glove can be omitted altogether and the membrane 112 can be sealed directly around the user's finger.

Membrane

The membrane 112 can be disposed over a portion of the glove 110 (e.g., one or more digit extensions 114 thereof), or can be disposed over the entirety of the glove 110. In some embodiments, the membrane 112 can be defined by a finger cot having an elongate tubular structure with a closed distal end and an open proximal end. The membrane 112 can be positioned over a digit extension 114 of the glove 110, such as the forefinger digit extension, and the open proximal end of the membrane can be sealed circumferentially around the digit extension. The membrane 112 can be sealed to the glove 110 using any of a variety of techniques, including UV-curable and/or biocompatible cements or adhesives. Exemplary adhesives include Dymax 1202-M-SC and Dymax 222/450 (available from Dymax Corporation of Torrington, Conn.). The membrane 112 can be sealed to the glove 110 such that a closed, fluid-tight volume 116 is defined between the membrane and the glove. As discussed in further detail below, the inflation tube 124 can be sealed between the membrane 112 and the glove 110, such that the inflation tube extends into the closed volume 116 and a distal outlet of the inflation tube is disposed within the closed volume. The membrane 112 can be configured to expand or inflate when an inflation medium is supplied through the inflation tube 124, and to contract or deflate when an inflation medium is removed through the inflation tube. Like the glove 110, the membrane 112 can be formed from any of a variety of materials suitable for use in a medical environment, including latex, natural rubber latex, neoprene, nitrile, vinyl, Vytex, synthetic Polyisoprene, and so forth. In some embodiments, the membrane 112 is formed from the same material as the glove 110 and is configured to withstand strain forces applied thereto during inflation.

Reference Pattern

Figure 4A:
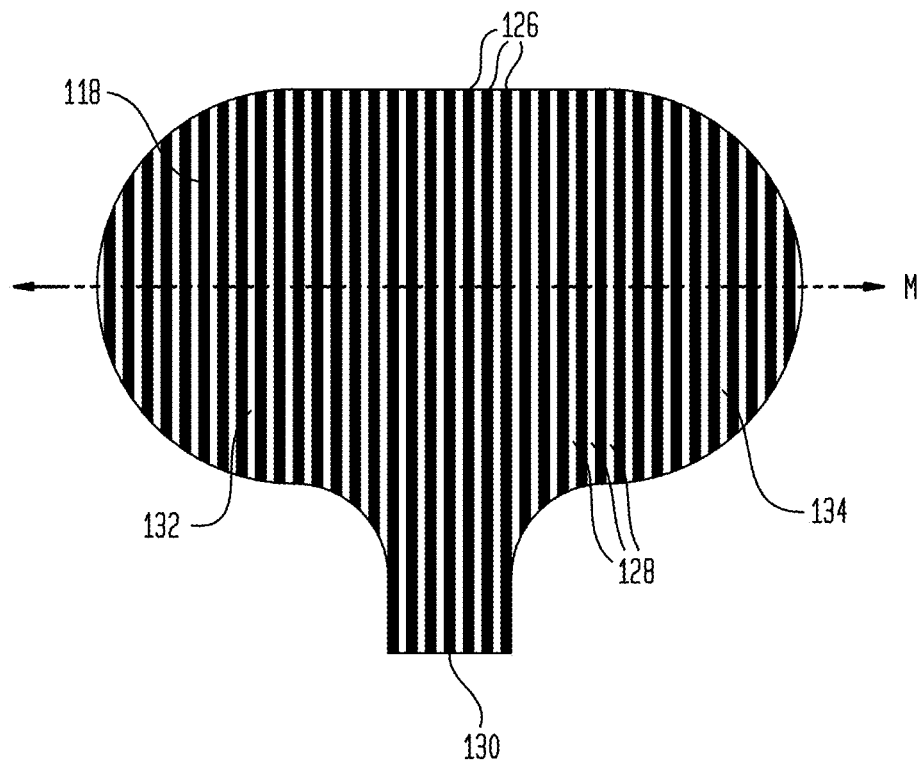
FIG. 4A is a top view of a reference pattern.
Figure 4B:
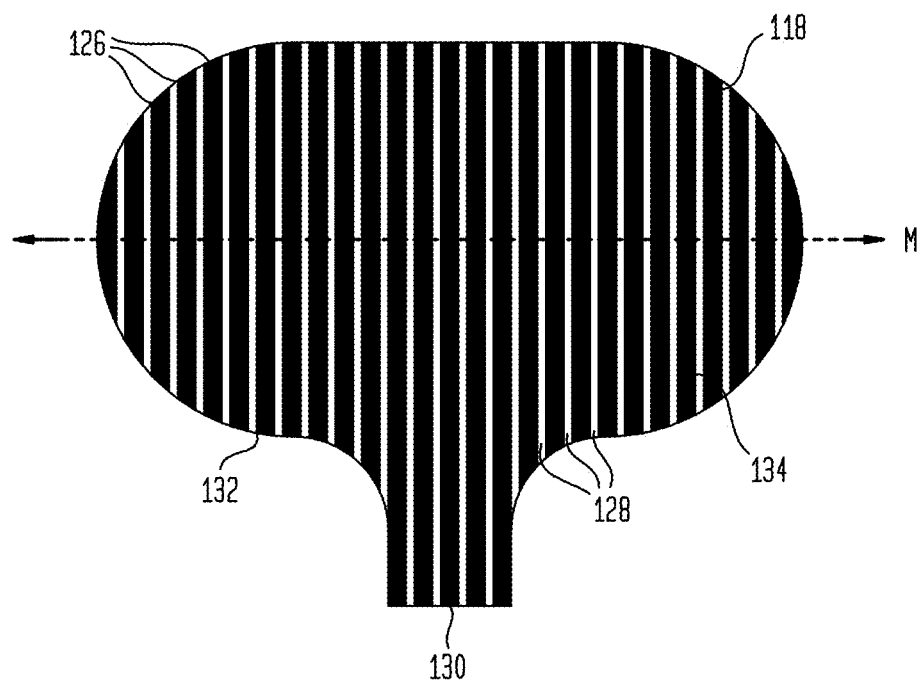
FIG. 4B is a top view of another reference pattern.

The reference pattern 118 can include any of a variety of indicia to provide a reference scale for measuring a dimension of an object. FIG. 4A illustrates an exemplary embodiment of a reference pattern 118 in which the indicia include a plurality of equally-spaced, parallel lines 126 defining alternating light and dark regions. In other words, the indicia provide a uniform series of alternating dark and light portions. The parallel lines 126 are arranged along a measurement axis M and extend perpendicular thereto. In the embodiment of FIG. 4A, the lines 126 have a width as measured along the measurement axis M that is equal to the width of the spaces 128 along the measurement axis. It will be appreciated, however, that any of a variety of spacing widths can be used. For example, as shown in FIG. 4B, the spaces 128 can have a width as measured along the measurement axis M that is less than half of the width of the lines 126 as measured along the measurement axis.

In operation, light reflected from the reference pattern 118 can be received though an input window formed in an optical fiber. In some embodiments, it can be desirable for the width of the light regions 128 of the reference pattern 118 to be less than the diameter or width of the optical fiber input window. This can advantageously prevent the fiber from receiving light reflected from a plurality of light regions 128 at the same time, and can thereby make pattern boundary crossings easier to identify from the sensor output data. Thus, in embodiments in which the optical fiber has an input window with a diameter of approximately 0.5 mm, the reference pattern 118 can include light regions 128 having a width as measured along the measurement axis M of about 0.3 mm and dark regions 126 having a width as measured along the measurement axis of about 0.7 mm.

The size and shape of the reference pattern 118 can vary depending on application (e.g., the size and shape of the user's hand, or the size and shape of the object to be measured). In the illustrated embodiment, the reference pattern 118 includes an elongate central portion 130 with first and second wing portions 132, 134 extending laterally therefrom. The wing portions 132, 134 can be sized and configured to wrap around the user's finger when the membrane 112 is in a deflated state, and to at least partially unroll therefrom when the membrane is in an inflated state. In some embodiments, the reference pattern 118 can have a width as measured along the measurement axis M of about 2 inches and a height as measured perpendicular to the measurement axis of about 1.5 inches.

The reference pattern 118 can be formed directly on the interior surface of the membrane 112, or can be formed on a separate substrate 136 coupled to the interior surface of the membrane. In embodiments in which the reference pattern 118 is formed directly on the interior of the membrane 112, inflation of the membrane can result in stretching or distortion of the reference pattern to a degree commensurate with the degree of inflation of the membrane. In such cases, unless the degree of membrane inflation is known and well-controlled, the stretching of the reference pattern 118 can undesirably introduce error into the measurement provided by the evaluation system 100.

Figure 5A:
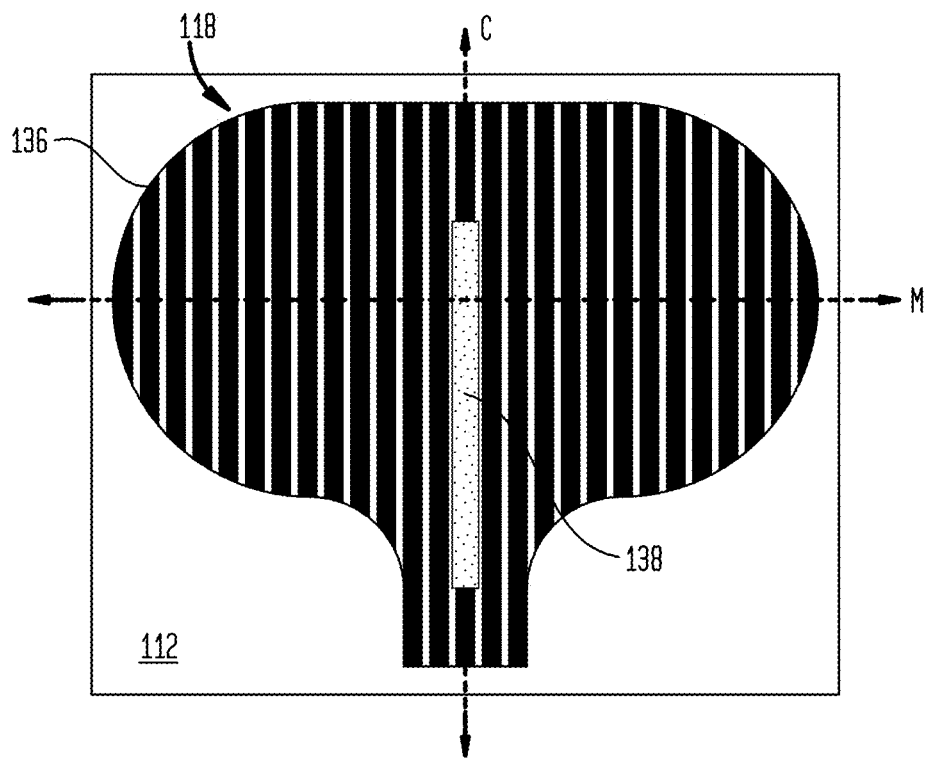
FIG. 5A is a top view of a reference pattern adhered to a membrane along a line.
Figure 5B:
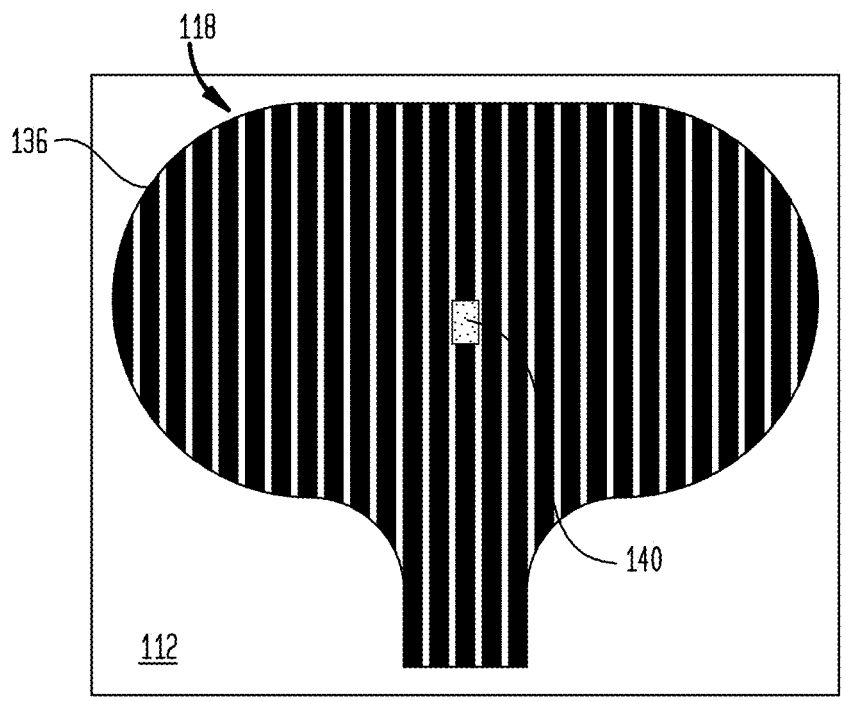
FIG. 5B is a top view of a reference pattern adhered to a membrane at a single point.
Figure 6A:
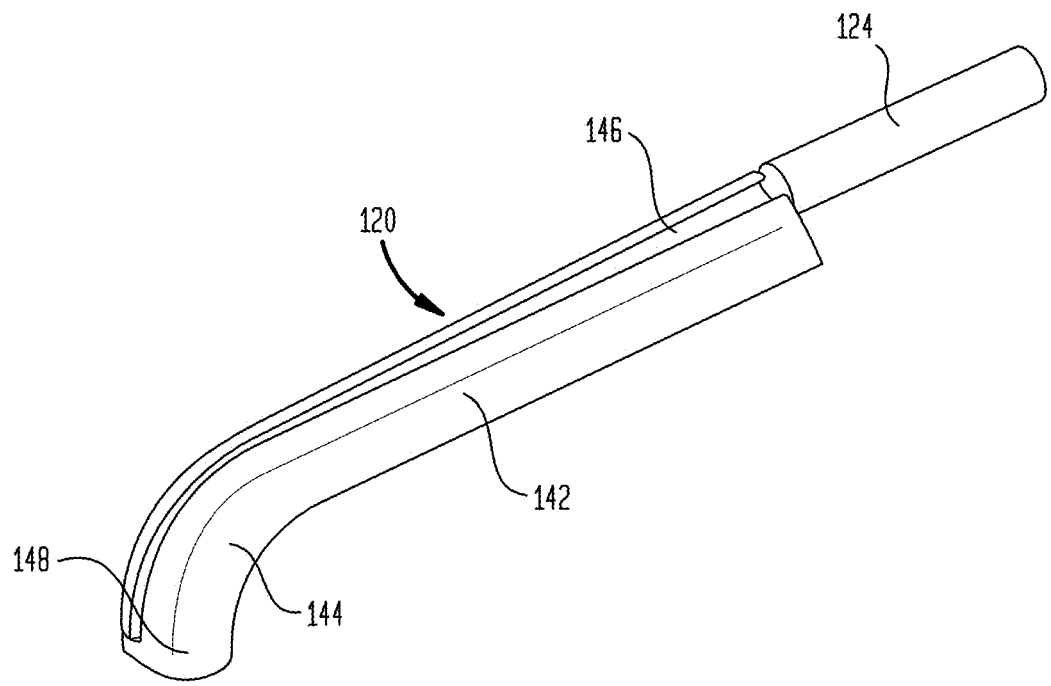
FIG. 6A is a perspective view of a finger clip.
Figure 6B:
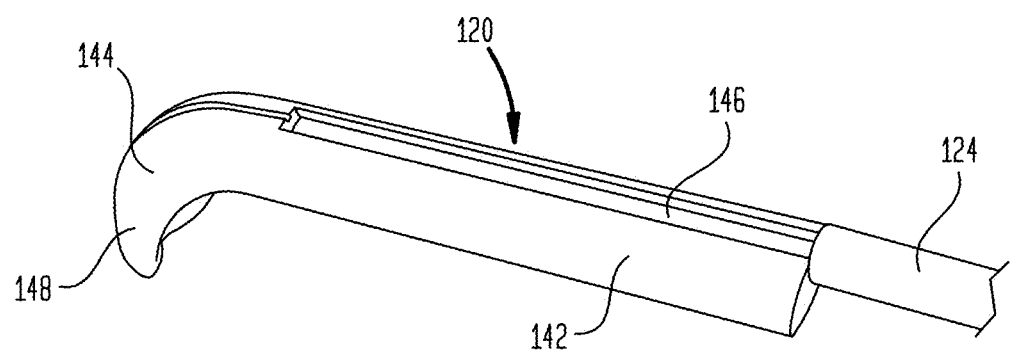
FIG. 6B is another perspective view of a finger clip.
Figure 6C:
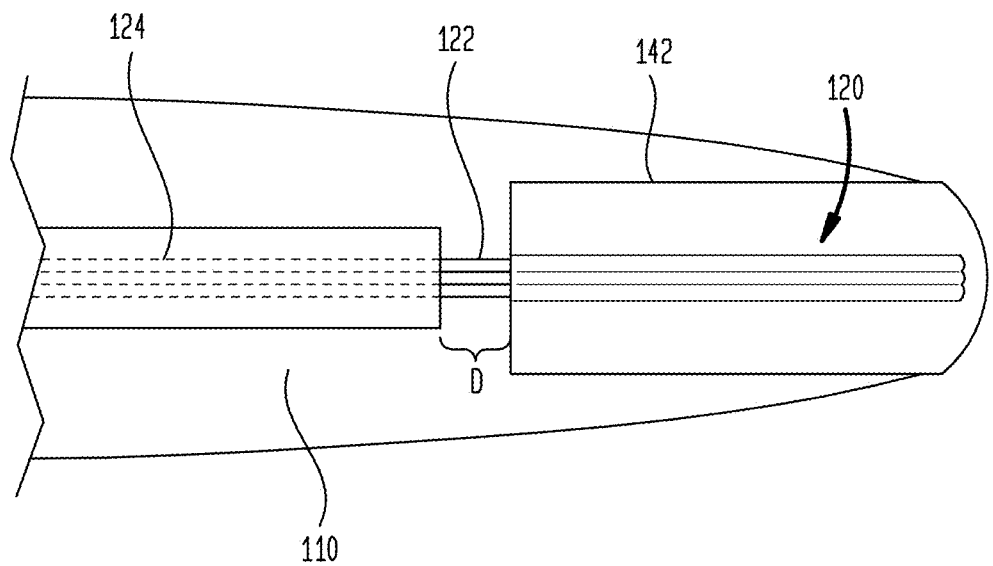
FIG. 6C is a top view of a finger clip attached to a glove.
Figure 6D:
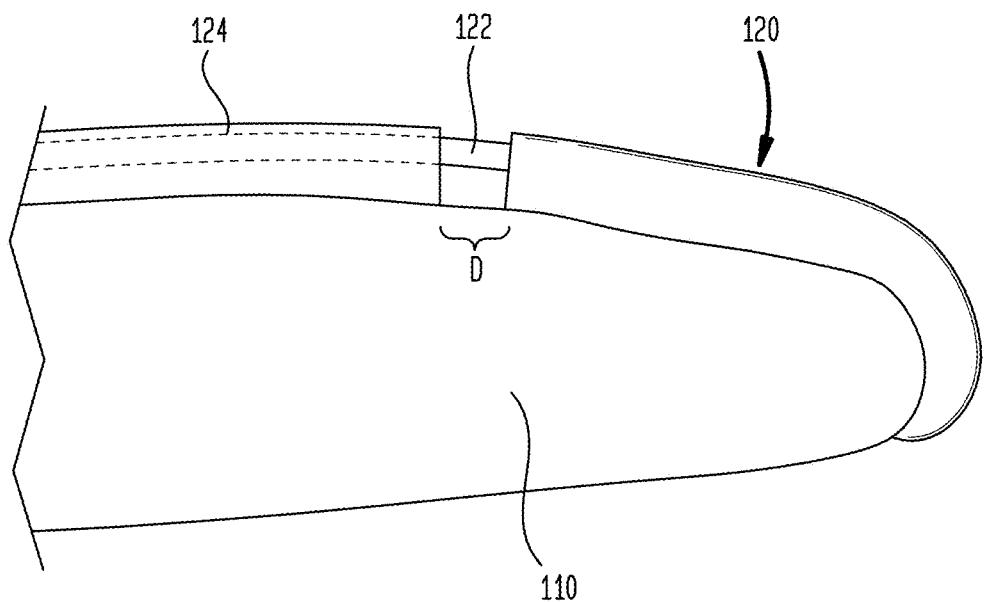
FIG. 6D is a side view of a finger clip attached to a glove.

Accordingly, in some embodiments, the reference pattern 118 can be formed on a substrate 136 that is separate from but coupled to the membrane 112 such that the dimensions of the reference pattern are not distorted by inflation or deflation of the membrane. In other words, the reference pattern 118 does not inflate or deflate or otherwise distort with the membrane 112, and instead the spacing 128 between the plurality of indicia 126, and the width of the indicia 126, can remain constant upon inflation and deflation of the membrane 112. As shown in FIGS. 5A-5B, the reference pattern 118 can be formed on a substrate 136 separate from the membrane 112. The substrate 136 can be attached to the membrane 112 using an adhesive or other attachment techniques, such as fusion bonding, hot-gas welding, vibration welding, solvent bonding, or ultrasonic welding. In the embodiment of FIG. 5A, a line 138 of adhesive is applied along a central axis C of the substrate 136 (e.g., an axis that is perpendicular to the measurement axis M). It will be appreciated that, due to this adhesive pattern, any stretching of the substrate 136 as the membrane 112 is inflated or deflated will only stretch the reference pattern 118 along the central axis C, and not along the measurement axis M. Accordingly, the spacing 128 between the measurement lines 126 can remain constant during inflation and deflation, as can the width of the lines 126. In the embodiment of FIG. 5B, the substrate 136 is adhered to the membrane 112 at a single discrete point 140 (e.g., at a center point of the substrate 136). The size and location of the adhesion point 140 can be selected to balance resistance to inflation-related distortion of the reference pattern 118 with resistance to inadvertent rotation of the substrate 136 relative to the membrane 112.

The reference pattern 118 can be formed on the substrate 136 or membrane 112 in any of a variety of ways. In some embodiments, the dark regions 126 of the reference pattern 118 are printed on the substrate 136 or membrane 112, for example using dark-colored ink, dye, or paint. The light regions 128 of the reference pattern 118 can be formed by untreated portions of the substrate 136 or membrane 112, in which case they can have the same color, transparency, translucency, etc. as the underlying material. The light regions 128 can also be printed on the membrane 112 or substrate 136, for example using light-colored ink, dye, or paint. In embodiments in which the light regions 128 are formed by untreated portions of the substrate 136 or membrane 112, light can reflect off of the substrate or membrane itself, or off of the tissue or other object underlying the substrate or membrane.

Any of a variety of suitable materials can be used for the substrate 136, including plastics such as polyethylene. In some embodiments, the substrate 136 can have a thickness between about 0.5 mils and about 6.0 mils. In some embodiments, the substrate 136 can have a thickness of about 2 mils.

Finger Clip and Inflation Tube

FIGS. 6A-6D illustrate an exemplary embodiment of the finger clip 120 and the inflation tube 124. The finger clip can be configured to hold one or more optical fibers 122 in a fixed position relative to the user's finger, in a fixed position relative to one another, and/or in a fixed alignment relative to the reference pattern 118.

As shown, the finger clip 120 can include an elongate body 142 configured to substantially conform to the dorsal surface of a user's finger (or a user's gloved finger as the case may be). The elongate body 142 can include a curved or bent distal portion 144 configured to substantially conform to the distal tip of the user's finger. Thus, the finger clip 120 can be attached to the digit extension 114 of the glove 110 such that it extends along a dorsal surface of the digit extension and down across a distal tip of the digit extension. It will be appreciated that the finger clip 120 can be adhered or otherwise attached to the glove 110, such that the finger clip remains in a fixed position relative to a user's finger when the glove is worn by the user.

The finger clip 120 can include one or more paths through which one or more optical fibers 122 can be routed. For example, the finger clip 120 can include an open channel 146 formed in its dorsal surface. The finger clip 120 can also include a tunnel 148 formed in at least a portion of the curved distal part 144 of the finger clip, extending substantially perpendicular to the dorsal surface of the finger clip, from the open channel 146 to an opening 150 (see FIGS. 7A-7B) defined by the terminal distal end of the tunnel 148. While an open channel 146 in combination with a closed tunnel 148 is shown, it will be appreciated that the optical fiber path through the finger clip 120 can also be open along its entire length, closed along its entire length, or can include any combination of closed and open portions. The finger clip 120 can be formed from a variety of materials and using a variety of techniques. In some embodiments, the finger clip 120 can be injection molded from a soft durometer urethane (e.g., a 60 durometer urethane). The length of the finger clip 120 can be chosen such that, when the distal tip of the finger clip is placed in proximity to the rectal wall over the prostate, the proximal tip of the finger clip is fully disposed within the rectum and the inflation tube 124 extends distally beyond the anal ring. This can advantageously prevent the anal ring from pinching the membrane 112 between the distal end of the inflation tube 124 and the proximal end of the finger clip 120, which could prevent full inflation of the membrane. In some embodiments, the finger clip 120 can have a length of about 4 cm.

The finger clip 120 can be disposed entirely within the closed volume 116 defined between the membrane 112 and the glove 110, such that its proximal end is adjacent to the distal outlet of the inflation tube 124. The inflation tube 124 can terminate a distance D from the proximal end of the finger clip 120, such that inflation media directed through the inflation tube 124 can exit the tube at its distal end and enter the closed volume 116 without being obstructed by the finger clip 120. The inflation tube 124 can be formed by a length of tubing, such as Tygon ND Series medical tubing or S-50-HL Tygon tubing available from Saint-Gobain S.A. of France. In an exemplary embodiment, the inflation tube 124 has an inside diameter of 3/32 inches and an outside diameter of 5/32 inches. The length of the inflation tube 124 can be selected based on a variety of factors, including user preference and the typical distance between the controller 106 and the patient. In an exemplary embodiment, the inflation tube 124 has a length of about 1 meter. The inflation tube 124 can be configured to deliver an inflation medium to the closed volume 116, or to extract an inflation medium from the closed volume. Exemplary inflation media include air, carbon dioxide, saline, and water. In some embodiments, the finger clip 120 can be omitted and the fibers 122 and/or the inflation tube 124 can instead be attached directly to the glove 110, for example using an adhesive. The inflation tube 124 can have a circular cross-section, a rectangular-cross section, or any other cross-section that defines an inflation lumen through which inflation media can be conveyed.

Fibers

The measurement assembly 104 can include one or more optical fibers 122 configured to transmit light generated by a light source to the reference pattern 118, and/or to transmit light reflected from the reference pattern to an optical sensor. The optical fibers 122 can extend through the inflation tube 124 and can be routed through the fiber path defined by the finger clip 120. The optical fibers 122 can be secured within the fiber path, for example using a friction fit or a suitable adhesive. The fibers 122 can terminate a distance from the distal opening 150 in the finger clip tunnel 148, such that a desired spacing is maintained between the end of the fiber and the reference pattern 118 even when the tip of the finger clip 120 is in direct contact with the reference pattern. In some embodiments, the fibers 122 can terminate between about 0.25 mm and about 0.5 mm from the distal opening 150 of the finger clip tunnel 148. The fibers 122 can thus be positioned within the finger clip 120 such that optical windows formed in the terminal distal ends of the fibers are aimed in a direction perpendicular to a dorsal surface of a user's finger when the finger clip is attached to the user's finger.

Figure 7A:
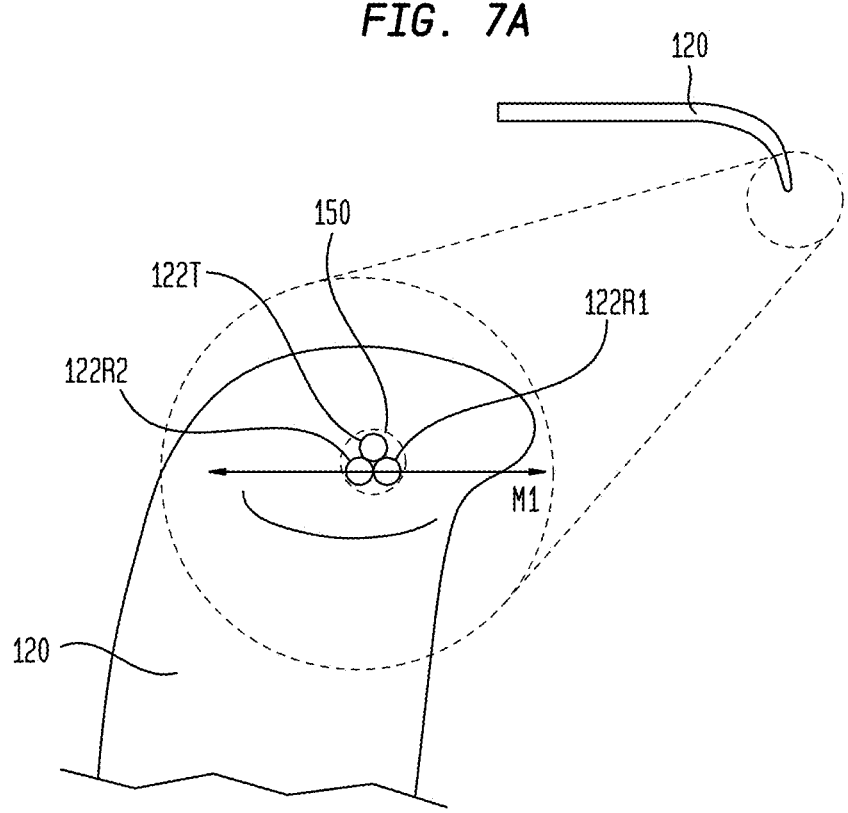
FIG. 7A is a schematic end view of a finger clip with optical fibers arranged in a triangle pattern.
Figure 7B:
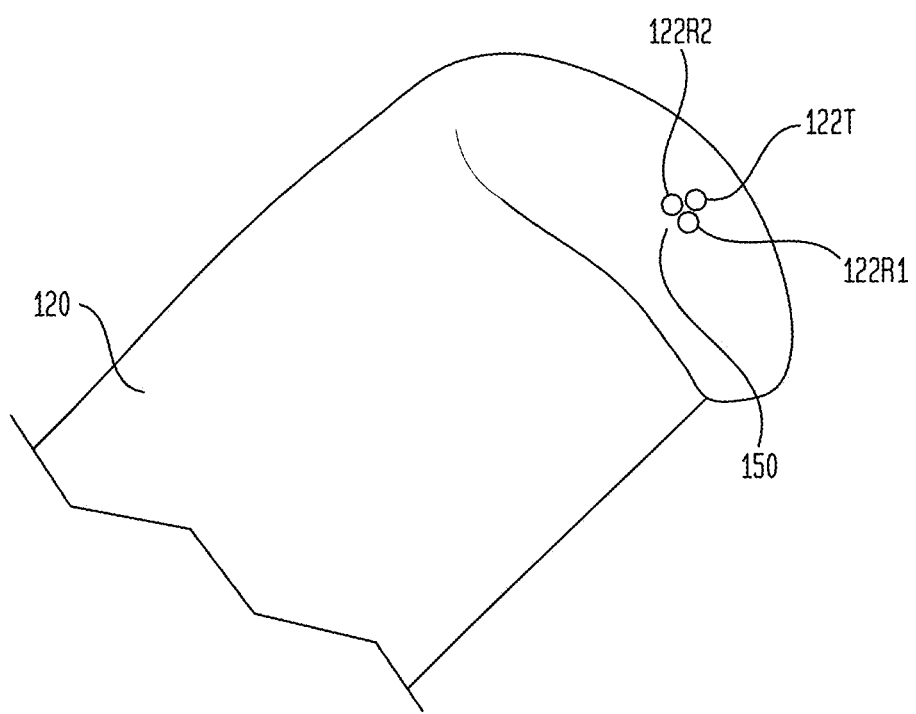
FIG. 7B is an end view of a finger clip with optical fibers arranged in a triangle pattern.

In some embodiments, a single fiber 122 can be used both to transmit light from the light source to the reference pattern 118 and to transmit light reflected from the reference pattern to the optical sensor. In further embodiments, the measurement assembly 104 can include a transmitting optical fiber for directing light from the light source to the reference pattern 118 and a receiving optical fiber for directing light reflected from the reference pattern to the optical sensor. In still further embodiments, as shown in FIGS. 7A-7C, the system can include a transmitting fiber 122T and first and second receiver fibers 122R1, 122R2, each of the receiver fibers being configured to transmit light reflected from the reference pattern 118 to one or more optical sensors. The optical fibers 122 can be coupled directly to the light source or optical sensors, or can be coupled thereto via one or more intermediate fibers, for example using a connector system as described below.

Each of the optical fibers 122 can be jacketed or unjacketed, and can include one or more input or output windows through which light can pass. For example, the transmitting optical fiber 122T can include an input window defined by its terminal proximal end and an output window defined by its terminal distal end. Similarly, the receiver fiber(s) 122R1, 122R2 can include an input window defined by their terminal distal end and an output window defined by their terminal proximal end. The fibers 122 can be configured to transmit infrared, near-infrared, visible, or other any other detectable spectra of light. Exemplary fibers include unjacketed CK-20 ESKA plastic optical fibers having a diameter of 0.5 mm, available from Mitsubishi International Corporation of New York, N.Y. The fibers 122 can have a length that is slightly longer than that of the inflation tube 124 to facilitate routing of the fibers through the finger clip 120 and/or a connector assembly coupled to the inflation tube.

As shown in FIGS. 7A-7C, the fibers 122 can be positioned in the finger clip 120 so as to improve the measurement accuracy and error detection capabilities of the system 100. In particular, the transmitting fiber 122T and the first and second receiver fibers 122R1, 122R2 can be positioned in the finger clip 120 such that the input windows of the first and second receiver fibers are arranged in a line M1 that is substantially parallel to the measurement axis M of the reference pattern 118 when the system 100 is assembled. The transmitting fiber 122T can be positioned above or below the receiver fibers 122R1, 122R2 such that the output window of the transmitting fiber and the input windows of the first and second receiver fibers are arranged in a triangle or delta pattern.

During operation, as the user swipes the finger clip 120 across the reference pattern 118, the offset between the receiver fibers 122R1, 122R2 along the measurement axis M can cause one of the receiver fibers to transmit reflected light before the reflected light can be transmitted by the other receiver fiber. Accordingly, the optical sensor output corresponding to the first fiber will toggle before the optical sensor output of the second fiber.

Figure 8A:
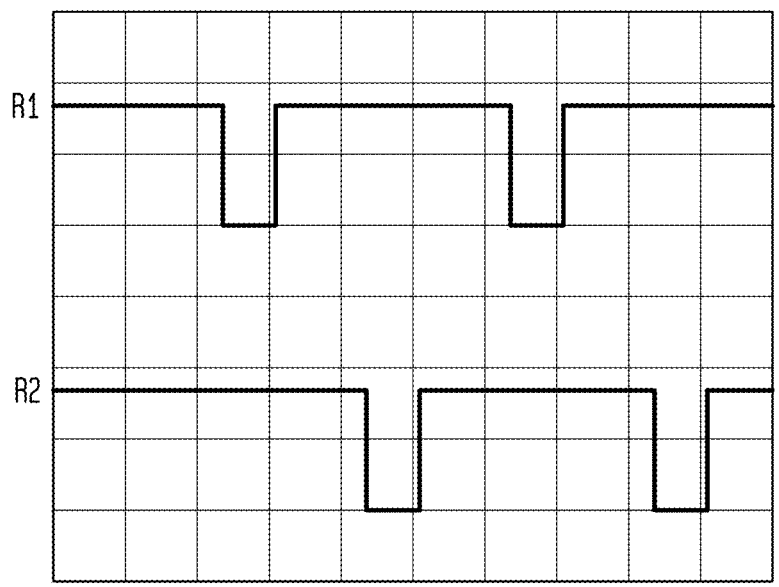
FIG. 8A is a plot of optical sensor output signals as a function of time when optical fibers are moved in a first direction relative to a reference pattern.
Figure 8B:
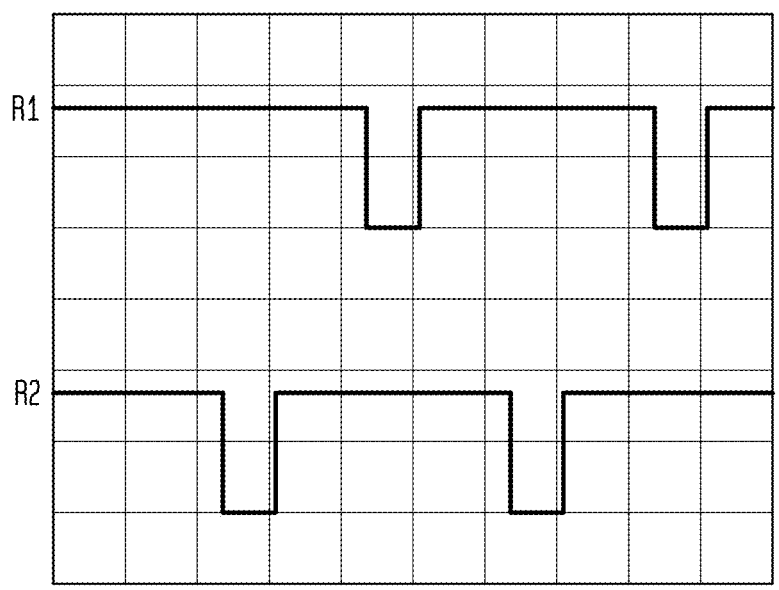
FIG. 8B is a plot of optical sensor output signals as a function of time when optical fibers are moved in a second direction, opposite to the first direction, relative to a reference pattern.

FIGS. 8A and 8B are plots of the output of an optical sensor R1 coupled to the first receiver fiber 122R1 and the output of an optical sensor R2 coupled to the second receiver fiber 122R2 as a function of time. As shown in FIG. 8A, when the finger clip 120 is moved in a first direction along the measurement axis M, the sensor R1 for the first receiver fiber 122R1 detects a boundary crossing slightly before the boundary crossing is detected by the sensor R2 for the second receiver fiber 122R2. As shown in FIG. 8B, when the finger clip 120 is moved in a second direction along the measurement axis M, opposite to the first direction, the sensor R2 for the second receiver fiber 122R2 detects a boundary crossing slightly before the boundary crossing is detected by the sensor R1 for the first receiver fiber 122R1. Accordingly, by comparing the light received by the first receiver fiber 122R1 in time relation to the light received by the second receiver fiber 122R2, the direction of finger clip 120 movement relative to the reference pattern 118 can be determined. As discussed further below, the controller 106 can be configured to detect that an error has occurred when a change in direction is detected, or to compensate for the change in direction.

Controller

Figure 9A:
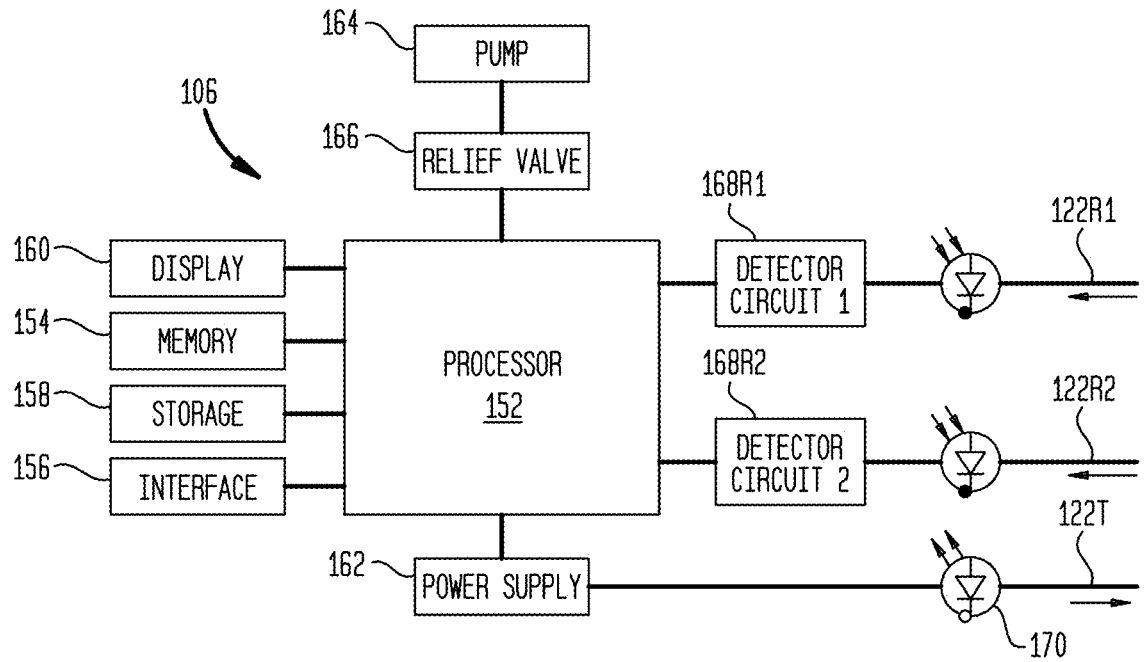
FIG. 9A is a schematic diagram of the physical components of a controller.

FIG. 9 illustrates a block diagram of the physical components of an exemplary embodiment of the controller 106. Although an exemplary controller 106 is depicted and described herein, it will be appreciated that this is for sake of generality and convenience. In other embodiments, the controller 106 may differ in architecture and operation from that shown and described here.

The illustrated controller 106 includes a processor 152 which controls the operation of the controller 106, for example by executing embedded software, operating systems, device drivers, application programs, and so forth. The processor 152 can include any type of microprocessor or central processing unit (CPU), including programmable general-purpose or special-purpose processors and/or any of a variety of proprietary or commercially-available single or multi-processor systems, including 32-bit PIC Peripheral Interface Controllers or 16-bit dsPIC digital signal Peripheral Interface Controllers available from Microchip Technology Incorporated of Chandler, Ariz. As used herein, the term processor can refer to microprocessors, microcontrollers, ASICs, FPGAs, processors that read and interpret program instructions from internal or external memory or registers, and so forth. The controller 106 also includes a memory 154, which provides temporary or permanent storage for code to be executed by the processor 152 or for data that is processed by the processor. The memory 154 can include read-only memory (ROM), flash memory, one or more varieties of random access memory (RAM), and/or a combination of memory technologies. The various components of the controller 106 can be interconnected via any one or more separate traces, physical busses, communication lines, etc.

The controller 106 can also include an interface 156, such as a communication interface or an I/O interface. A communication interface can enable the controller 106 to communicate with remote devices (e.g., other controllers or computer systems) over a network or communications bus (e.g., a universal serial bus). An I/O interface can facilitate communication between one or more input devices, one or more output devices, and the various other components of the controller 106. Exemplary input devices include touch screens, mechanical buttons, keyboards, and pointing devices. The controller can also include a storage device 158, which can include any conventional medium for storing data in a non-volatile and/or non-transient manner. The storage device 158 can thus hold data and/or instructions in a persistent state (i.e., the value is retained despite interruption of power to the controller 106). The storage device 158 can include one or more hard disk drives, flash drives, USB drives, optical drives, various media disks or cards, and/or any combination thereof and can be directly connected to the other components of the controller 106 or remotely connected thereto, such as through the communication interface. The controller 106 can also include a display 160, and can generate images to be displayed thereon. In some embodiments, the display 160 can be a vacuum fluorescent display (VFD), an organic light-emitting diode (OLED) display, or a liquid crystal display (LCD).

The controller 106 can also include a power supply 162 and appropriate regulating and conditioning circuitry. Exemplary power supplies include batteries, such as polymer lithium ion batteries, or adapters for coupling the controller 106 to a DC or AC power source (e.g., a USB adapter or a wall adapter). The controller 106 can also include an inflation system 164, such as an electromechanical pump controlled by the processor 152. Other inflation systems can also be employed, such as a stored volume of compressed fluid (e.g., air or carbon dioxide) or a manual pump (e.g., a sphygmomanometer bulb). A pressure relief valve 166 or other safety device can also be provided to prevent over-inflation of the membrane 112 and/or to deflate the membrane when an evaluation is complete. In some embodiments, the pressure relief valve 166 can be configured to fail into the open position, such that pressure is released from the membrane 112 in the event of a power loss or other system malfunction. The inflation system 164 can be configured to supply an inflation medium through the inflation tube 124 and into the closed volume 116. Any of a variety of inflation media can be used, including air, carbon dioxide, saline, water, and the like. In some embodiments, the inflation system 164 can be configured to inflate the membrane 112 to an inflation pressure of 1.5 psi, and the pressure relief valve 166 can be configured to release pressure if and when it exceeds 2.0 psi. The inflation system 164 can also be configured to supply a fixed volume of an inflation medium to the membrane 112, e.g., about 25 mL of air.

The controller 106 can also include an optical system that includes a first detector circuit 168R1 for receiving light transmitted through the first receiver fiber 122R1, a second detector circuit 168R2 for receiving light transmitted through the second receiver fiber 122R2, and a light source 170 for producing light to be transmitted through the transmitting fiber 122T. In some embodiments, the detector circuits 168 can include a photo detector that is optically coupled to a fiber 122 and electrically coupled to the processor 152. Exemplary photo detectors include CMOS image sensors, charge-coupled devices, photodiodes, photoresistors, and phototransistors (e.g., photodarlington detectors). The photo detector can provide an electrical output signal to the processor 152 based on light that is received by the photo detector. The light source 170 can be or can include any of a variety of devices configured to produce light, including LEDs and incandescent bulbs. In some embodiments, the light source 170 can include an infrared LED.

Figure 9B:
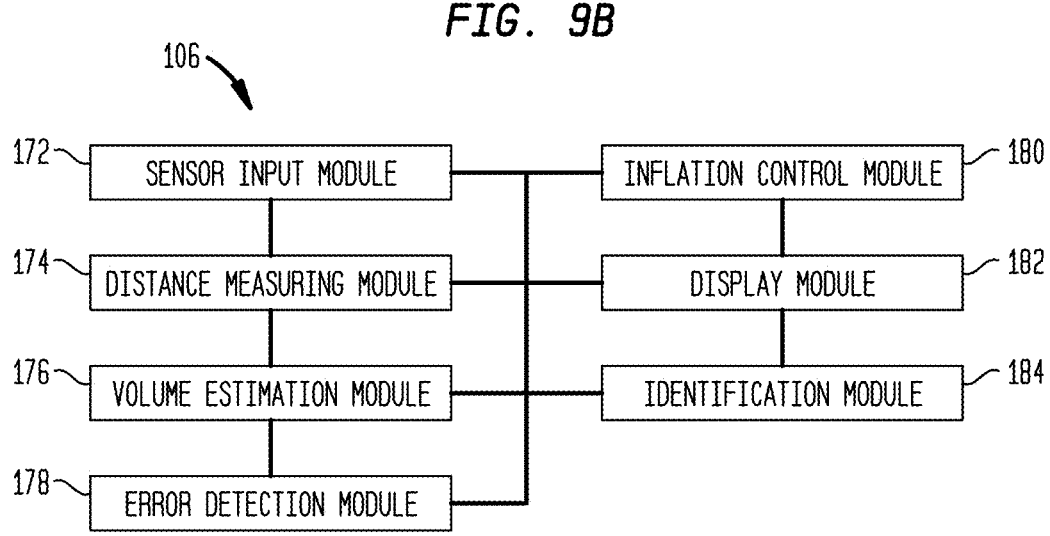
FIG. 9B is a schematic diagram of the logical components of a controller.

The various functions performed by the controller 106 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an embedded software package, an operating system, a device driver, a standalone application, and/or combinations thereof). In addition, software embodying one or more modules can be stored as an executable program on one or more non-transitory computer-readable storage mediums. Functions disclosed herein as being performed by a particular module can also be performed by any other module or combination of modules, and the controller can include fewer or more modules than what is shown and described herein. FIG. 9B is a schematic diagram of the modules of one exemplary embodiment of the controller 106.

As shown in FIG. 9B, the controller 106 can include a sensor input module 172 configured to receive information indicative of light reflected from the reference pattern 118 as the optical fiber(s) 122 are moved across the reference pattern during an examination. The sensor input module 172 can read and interpret photo detector output signals supplied from the photo detectors 168 to the processor 152, e.g., via a general purpose input/output pin of the processor. The sensor input module 172 can optionally perform various processing on the photo detector output signal, such as debouncing, analog-to-digital conversion, filtering, and so forth.

The controller 106 can also include a distance measuring module 174 configured to convert the information received by the sensor input module 172 into a measurement of the object being evaluated (e.g., a palpable surface width $PS_W$ in the case of a prostate). For example, when a start instruction is issued (e.g., in response to the user's pressing of a "start measurement" button or equivalent), the distance measuring module 174 can begin counting the number of signal pulses received from the photo detectors 168. When an end instruction is issued (e.g., in response to the user's pressing of an "end measurement" button or after a predetermined time has elapsed without a detected pulse), the distance measuring module 174 can multiply the number of pulses counted by the width of the indicia 126 and spaces 128 formed on the reference pattern 118. This width can be pre-stored as a constant value in the memory 154 of the controller 106, can be manually input by the user via the controller's user interface, or can be read from a passive or active memory chip disposed in the measurement assembly 104.

Figure 10:
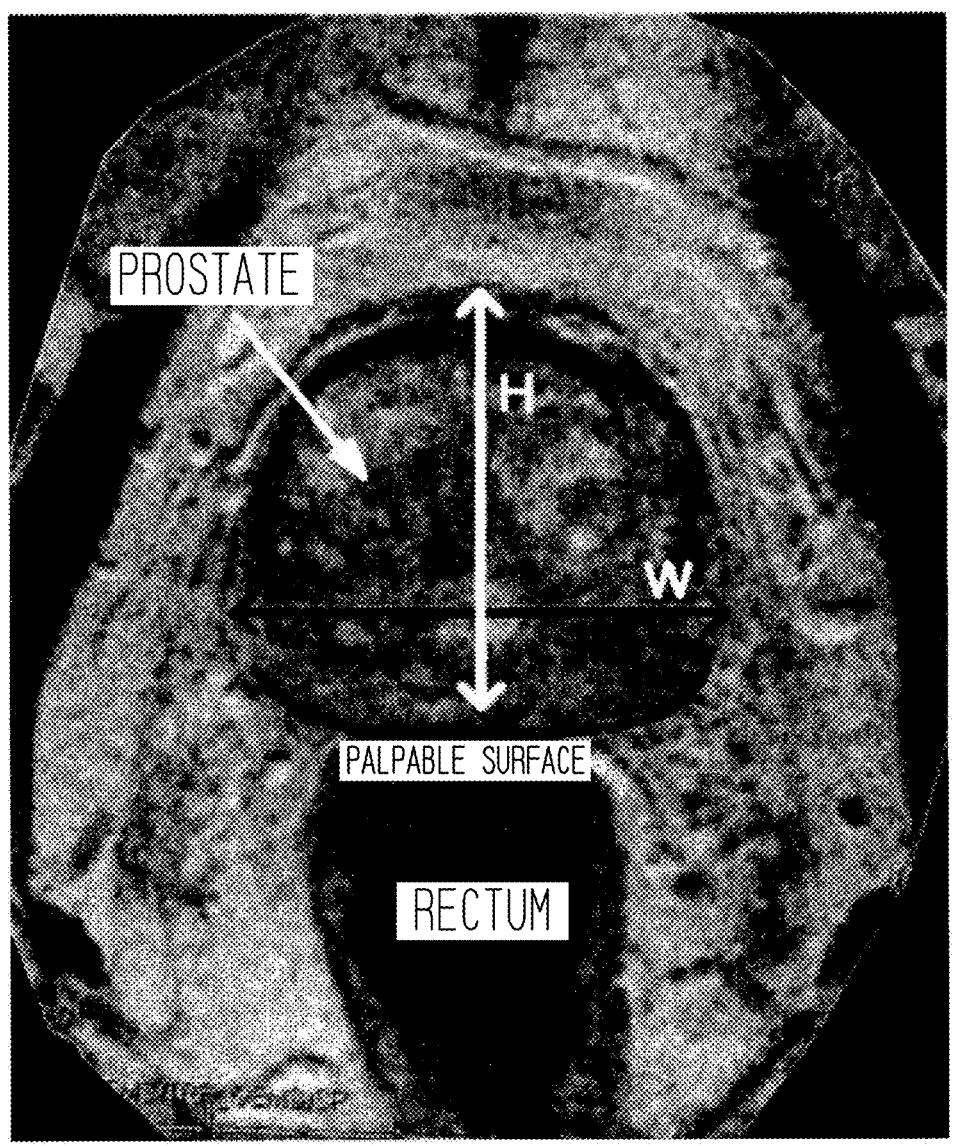
FIG. 10 is a magnetic resonance image of a prostate.

The controller 106 can also include a volume estimation module 176 configured to estimate a volume or other attribute of the object being measured based on one or more measurements obtained by the distance measuring module 174. For example, the volume estimation module 176 can be configured to calculate or estimate the volume (V) of a prostate based on the palpable surface width ($PS_W$) of the prostate as obtained by the distance measuring module 174. The palpable surface of a prostate is illustrated in the magnetic resonance image shown in FIG. 10. The volume can be calculated as:

$$V = PS_W^3 \odot k$$

where k is a constant. Any of a variety of values can be used for the constant k to calculate the volume. In some embodiments, k is between about 0.01 and about 1.00. In some embodiments, k is between about 0.35 and about 0.45. In some embodiments, k is about 0.3926991. The volume estimation module 176 can also use other techniques to estimate the volume (V) based on the measured palpable surface width $PS_W$. For example, the volume estimation module 176 can reference a lookup table stored in the memory 154 to determine a volume associated with a particular palpable surface width. The volume estimation module 176 can also estimate other dimensions of the prostate based on the palpable surface width (e.g., a height (H), a width (W) and a depth (D)), and calculate the prostate volume using the estimated dimensions. For example, the volume (V) of the prostate can be calculated as:

$$V = H \odot W \odot D \odot \pi/6$$

or as:

$$V = H^2 \odot W \odot \pi/6$$

Referring again to FIG. 9B, the controller 106 can also include an error detection module 178 configured to detect when a measurement error may have occurred. The error detection module 178 can compare the photo detector output corresponding to the first receiver fiber 122R1 to the photo detector output corresponding to the second receiver fiber 122R2 (e.g., as described above with respect to FIGS. 8A and 8B), to determine the order in which the first and second receiver fibers encounter a marking or border crossing on the reference pattern 118. If the error detection module 178 detects that this order changes during a measurement (e.g., between the time when a start instruction and an end instruction are issued), the error detection module can flag that an error has occurred. For example, the error detection module 178 can cause an error LED to be illuminated, an audible alert to be sounded, and/or a visible message to be shown on the display 160. In some embodiments, the error detection module 178 can be configured to compensate for directional changes by decrementing the indicia count when it is detected that the user is moving the optical fibers 122 backwards along the reference pattern 118.

The controller 106 can also include an inflation control module 180 configured to actuate the inflation system 164. When an "inflate" instruction is issued (e.g., when the user pushes an inflate button or a start measurement button on the controller housing or on a touch screen display), the inflation control module 180 can cause power to be supplied to an electromechanical pump to begin pumping an inflation medium into the closed volume 116, or cause an electronically-actuated valve to open such that inflation media stored under pressure is placed in fluid communication with the closed volume via the inflation tube 124. In some embodiments, the inflation control module 180 can be configured to cut off power to the pump or to close a valve when a pressure sensor indicates that the pressure in the system has reached a predetermined threshold amount, thereby preventing over-inflation of the membrane.

The controller 106 can also include a display module 182 configured to display various information to the user on the display 160, such as menus, buttons, instructions, and other user interface elements. The display module 162 can also be configured to display instructions, warnings, errors, measurements, and calculations. For example, the display module 182 can be configured to display the palpable surface width ($PS_W$) and volume (V) of a prostate after a measurement procedure is completed on the prostate.

The controller 106 can also include an identification module 184 configured to determine whether the measurement assembly 104 is an authenticated measurement assembly. In some embodiments, the measurement assembly 104 can include an RFID tag, micro bar code, or other embedded identification information. The identification module 184 can be configured to read this identification information and compare it to a database of measurement assemblies. The database can be stored in the controller 106 or can be accessible via a network, and can indicate whether or not a particular measurement assembly 104 is authenticated. If the measurement assembly 104 is determined not to be authenticated, the identification module 184 can indicate as much to the user and can prevent the measurement from proceeding. If the measurement assembly 104 is determined to be authenticated, the identification module 184 can permit the measurement to proceed. When a measurement session is completed, the identification module 184 can be configured to create or mark an entry in the database indicating that the measurement assembly 104 used during the session is no longer authenticated, thereby preventing the measurement assembly 104 from being reused.

Connector System

As noted above, the system 100 can include one or more multiplex connector systems for coupling the measurement assembly 104 to the controller 106. FIGS. 11A-11H illustrate an exemplary embodiment of a connector system 200 in which a first fluid lumen and a first set of optical fibers (which can be disposed in the controller 106) can be selectively coupled to a second fluid lumen and a second set of optical fibers (which can be disposed in the measurement assembly 104). The illustrated connector system 200 can advantageously ensure proper alignment between the inflation and optical systems of the controller 106 and the measurement assembly 104. The connector system 200 can also allow the optical fibers to transition from a position outside of the inflation lumen to a position within the inflation lumen. The connector system 200 can include a first connector assembly 202A, a second connector assembly 202B, and a connector housing 204.

Figure 11B:
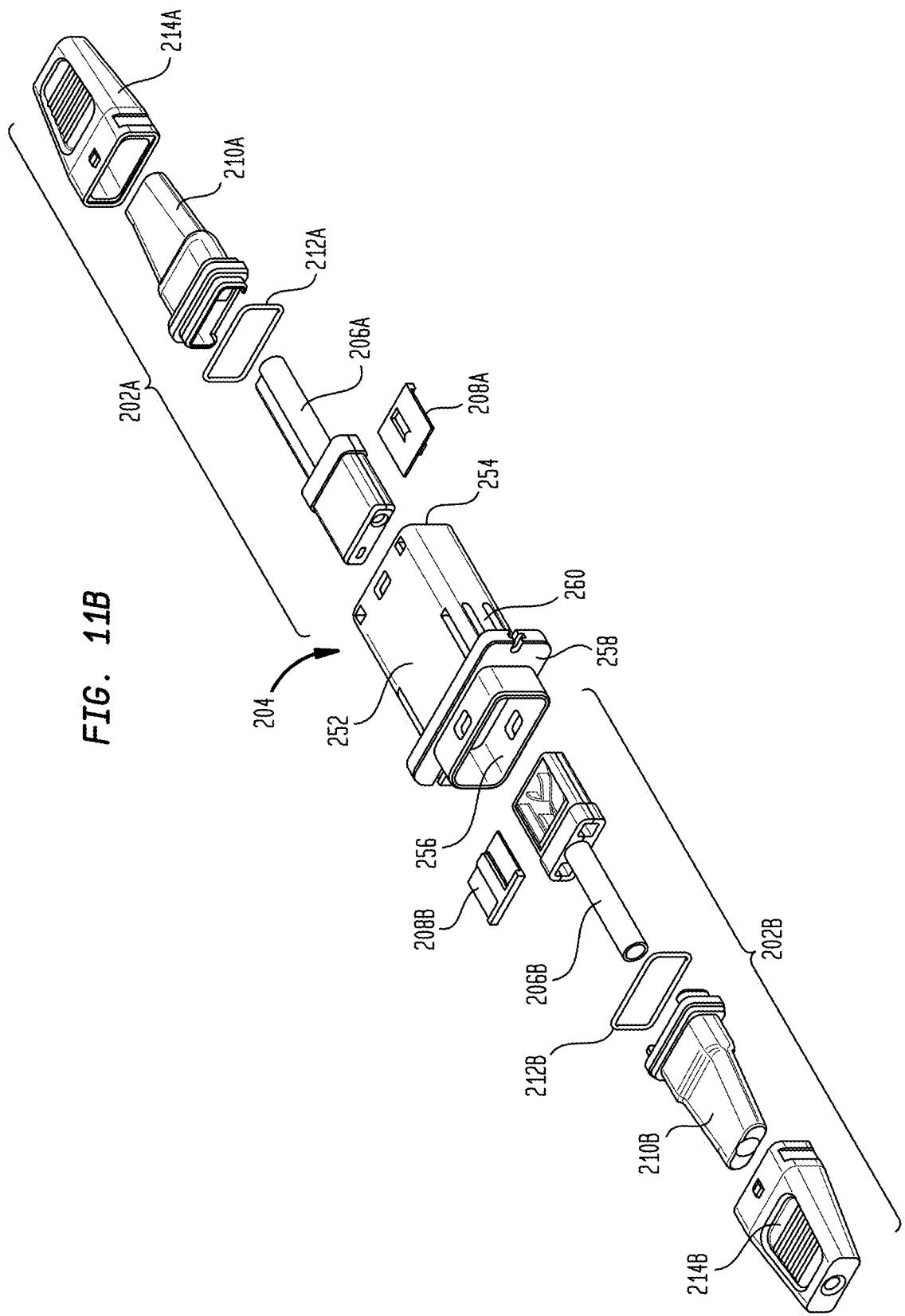
FIG. 11B is an exploded perspective view of a connector system.

As shown in FIG. 11B, the first connector assembly 202A can include a first connector body 206A, a first key plate 208A, a first internal overmold 210A, a first gasket 212A, and a first external overmold 214A.

As shown in FIG. 11C, the first connector body 206A can include a proximal extension portion 216A and a distal rectangular parallelepiped frame 218A. The proximal extension portion 216A can include a fluid passageway 220A and one or more fiber passageways 222A extending therethrough. The distal-facing surface of the frame 218A can define a first mating interface 224A configured to abut with a second mating interface 224B of the second connector body 206B, as discussed below. The frame 218A can also include internal baffles 226A that define a substantially H-shaped lumen 228A. In other words, the H-shaped lumen 228A can include first and second pathways that extend generally in the same direction with a crossover pathway joining the two together. As shown, a first leg 228A1 of the H-shaped lumen extends proximally to the fluid passageway 220A in the proximal extension portion 216A. A second leg 228A2 of the H-shaped lumen extends proximally to the fiber passageway(s) 222A in the proximal extension portion 216A. A third leg 228A3 of the H-shaped lumen extends distally to a fluid opening 230A formed in the first mating interface 224A. A fourth leg 228A4 of the H-shaped lumen extends distally to one or more fiber openings 232A formed in the first mating interface 224A.

Figure 11D:
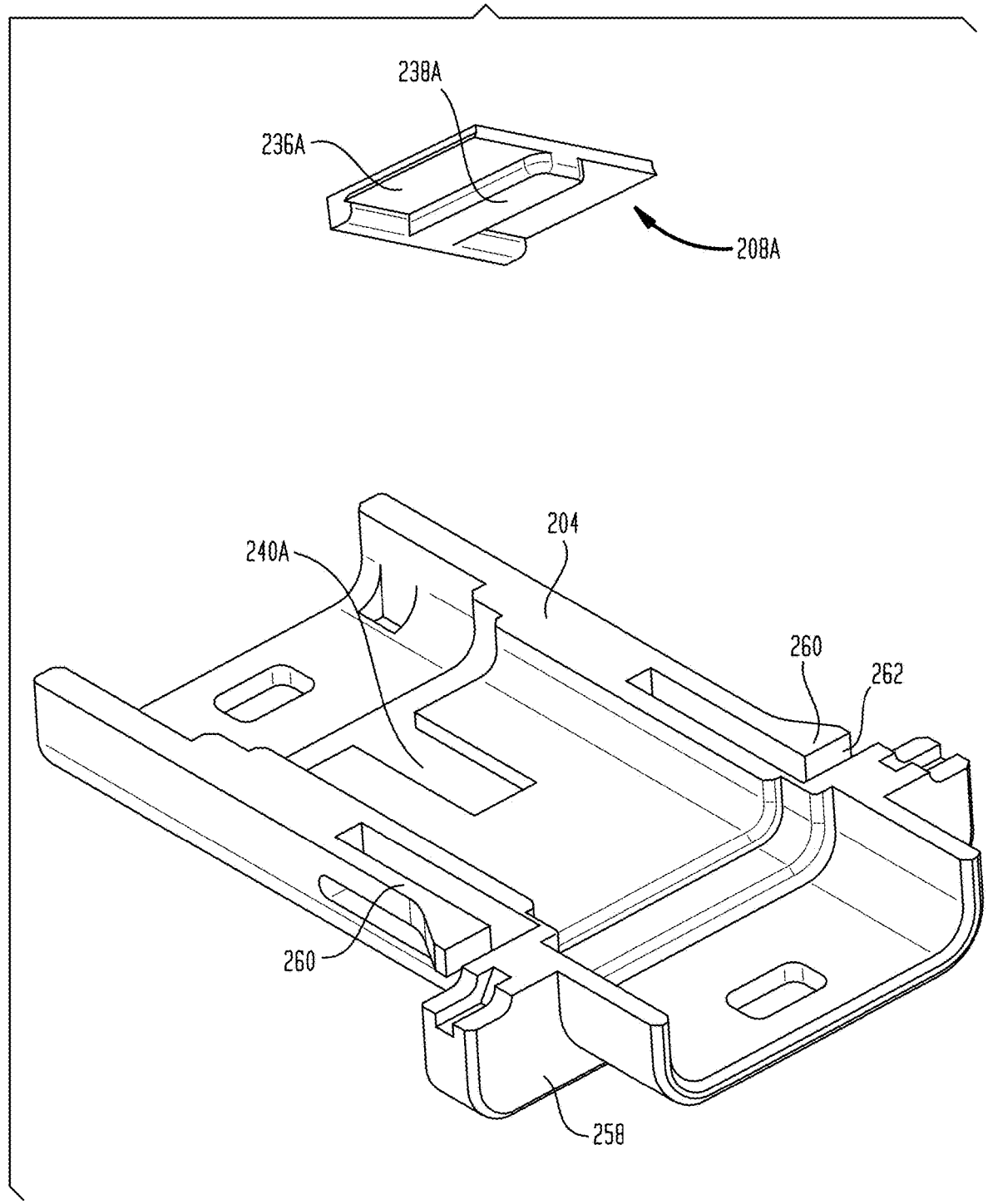
FIG. 11D is a perspective view of a first key plate and a connector housing.

The distal frame 218A can include at least one open face 234A through which the interior of the frame can be accessed. When assembled, the first key plate 208A can be glued to the frame 218A using an adhesive such that the first key plate covers the open face 234A of the frame. As shown in FIG. 11D, the first key plate 208A can include a planar base portion 236A with a raised key projection 238A configured to interface with a corresponding recess 240A in the connector housing 204. The size and shape of the projection 238A can be selected such that the first connector assembly 202A can only mate with the connector housing 204 in one orientation.

As shown in FIG. 11E, the first internal overmold 210A can be configured to slide over the proximal extension portion 216A and cover the proximal-facing surface of the distal frame 218A, or can be injection molded therearound. The first internal overmold 210A can be configured to support the proximal extension 216A and provide strain relief. The first internal overmold 210A can also include a lip 242A for forming the distal sidewall of a trough in which the first gasket 212A is seated.

The first gasket 212A can be configured to form a fluid-tight seal at the interface between the first connector assembly 202A and the connector housing 204. In some embodiments, the first gasket 212A can be a rubber O-ring.

The first external overmold 214A can be configured to slide over the first internal overmold 210A, or can be injection molded therearound, and can include a lip 244A for forming the proximal sidewall of the trough in which the first gasket 212A is seated. The first external overmold 214A can include a gripping surface 246A defined by a series of grooves or ribs, and can include raised tabs 248A and/or slots 250A configured to mate with corresponding features formed in the connector housing 204, such that the first connector assembly 202A can snap-fit into the connector housing 204.

Referring again to FIG. 11B, the second connector assembly 202B can include a second connector body 206B, a second key plate 208B, a second internal overmold 210B, a second gasket 212B, and a second external overmold 214B.

As shown in FIG. 11F, the second connector body 206B can include a distal extension portion 216B and a proximal rectangular parallelepiped frame 218B. The distal extension portion 216B can include a fluid passageway 220B extending therethrough. The proximal-facing surface of the frame 218B can define a second mating interface 224B configured to abut with the first mating interface 224A of the first connector body 206A, as discussed below. The frame 218B can also include internal baffles 226B that define a substantially H-shaped lumen 228B. In other words, the H-shaped lumen 228B can include first and second pathways that extend generally in the same direction with a crossover pathway joining the two together. As shown, a first leg 228B1 of the H-shaped lumen 228B extends distally to the fluid passageway 220B in the distal extension portion 216B. A second leg 228B2 of the H-shaped lumen 228B extends distally to a closed-off termination 252B formed by the wall of the frame 218B. A third leg 228B3 of the H-shaped lumen 228B extends proximally to a fluid opening 230B formed in the second mating interface 224B. A fourth leg 228B4 of the H-shaped lumen 228B extends proximally to one or more fiber openings 232B formed in the second mating interface 224B.

Figure 11G:
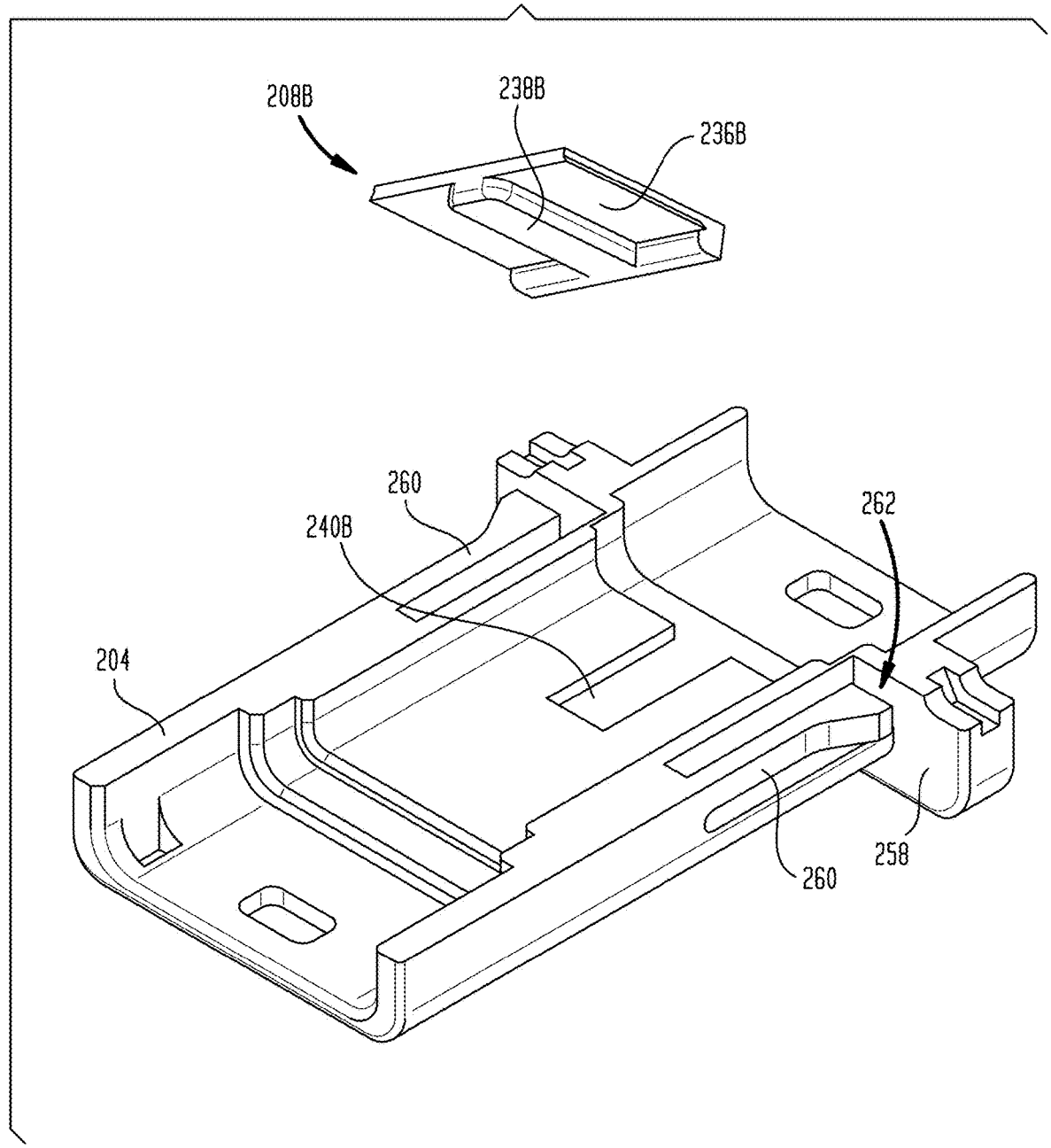
FIG. 11G is a perspective view of a second key plate and a connector housing.

The proximal frame 218B can include at least one open face 234B through which the interior of the frame can be accessed. When assembled, the second key plate 208B can be glued to the frame 218B using an adhesive such that the second key plate covers the open face 234B of the frame. As shown in FIG. 11G, the second key plate 208B can include a planar base portion 236B with a raised key projection 238B configured to interface with a corresponding recess 240B in the connector housing 204. The size and shape of the projection 238B can be selected such that the second connector assembly 202B can only mate with the connector housing 204 in one orientation. The second key plate 208B, which can form part of a disposable portion of the system 100, can include an RFID tag or other identifier which can be read by the identification module 184 as discussed above. In particular, the second key plate 208B can be injection molded around an RFID tag. It will be appreciated that the RFID tag can also be placed in any of a variety of other places in the disposable portion of the system 100, such as in the glove 110, the membrane 112, or the disposable portion's packaging.

Referring again to FIG. 11E, the second internal overmold 210B can be configured to slide over the distal extension portion 216B and cover the distal-facing surface of the proximal frame 218B, or can be injection molded therearound. The second internal overmold 210B can be configured to support the distal extension 216B and provide strain relief. The second internal overmold 210B can include a lip 242B for forming the proximal sidewall of a trough in which the second gasket 212B is seated.

The second gasket 212B can be configured to form a fluid-tight seal at the interface between the second connector assembly 202B and the connector housing 204. In some embodiments, the second gasket 212B can be a rubber O-ring.

The second external overmold 214B can be configured to slide over the second internal overmold 210B, or can be injection molded therearound, and can include a lip 244B for forming the distal sidewall of the trough in which the second gasket 212B is seated. The second external overmold 214B can include a gripping surface 246B defined by a series of grooves or ribs, and can include raised tabs 248B and/or slots 250B configured to mate with corresponding features formed in the connector housing 204, such that the second connector assembly 202B can snap-fit into the connector housing 204.

As shown in FIG. 11B, the connector housing can include a rectangular parallelepiped frame 252 with a proximal opening 254 for receiving the first connector assembly 202A and a distal opening 256 for receiving the second connector assembly 202B. The housing 204 can include key slots 240A, 240B for receiving the first and second key plates 208A, 208B, respectively, as shown in FIGS. 11D and 11G. The housing 204 can also include a mating flange 258 and spring arms 260 that together define a channel 262 in which the chassis of the controller 106 can be received. In particular, as the connector housing 204 is inserted through an opening in the controller chassis 264 during system assembly, the chassis wall 266 causes the spring arms 260 to deflect inwardly towards the housing 204. As the housing 204 is advanced further through the opening, the spring arms 260 surpass the chassis wall 266 and return outwardly away from the housing 204 to lock the chassis wall 266 in the channel 262, between the spring arms 260 and the flange 258, as shown for example in FIG. 12A. It will be appreciated that other techniques can also be used to mount, attach, or integrate the connector system 200 with the controller chassis 264. For example, the flange 258 can be configured to be disposed in the interior of the chassis 264, and/or can include one or more mounting screws or bolts for securing the housing 204 to the chassis 264. In some embodiments, the connector housing 204 can be formed integrally with at least one of the first connector body 206A and the second connector body 206B.

The components of the connector system 200 can be formed using a variety of techniques (e.g., stereolithography or injection molding) and from a variety of materials (e.g., polyvinyl chloride or polymethyl methacrylate (PMMA)).

Figure 11H:
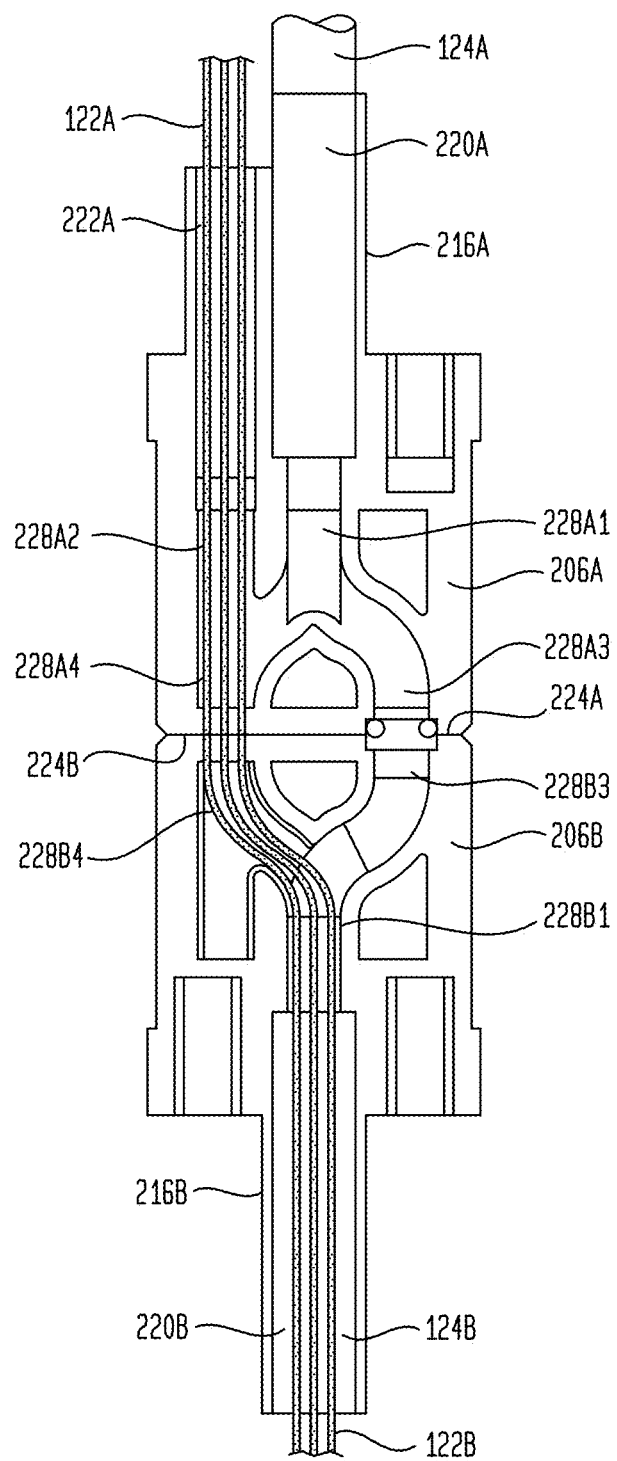
FIG. 11H is a cross-sectional top view of a connector system.

As shown in FIG. 11H, the first mating interface 224A of the first connector body 206A and the second mating interface 224B of the second connector body 206B can be placed in apposition such that fibers 122A extending through the first connector body are placed in optical communication with fibers 122B extending through the second connector body, and such that a fluid lumen 124A extending through the first connector body is placed in fluid communication with a fluid lumen 124B extending through the second connector body. The first mating interface 224A can be maintained in alignment with the second mating interface 224B by the connector housing 204.

Figure 12A:
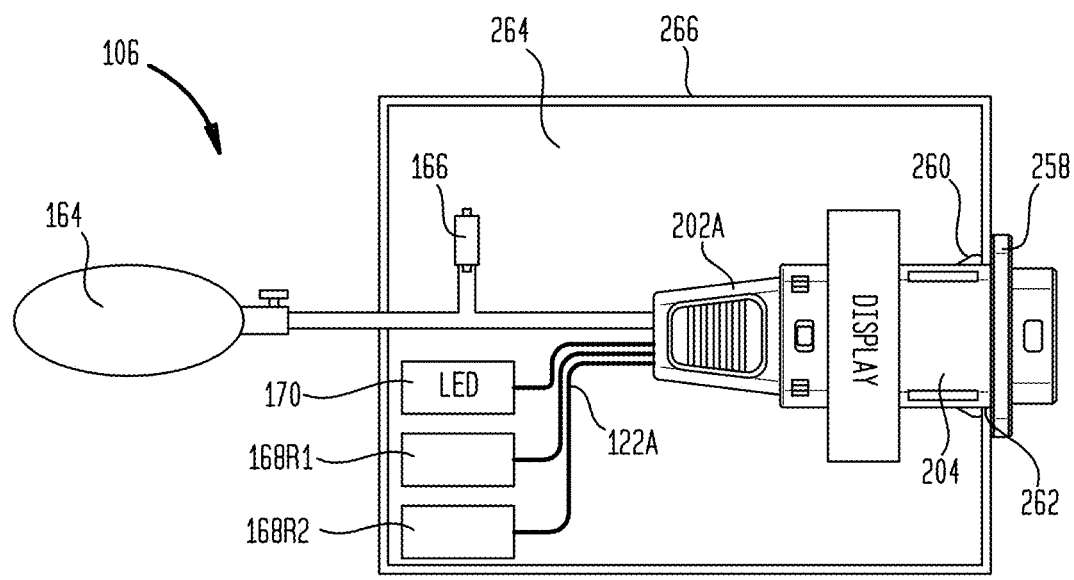
FIG. 12A is a schematic view of a reusable portion of an examination system.

As also shown in FIG. 11H, the connector system 200 can allow one or more optical fibers 122 to be introduced into a fluid-tight passage (e.g., the inflation tube 124 of a prostate evaluation system 100). In the illustrated connector system 200, a first set of three optical fibers 122A enters the proximal end of the first connector body 206A through the fiber passageway 222A in the proximal extension portion 216A. The fibers 122A then extend through the second leg 228A2 of the H-shaped lumen and into the fourth leg 228A4, where their terminal distal ends are presented at the first mating interface 224A. The terminal proximal ends of the fibers 122A can be coupled to the light source 170 and optical sensors 168R1, 168R2 of the controller 106, as shown in FIG. 12A. The first set of optical fibers 122A can thus extend through less than an entire length of the fluid lumen formed in the first connector body 206A.

Figure 12B:
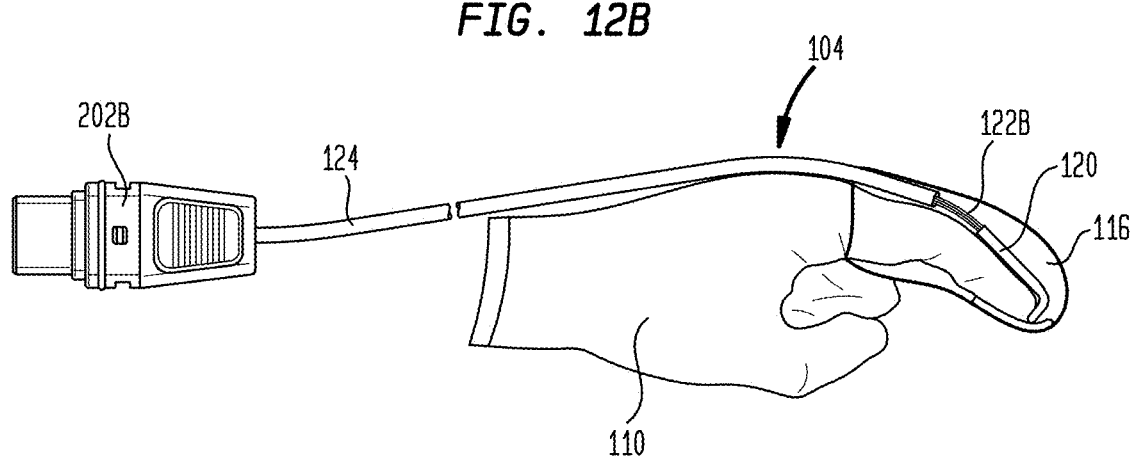
FIG. 12B is a schematic view of a disposable portion of an examination system.

A second set of three optical fibers 122B enters the distal end of the second connector body 206B through the inflation lumen 220B in the distal extension portion 216B. The fibers 122B then extend through the first leg 228B1 of the H-shaped lumen, through the crossover path, and into the fourth leg 228B4, where their terminal proximal ends are presented at the second mating interface 224B. The terminal distal ends of the fibers 122B can be mounted in the finger clip 120, as shown in FIG. 12B.

In some embodiments, the ends of the fibers 122A, 122B presented at the first and second mating interfaces 224A, 224B can be square-cut to form a butt joint with each other. In other embodiments, the ends of the fibers 122A, 122B can be slash- or oblique-cut to form a miter joint with each other. Use of a miter joint can, in some instances, reduce reflections produced at the fiber junction, and thereby reduce noise and improve measurement accuracy.

In addition to providing a fiber path, the connector system 200 can define a fluid-tight passageway extending therethrough. Fluid supplied from the controller inflation system (e.g., from a manual pump 164 and pressure relief valve 166 as shown in FIG. 12A) can enter the proximal end of the fluid passageway 220A and can flow through the first and third legs 228A1, 228A3 of the H-shaped lumen in the first connector body 206A. The fluid can then flow across the intersection of the first and second mating interfaces 224A, 224B, and into the third and first legs 228B3, 228B1 of the H-shaped lumen in the second connector body 206B. The fluid can then flow through the fluid passageway 220B formed in the distal extension portion 216B (e.g., to the inflation tube 124 leading to the sealed membrane volume 116 of the measurement assembly 104, as shown in FIG. 12B).

The mated connector system 200 thus provides a continuous fluid-tight passage having proximal and distal terminal ends, in which one or more optical fibers 122 can enter the fluid-tight passage at a location other than the proximal and distal terminal ends. In other words, the connector system 200 can allow optical fibers 122 to extend from a position outside of the inflation path to a position inside the inflation path without losing inflation pressure.

It will be appreciated that the system 100 can be divided into a reusable portion and a disposable portion. The reusable portion, shown in FIG. 12A, can include the controller 106, the connector housing 204 mounted in the controller chassis 264, and the first connector assembly 202A disposed within the controller chassis. The disposable portion, shown in FIG. 12B, can include the second connector assembly 202B and the measurement assembly 104. The connector system 200 can thus allow for quick and easy connection/ disconnection of the optical and fluid systems of the reusable portion and the disposable portion in a single operation.

Methods

An exemplary method of using the system 100 to measure a patient's prostate is as follows. First, the user can remove the disposable portion of the system (e.g., the measurement assembly 104 and the second connector assembly 202B) from its packaging. The user can then couple the disposable portion to the reusable portion of the system. For example, the second connector assembly 202B can be inserted into the connector housing 204 mounted in the controller 106. The user can then don the glove 110 and insert their forefinger into the patient's rectum. As noted above, the finger clip 120 can be attached to the dorsal and distal surfaces of the user's finger, such that the ventral surface of the user's finger remains free to perform a digital rectal examination as would conventionally be done with a standard exam glove. The user can therefore perform a standard digital rectal examination and obtain a prostate measurement using the system 100 without changing gloves.

When the user is ready to take a measurement, the membrane 112 can be positioned adjacent to the rectal wall in proximity to the prostate 102. The membrane 112 can then be inflated such that the membrane expands into contact with the rectal wall. The membrane 112 can be inflated by actuating a manual pump, or by pushing a button or other user interface element on the controller 106 to activate an electromechanical pump, valve, or other inflation system component. As explained above, when the membrane 112 is inflated, the spacing 128 and width of the indicia 126 on the reference pattern 118 can remain substantially constant.

Before or after inflating the membrane 112, the user can locate a first prostate lateral margin with their finger. The user can then push a button or other user interface element on the controller 106 to initiate execution of a measurement routine by the processor 152. The button or user interface element for initiating a measurement can be the same as the one for inflating the membrane 112, such that a single button push is effective to both inflate the membrane and initiate a measurement. Separate buttons can alternatively be provided. The user can then swipe their finger from the first prostate lateral margin to the second prostate lateral margin, thereby moving the finger clip 120 and associated optical fibers 122 along the measurement axis M of the reference pattern 118, as the reference pattern and membrane 112 remain stationary against the rectal wall.

As the user's finger moves across the reference pattern 118, light generated by the light source 170 can be transmitted to the reference pattern through the transmitting fiber 122T, and reflected back from the reference pattern to the optical detectors 168R1, 168R2 through the first and second receiver fibers 122R1, 122R2. As the receiver fibers move from a light region 128 to a dark region 126 and vice-versa, the optical sensor outputs provided to the processor 152 change. The processor 152 can maintain a count of such transitions until the user reaches the second prostate lateral margin, at which time the user can end the measurement procedure, for example by pushing a button or user interface element on the controller 106, or by holding their finger stationary such that a predetermined time elapses without a change in sensor output, thereby triggering the processor to end the measurement routine. If the user changes the direction in which they are moving their finger during the measurement routine, such a change in direction can be detected as described above and can trigger an error message to the user or compensation processing.

When the measurement procedure is finished, the processor 152 can calculate or estimate values for the palpable surface width and/or volume of the prostate as described above. These values can then be displayed on the display 160, stored in the storage device 158, and/or transmitted to the computer system 108 for storage and/or further processing. For example, the measured volume of the prostate can be compared to a threshold volume based on the patient's age or other factors to determine whether a biopsy should be recommended to the patient. When the user is finished taking measurements, the membrane can be deflated (e.g., automatically upon the user's pressing of an "end measurement" button) and the measurement assembly 104 can be removed from the patient. The second connector assembly 202B can be unplugged from the connector housing 204 and the disposable portion of the system 100 can be taken off and discarded in accordance with proper medical waste disposal procedures. In some embodiments, the "disposable" portion of the system 100 can also be cleaned and/or sterilized for subsequent reuse.

Measurement Assembly

FIGS. 13-20B illustrate an alternate measurement assembly 300 that can be used in the system 100 described above. For example, the measurement assembly 300 can be coupled to the controller 106 by the connector system 200 or another connector system of the type described herein, and can be used substantially as described above with respect to the measurement assembly 104 to measure an object (e.g., a prostate 102). The measurement assembly 300 can include any of the features described above with respect to the measurement assembly 104.

Figure 13:
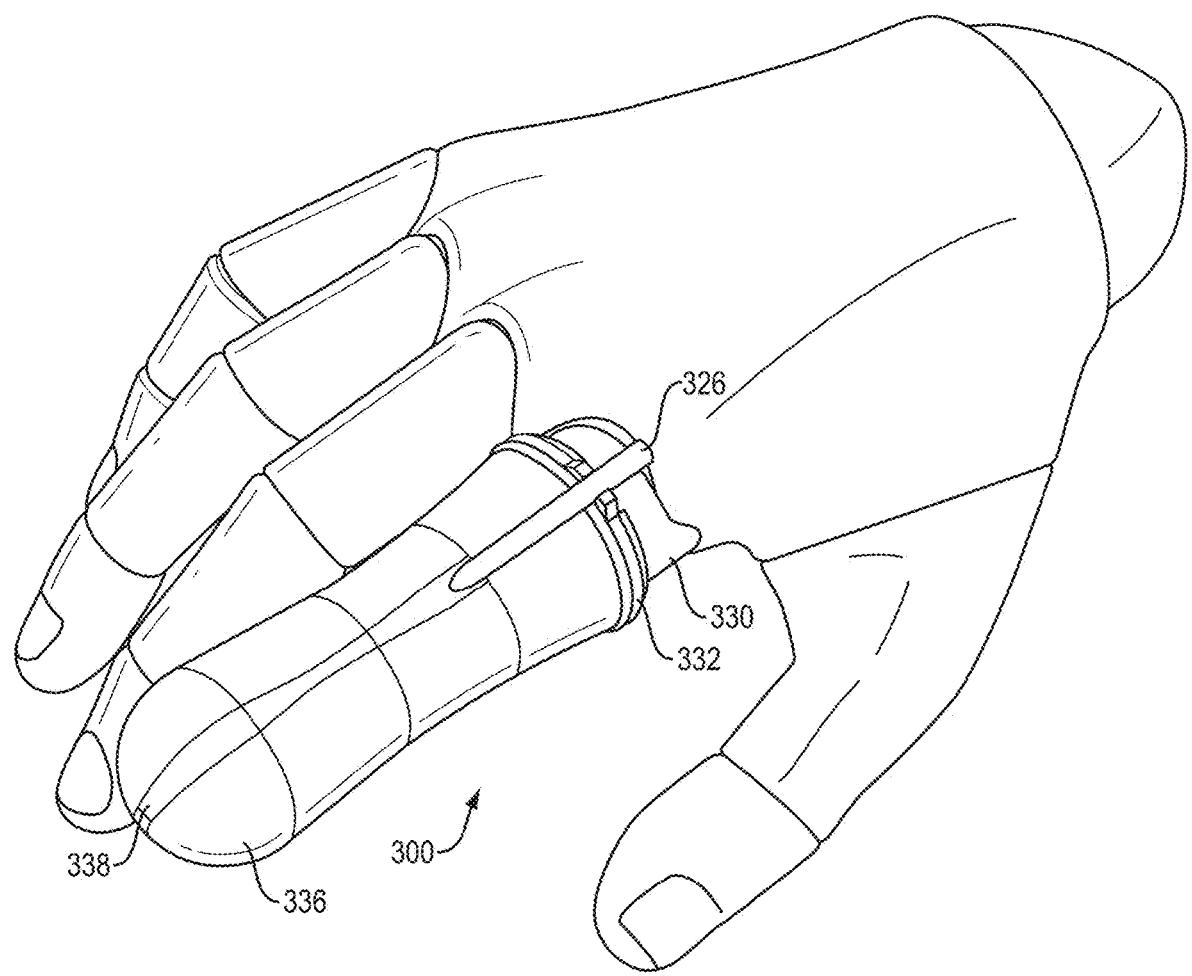
FIG. 13 is a perspective view of a measurement assembly worn on the hand of a user.
Figure 14:
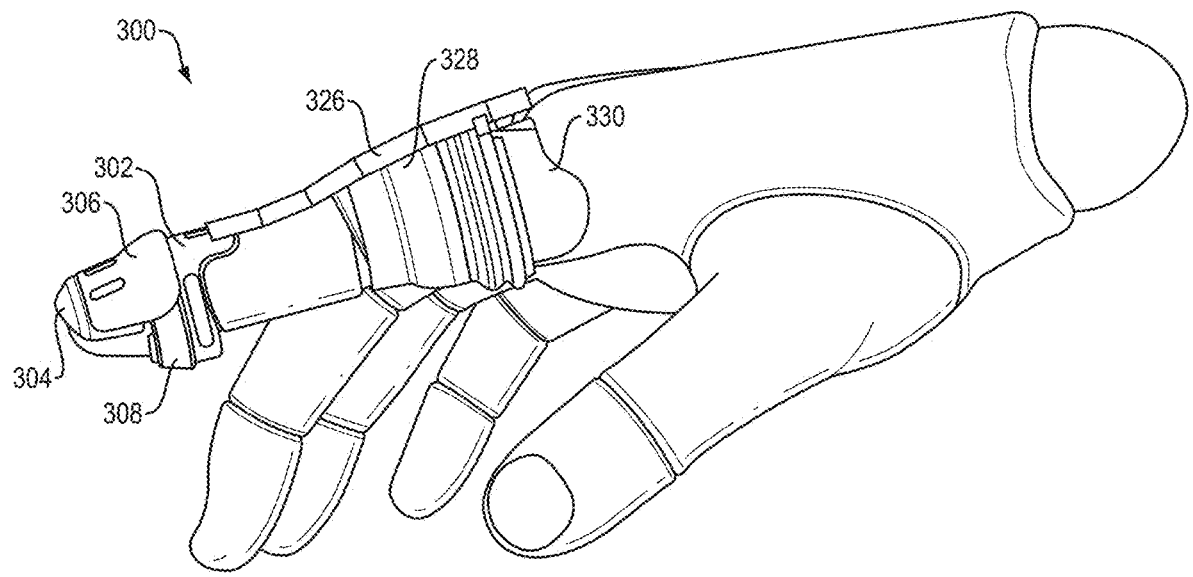
FIG. 14 is a perspective view of the measurement assembly of FIG. 13 with the balloon portion hidden.
Figure 15:
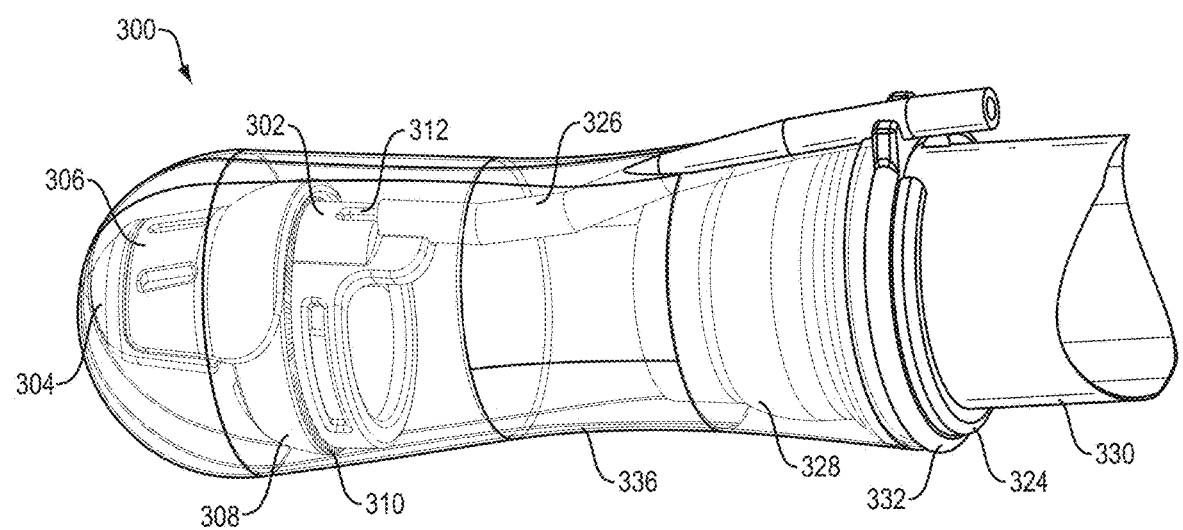
FIG. 15 is a perspective view of the measurement assembly of FIG. 13 with the balloon portion made transparent.
Figure 16:
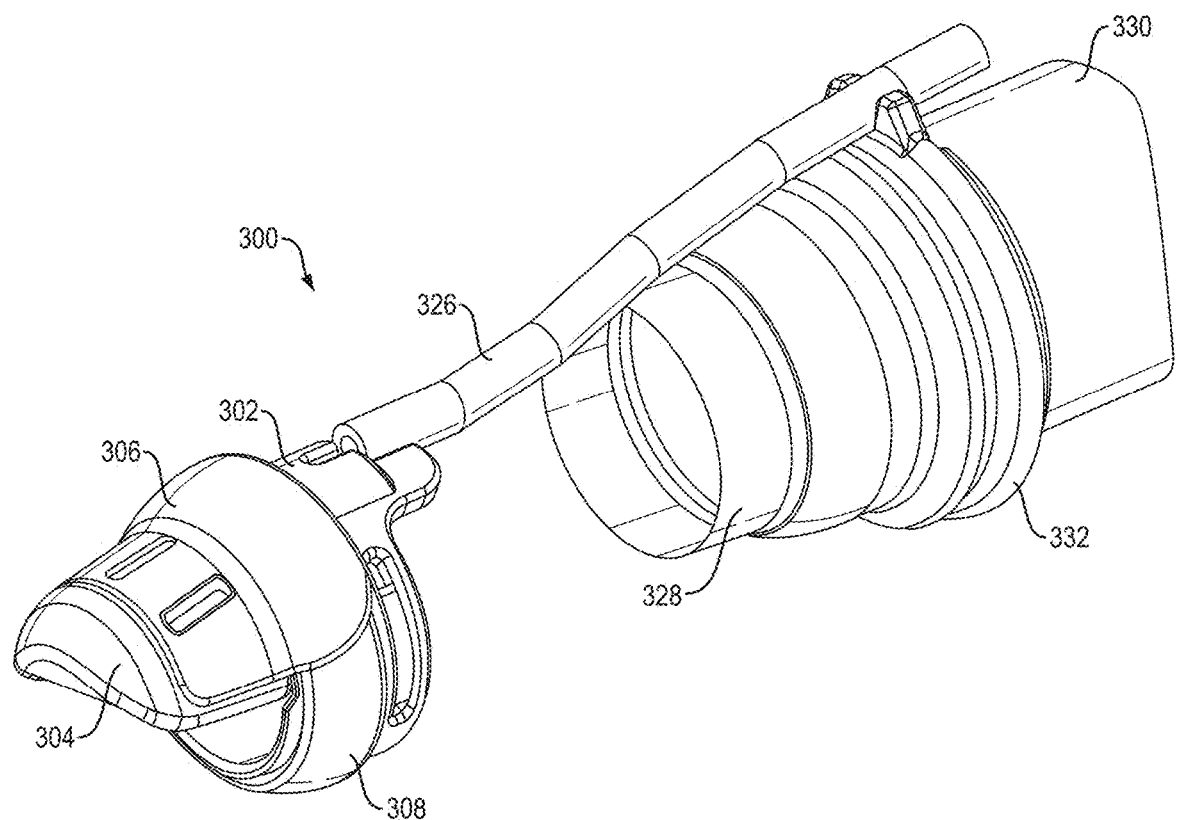
FIG. 16 is a perspective view of the measurement assembly of FIG. 13 with the balloon portion hidden.
Figure 17:
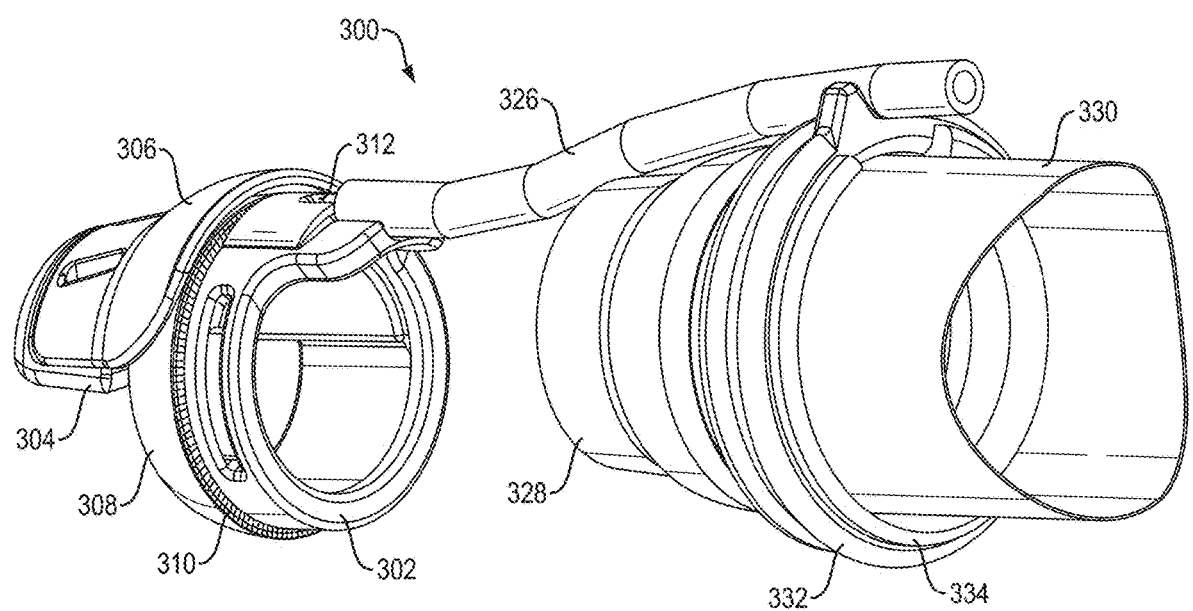
FIG. 17 is a perspective view of the measurement assembly of FIG. 13 with the balloon portion hidden.
Figure 18:
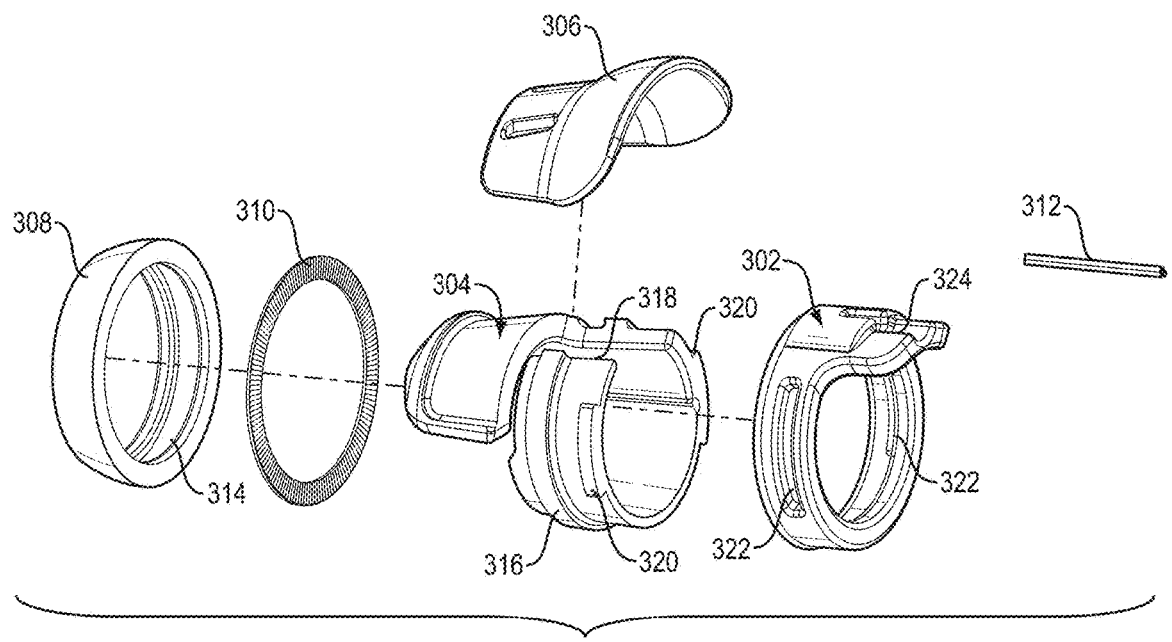
FIG. 18 is an exploded perspective view of a distal portion of the measurement assembly of FIG. 13.
Figure 19:
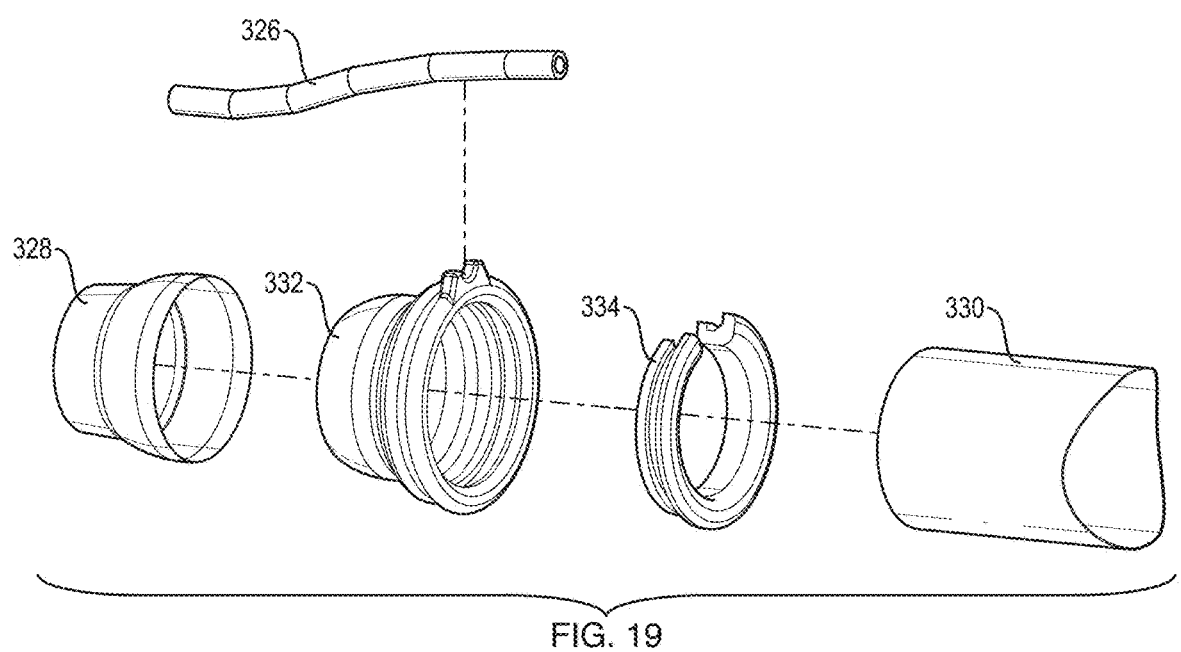
FIG. 19 is an exploded perspective view of a proximal portion of the measurement assembly of FIG. 13.
Figure 20A:
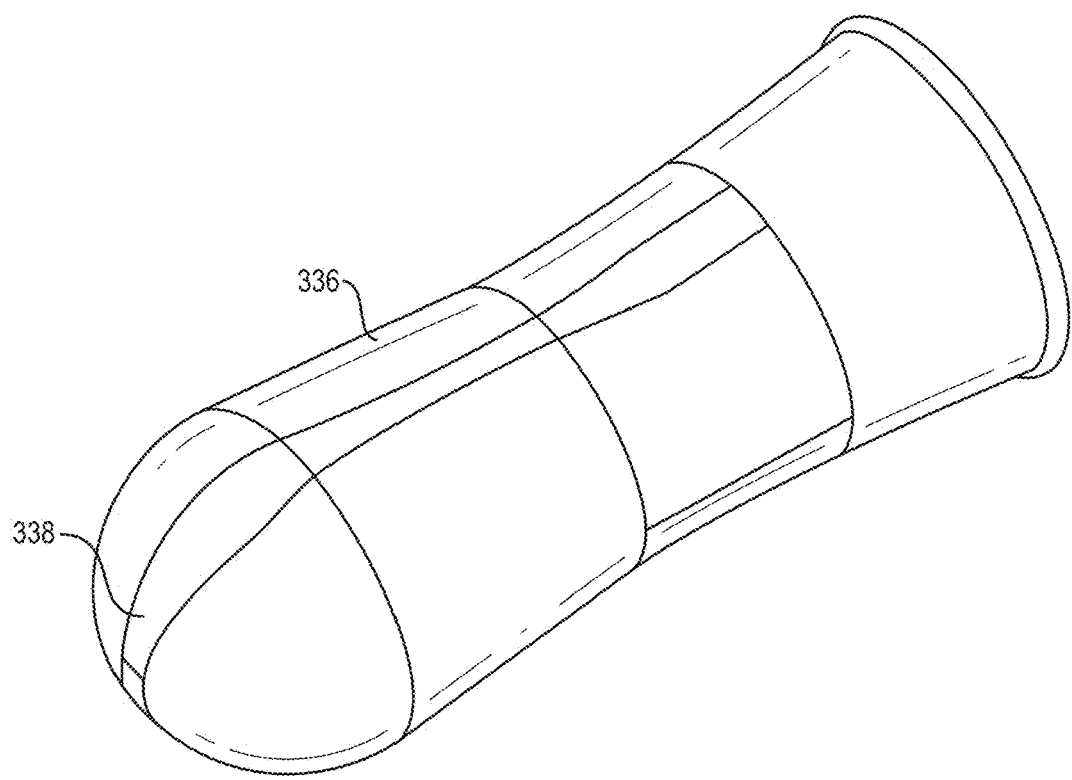
FIG. 20A is a perspective view of the balloon portion of the measurement assembly of FIG. 13.
Figure 20B:
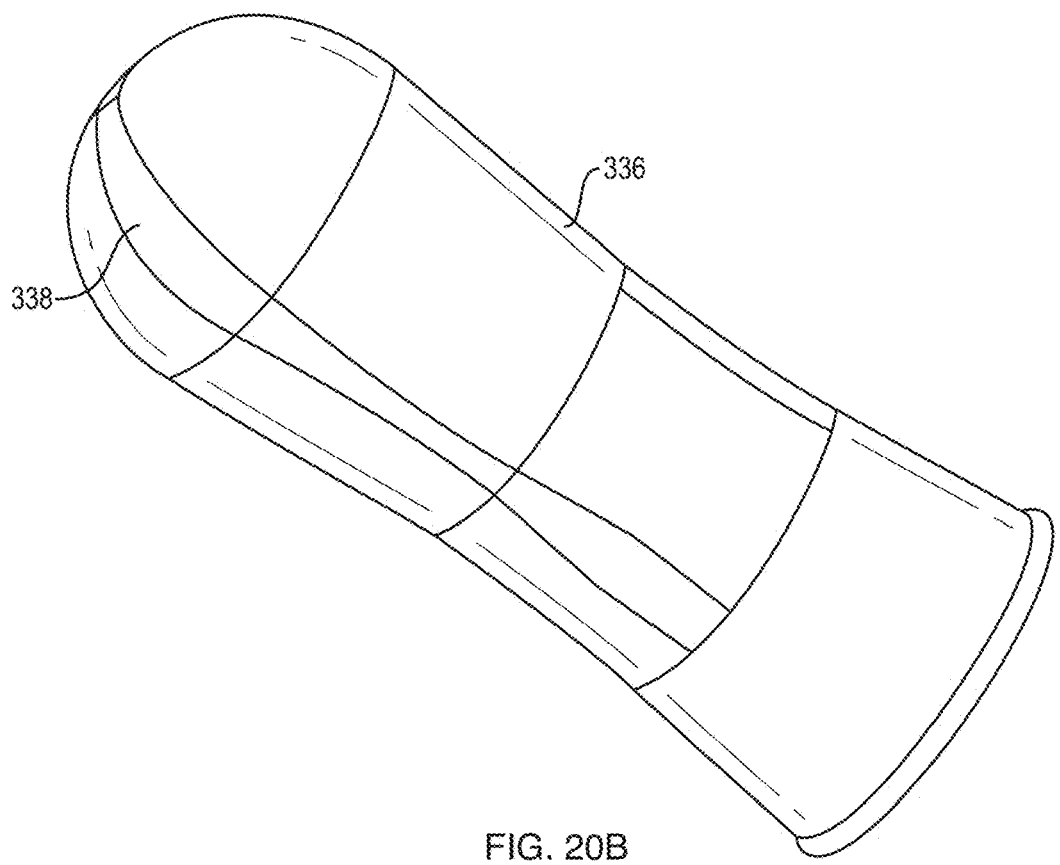
FIG. 20B is a perspective view of the balloon portion of the measurement assembly of FIG. 13.
Figure 21:
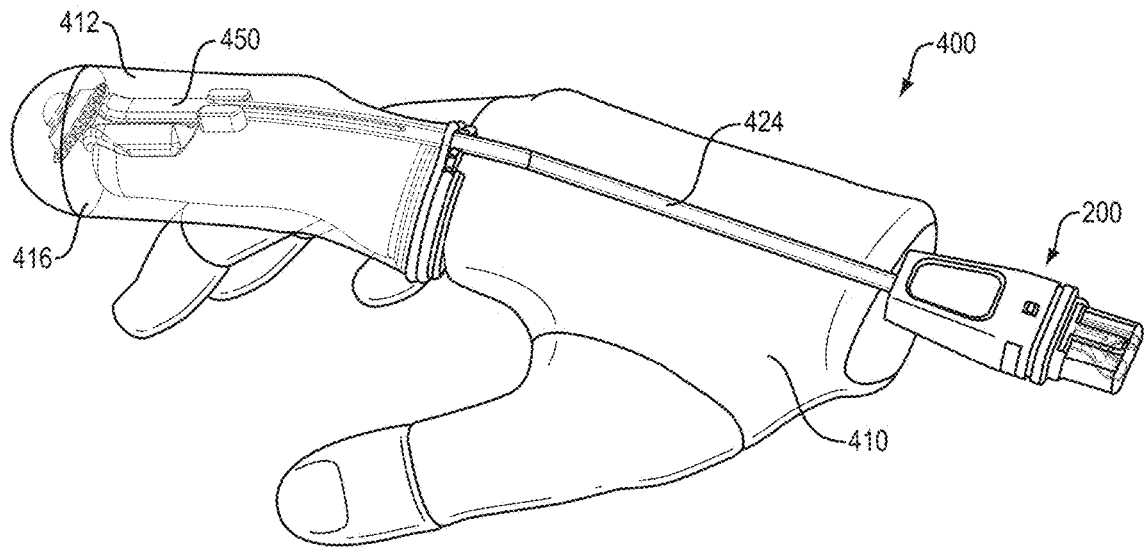
FIG. 21 is a perspective view of a measurement assembly.
Figure 22:
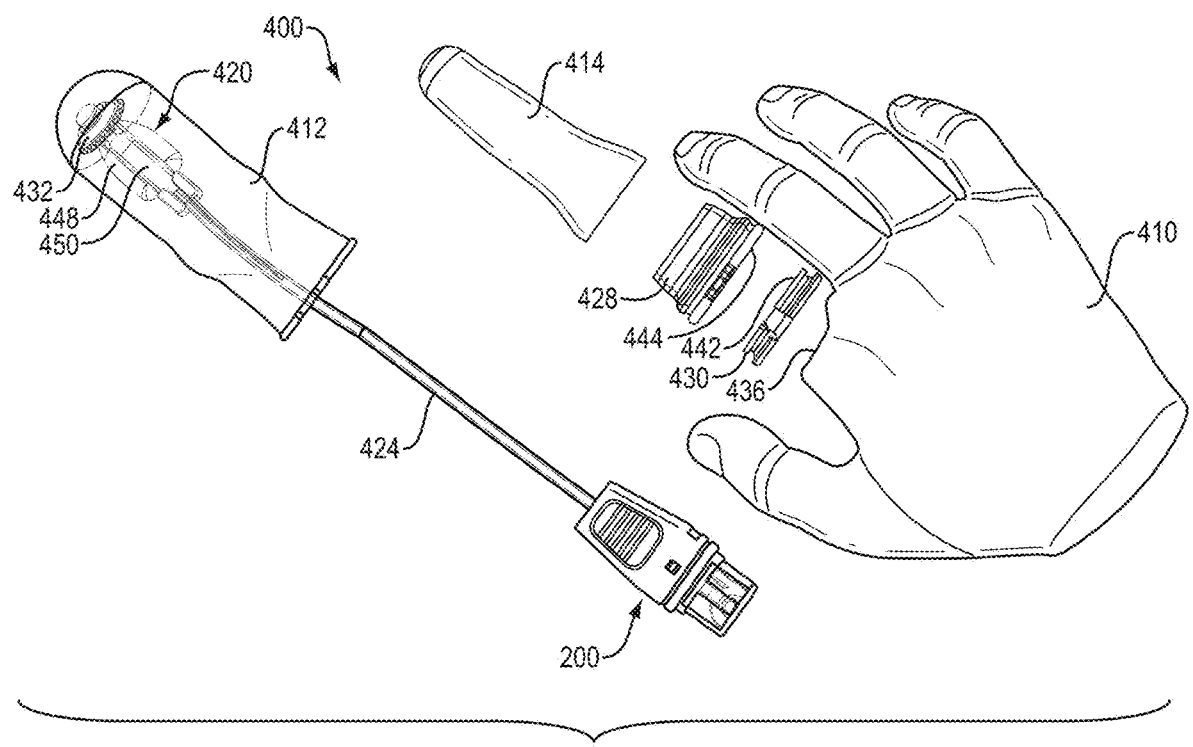
FIG. 22 is a partially exploded perspective view of the measurement assembly of FIG. 21.
Figure 23:
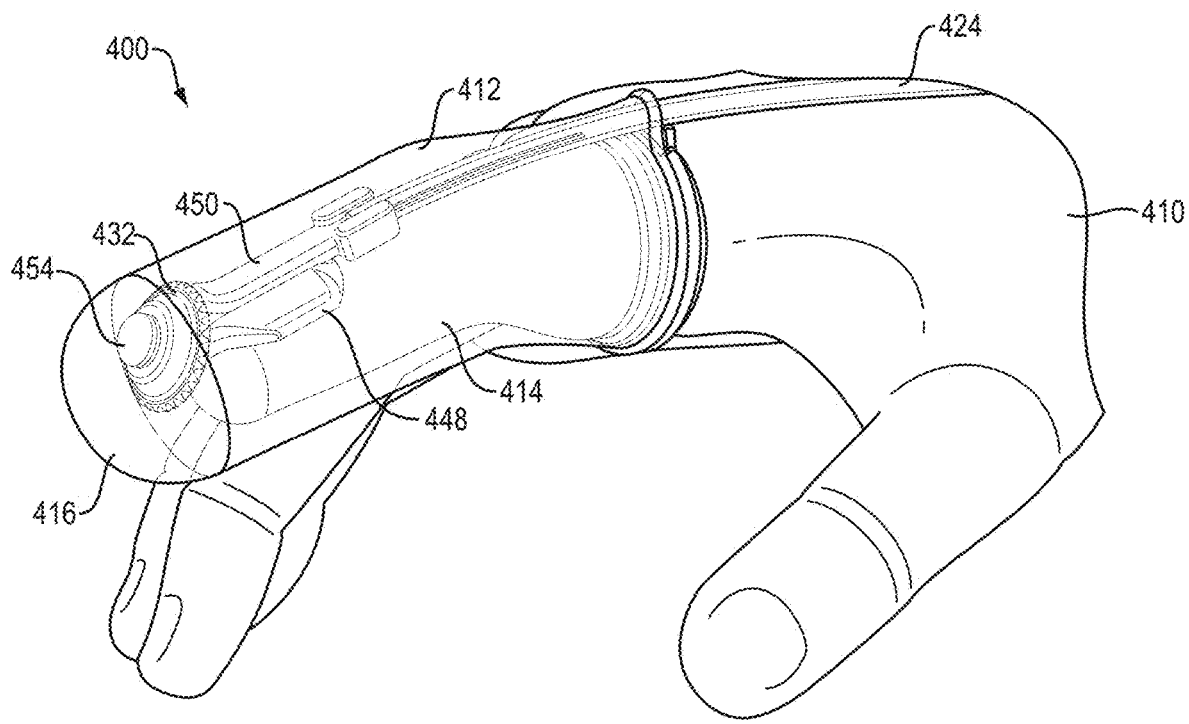
FIG. 23 is another perspective view of the measurement assembly of FIG. 21.
Figure 24:
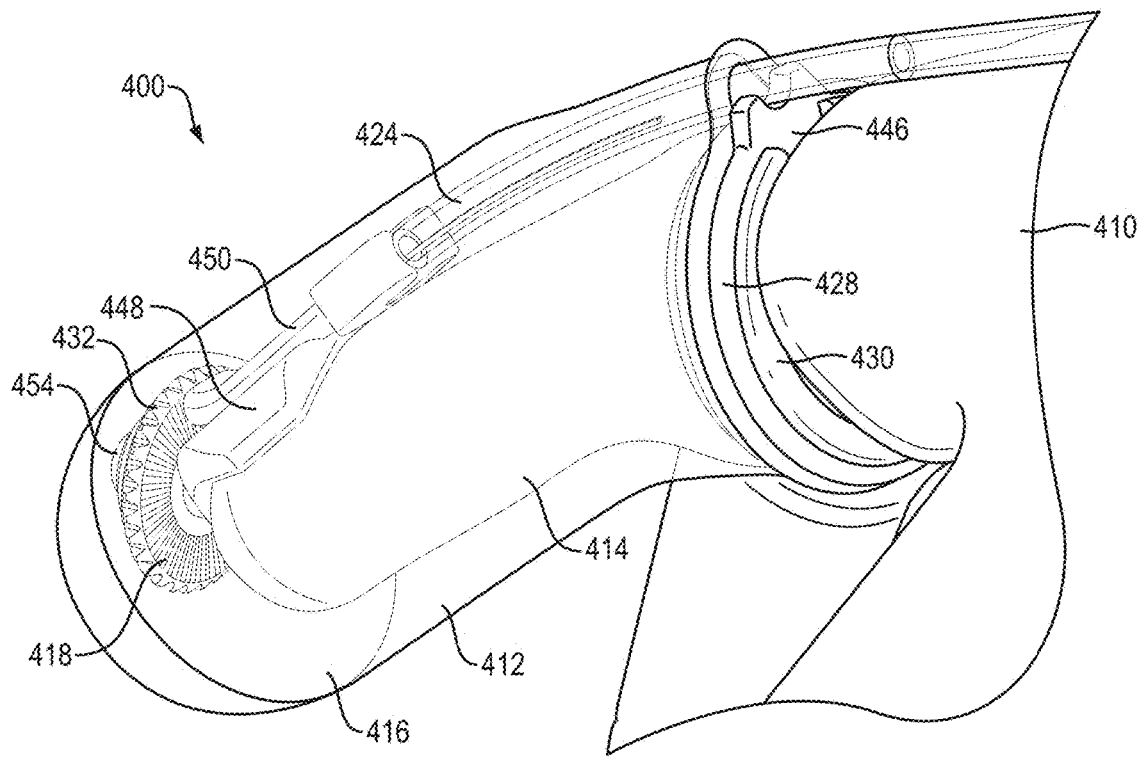
FIG. 24 is another perspective view of the measurement assembly of FIG. 21.
Figure 25:
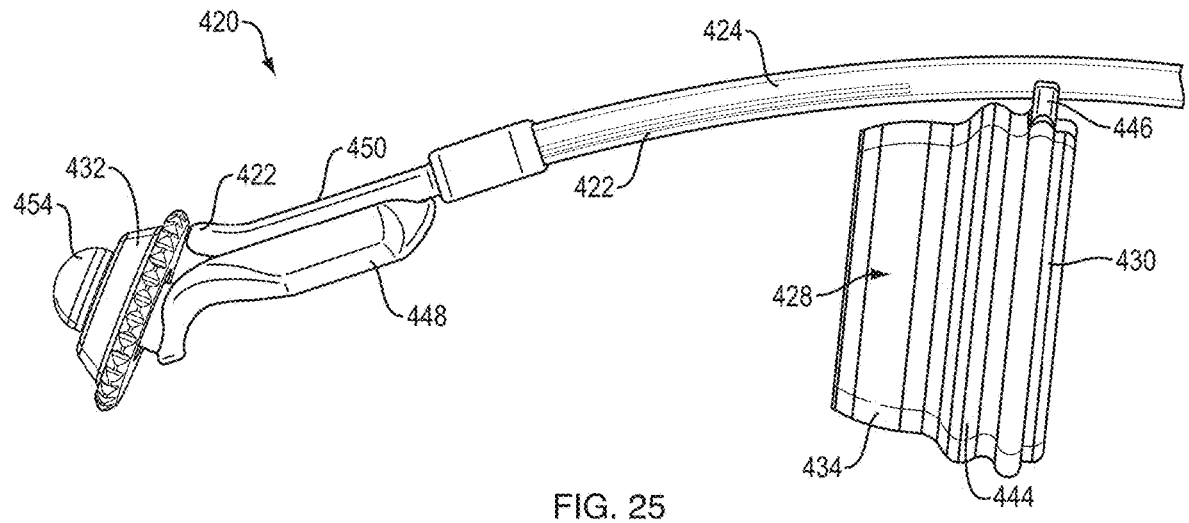
FIG. 25 is a side view of portions of the measurement assembly of FIG. 21.
Figure 26:
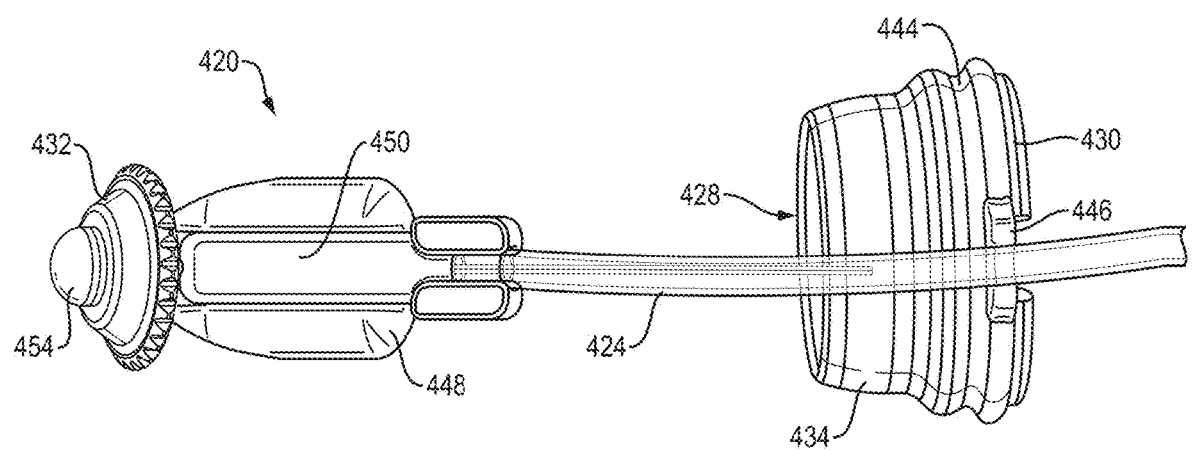
FIG. 26 is a top view of portions of the measurement assembly of FIG. 21.
Figure 27:
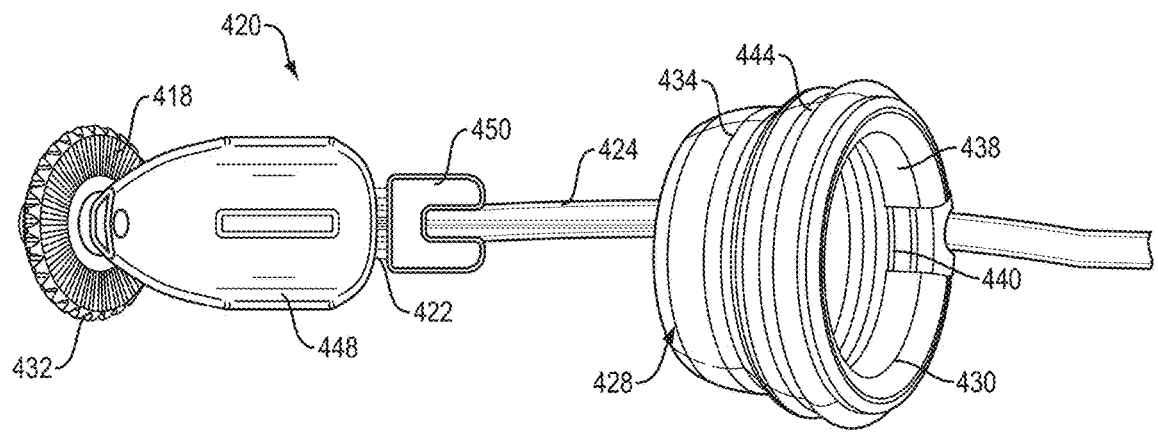
FIG. 27 is a bottom view of portions of the measurement assembly of FIG. 21.
Figure 28:
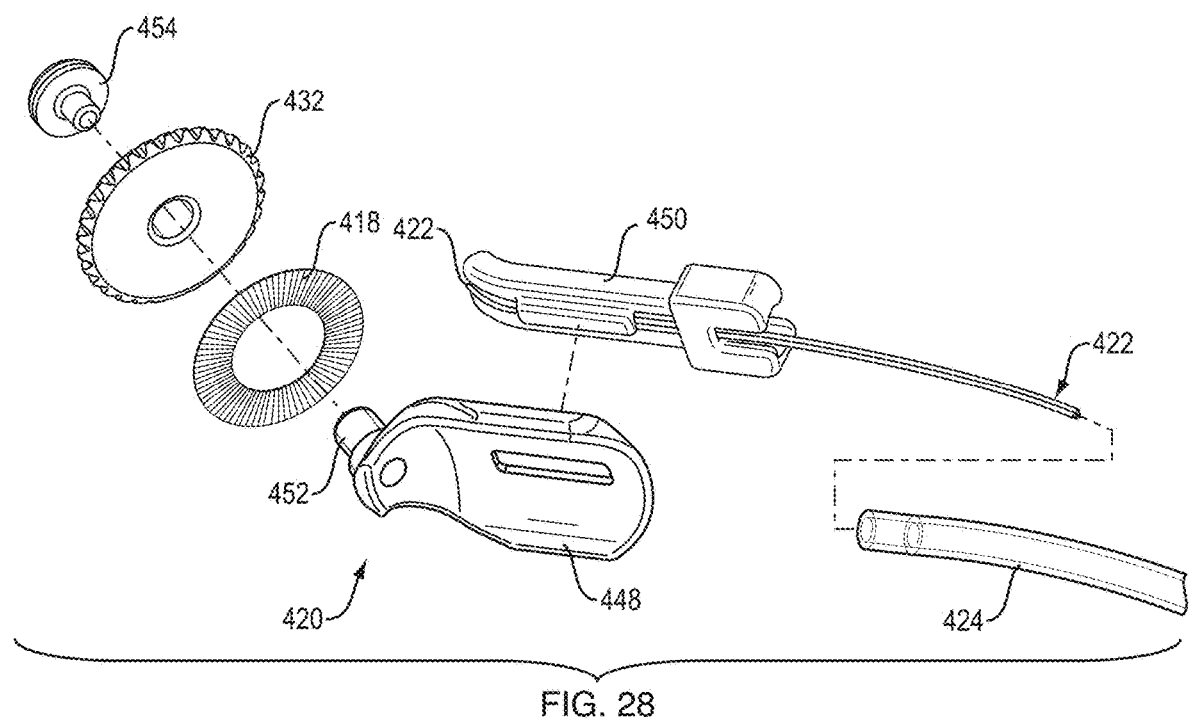
FIG. 28 is an exploded perspective view of portions of the measurement assembly of FIG. 21.
Figure 29:
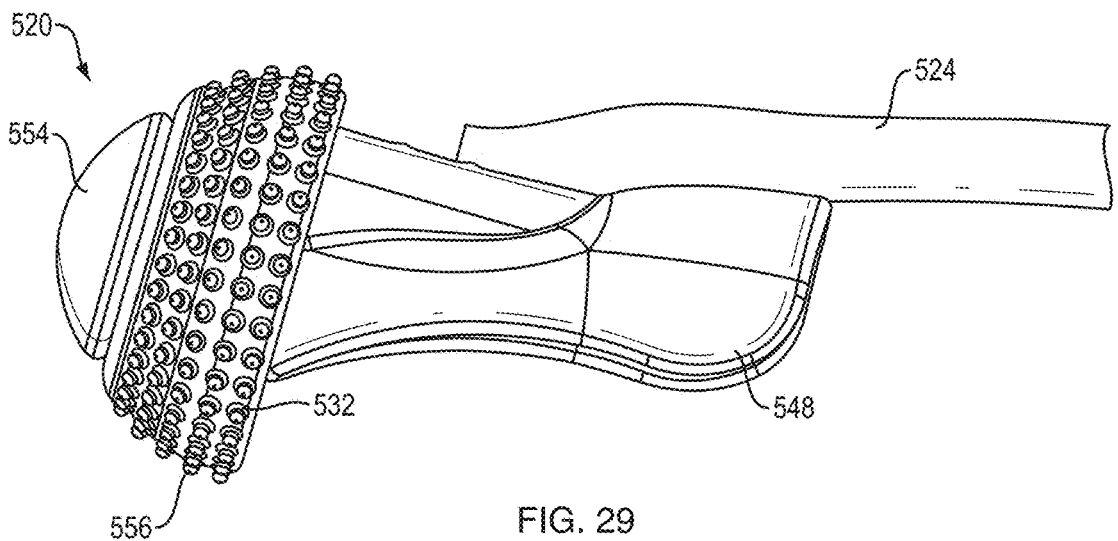
FIG. 29 is a side view of an alternative finger clip assembly.
Figure 30:
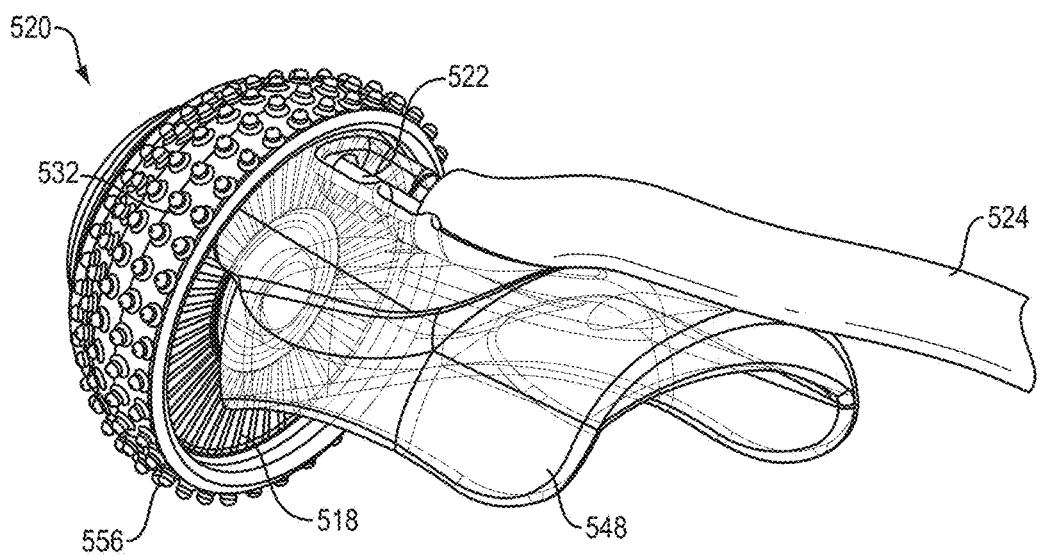
FIG. 30 is a perspective view of the finger clip assembly of FIG. 29, with a portion of the assembly shown as transparent.
Figure 31:
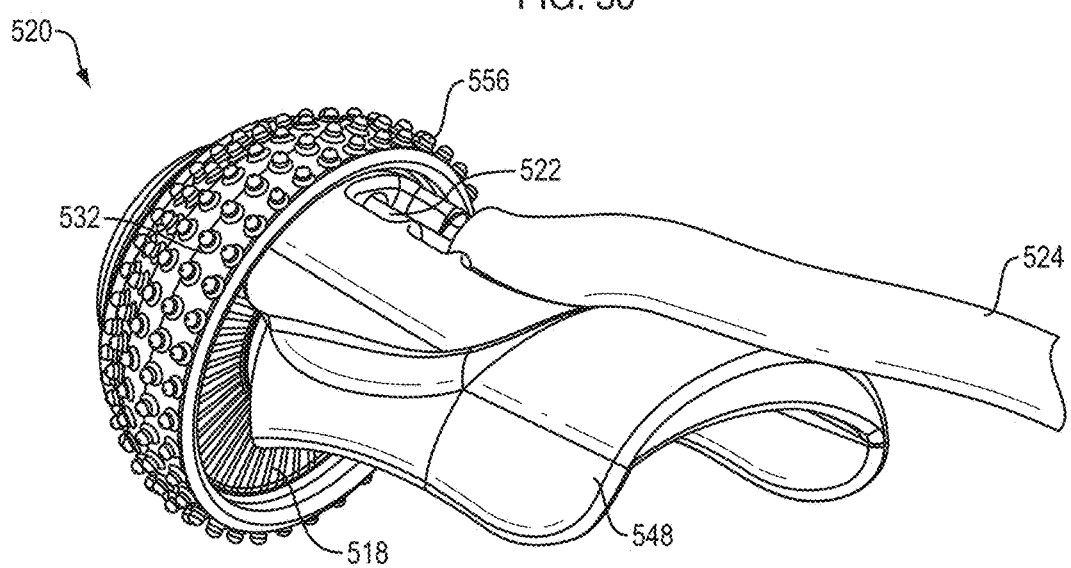
FIG. 31 is another perspective view of the finger clip assembly of FIG. 29.
Figure 32:
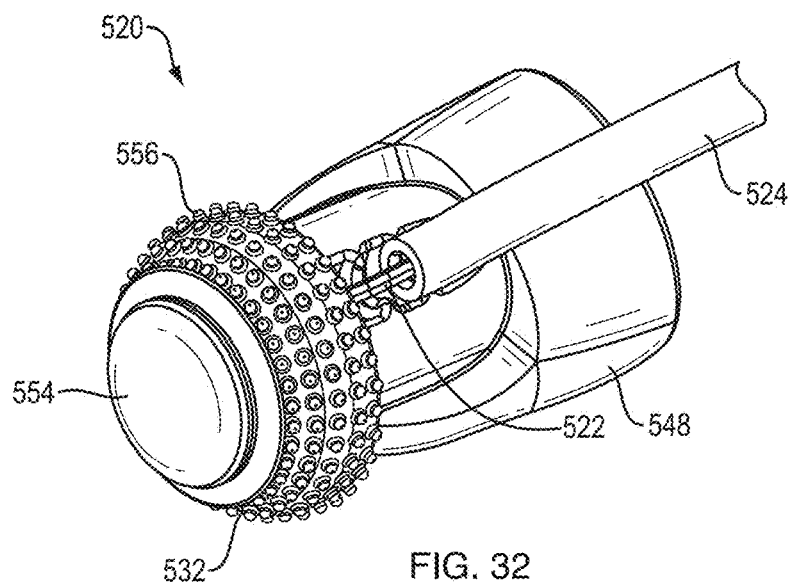
FIG. 32 is another perspective view of the finger clip assembly of FIG. 29.
Figure 33:
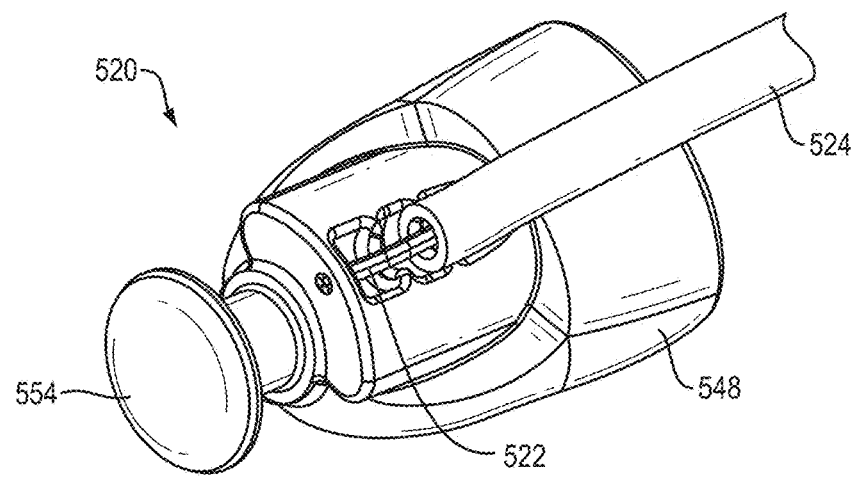
FIG. 33 is another perspective view of the finger clip assembly of FIG. 29, shown with the roller ring removed.
Figure 34:
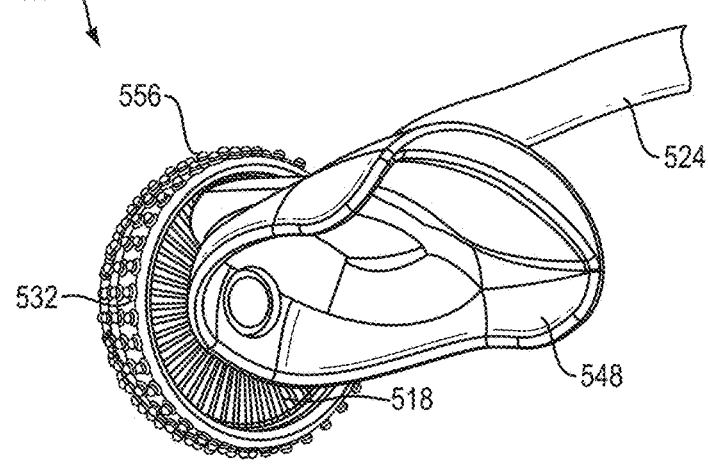
FIG. 34 is another perspective view of the finger clip assembly of FIG. 29.
Figure 35A:
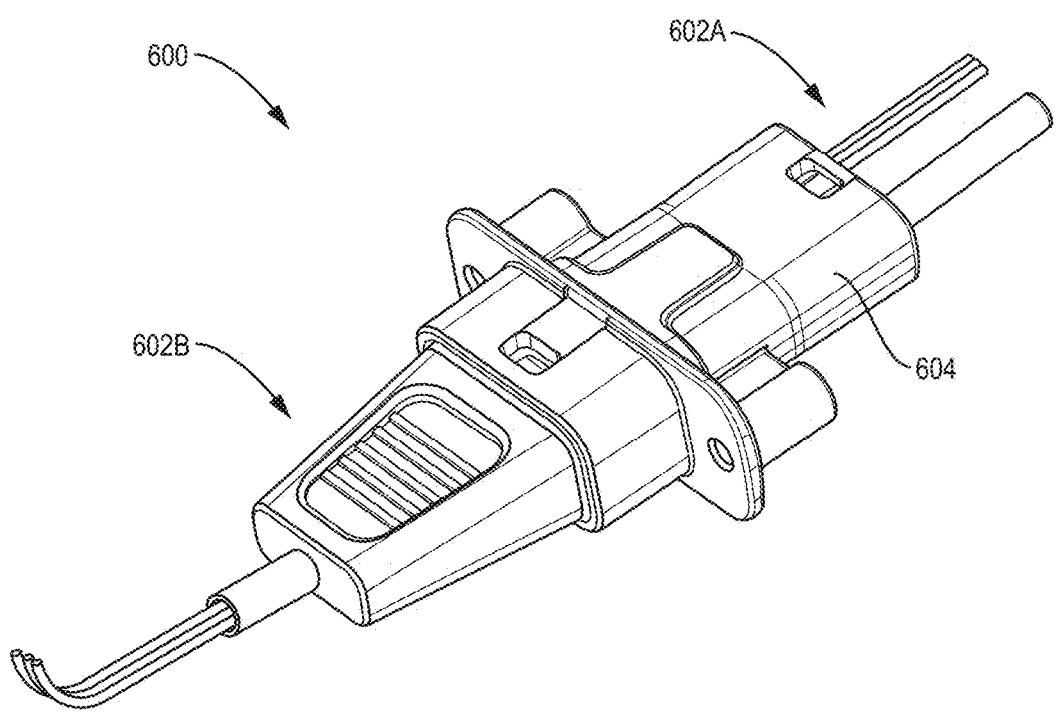
FIG. 35A is a perspective view of a connector system.
Figure 35B:
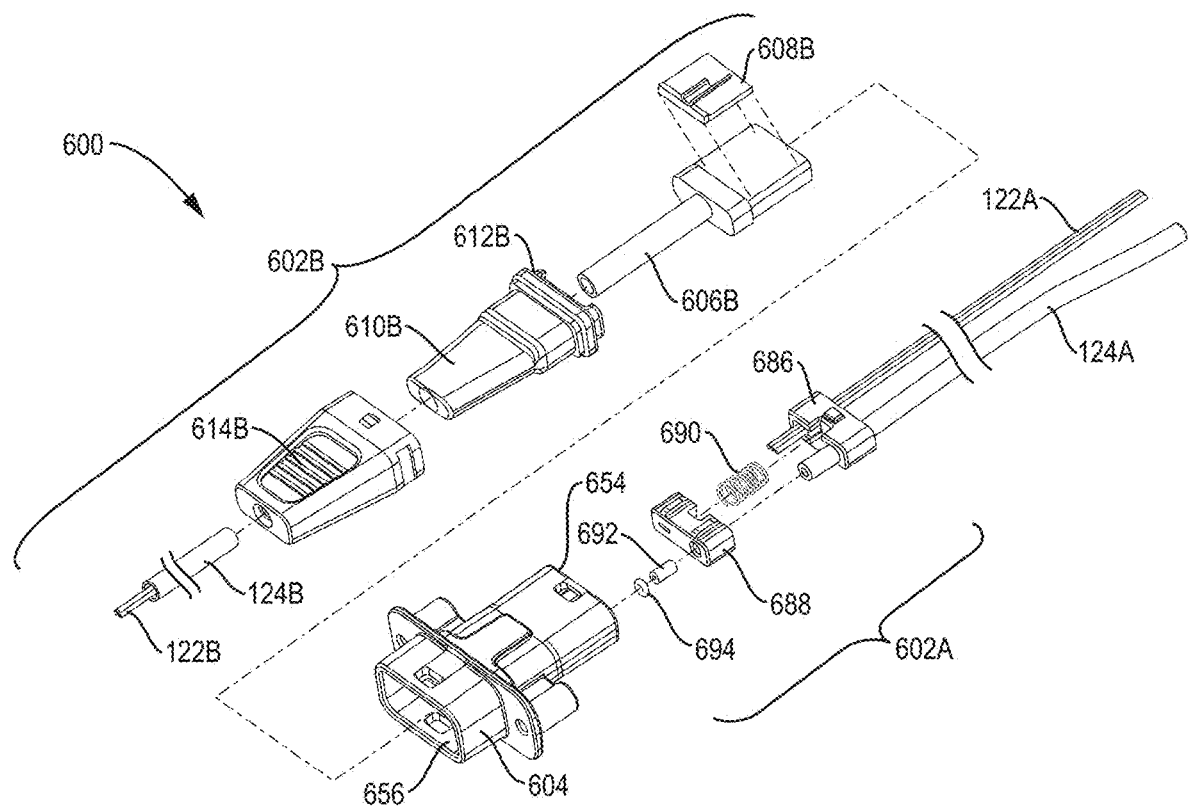
FIG. 35B is an exploded perspective view of the connector system of FIG. 35A.
Figure 35E:
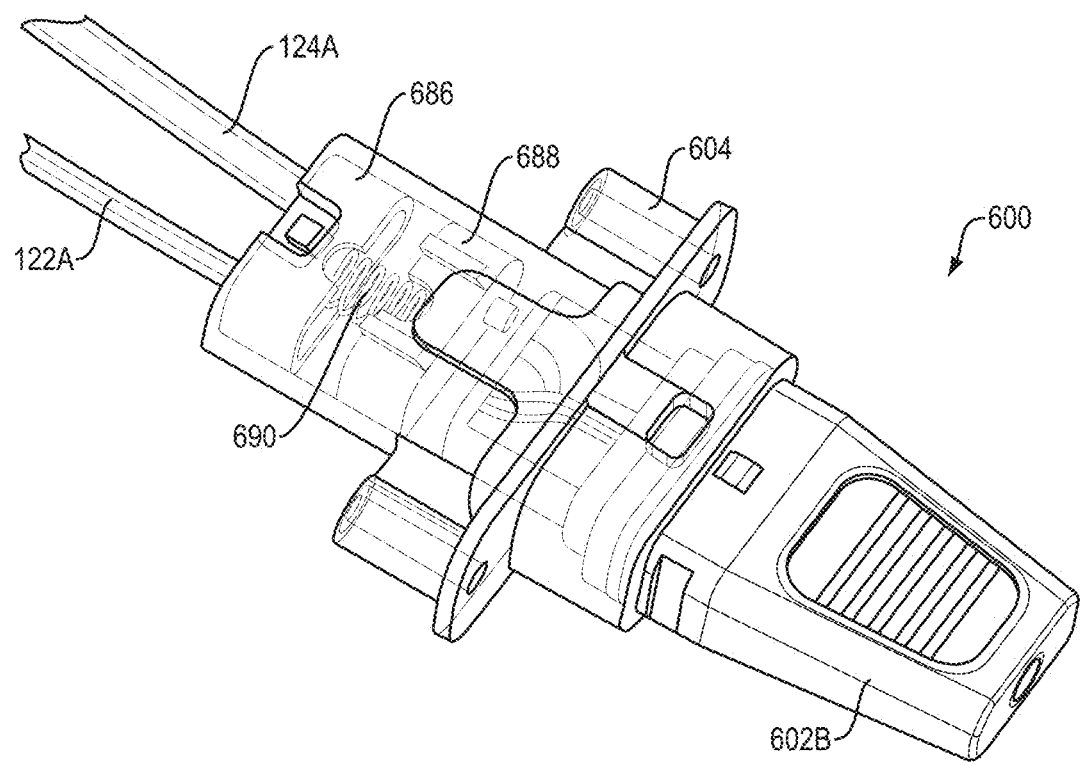
FIG. 35E is a perspective view of the connector system of FIG. 35A in a partially connected state, with the connector housing shown as transparent.
Figure 35F:
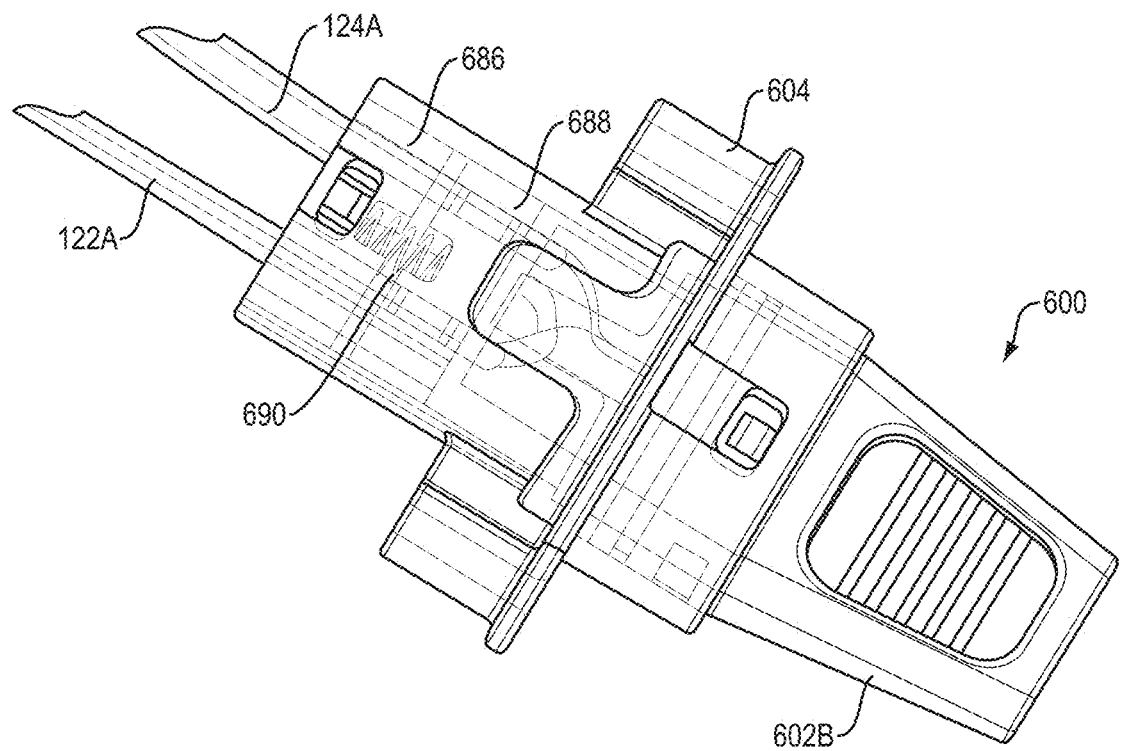
FIG. 35F is a perspective view of the connector system of FIG. 35A in a fully connected state, with the connector housing shown as transparent.
Figure 35G:
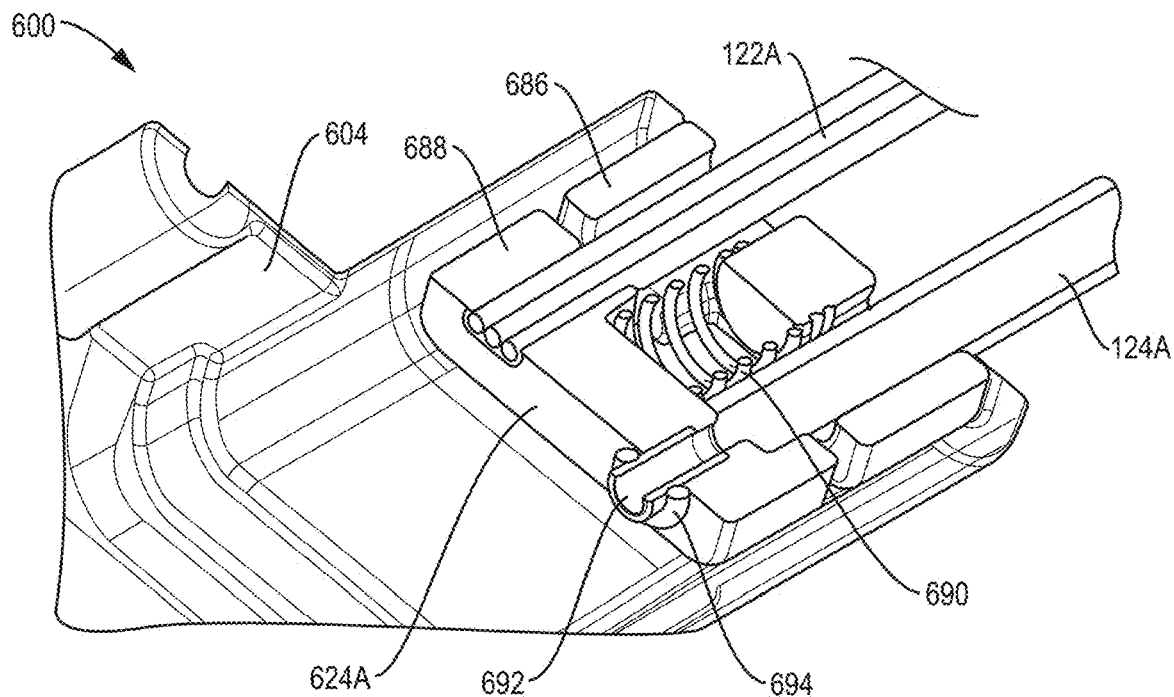
FIG. 35G is a sectional perspective view of a portion of the connector system of FIG. 35A.
Figure 35H:
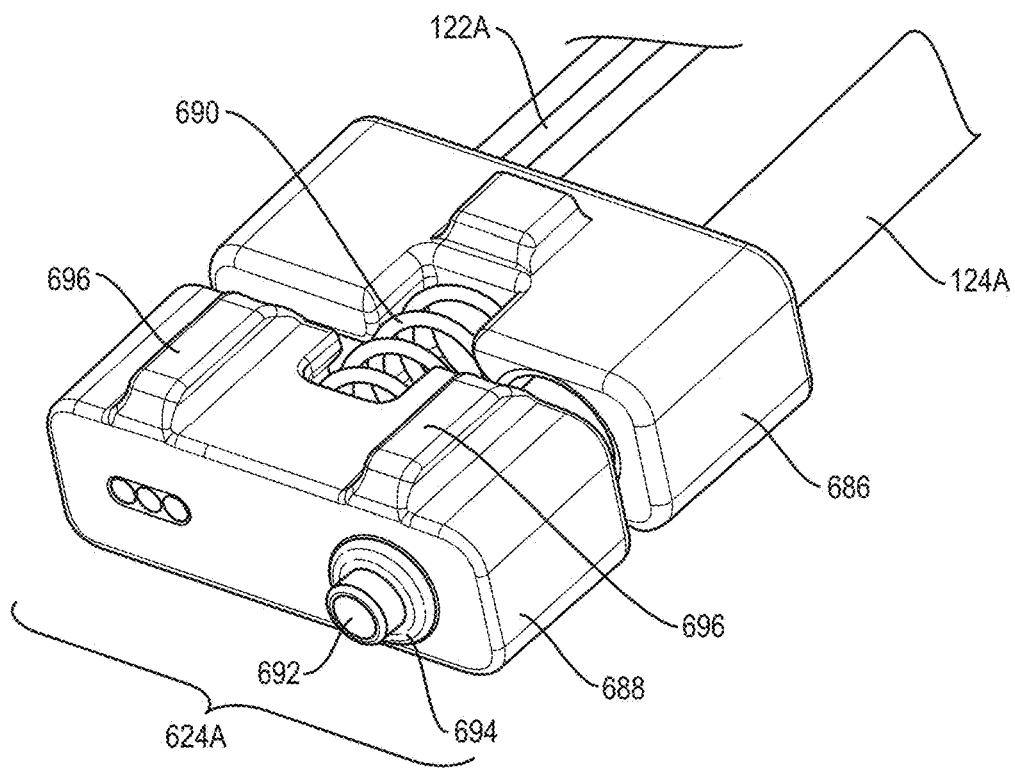
FIG. 35H is a perspective view of a portion of the connector system of FIG. 35A.

The measurement assembly 300 is shown being worn on a human hand in FIGS. 13-14 and in isolation in FIGS. 15-17. FIG. 18 is an exploded view of a distal portion of the measurement assembly 300, FIG. 19 is an exploded view of a proximal portion of the measurement assembly 300, and FIGS. 20A-20B are views of a balloon portion of the measurement assembly 300 from above and below. To facilitate illustration of the various components of the measurement assembly 300, the balloon portion is hidden in FIGS. 14, 16, and 17 and made transparent in FIG. 15.

The measurement assembly 300 can include a measurement pattern on a rotatable ring or wheel configured to be mounted to the user's finger. The measurement pattern can be configured to rotate relative to the user's finger as a measurement is taken.

As shown, in some embodiments, the distal portion of the measurement assembly 300 can include a finger clip base 302, a finger clip cap 304, a shroud 306, a roller ring 308, a measurement pattern 310, and one or more optical fibers 312.

The measurement pattern 310 can be adhered or otherwise attached to a proximal facing surface of the roller ring 308. In some embodiments, the measurement pattern 310 is formed integrally with the roller ring 308, e.g., by printing or engraving the measurement pattern directly on the roller ring. The measurement pattern 310 can include a continuous sequence of alternating light and dark regions. For example, the measurement pattern 310 can be a planar, ring-shaped member with a plurality of radially-extending white and black stripes arranged an a continuous manner about the circumference of the measurement pattern. The roller ring 308 can include an annular recess 314 formed in an interior surface thereof that receives a corresponding annular protrusion 316 formed on the finger clip cap 304. The recess 314 and the protrusion 316 can interact to allow the roller ring 308 to rotate about a central longitudinal axis of the finger clip cap 304 while maintaining the roller ring at a substantially fixed longitudinal position with respect to the finger clip cap. The finger clip cap 304 can include a longitudinal cutout 318 to allow the finger clip cap to deform radially inwards during assembly and then snap into engagement with the roller ring 308 when the recess of the roller ring is positioned over the protrusion of the finger clip cap. The outer surface of the roller ring 308 can have a textured coating or other surface features to provide additional friction when the roller ring is rolled across a surface to be measured.

The finger clip cap 304 can include first and second ears 320 that extend radially outward therefrom to snap into engagement with corresponding openings 322 formed in the finger clip base 302 to attach the finger clip cap to the finger clip base. The longitudinal cutout 318 of the finger clip cap 304 can allow the finger clip cap to deform radially inwards during assembly and then snap into engagement with the finger clip base 302 when the openings 322 of the base are positioned over the ears 320 of the cap. The finger clip base 302 can include a longitudinal channel through which the distal ends of the one or more optical fibers 312 are disposed. The finger clip base 302 can include a proximally-extending trough 324 that receives the distal end of the inflation tube 326 and acts as a stress relief. The finger clip base 302 can also serve as a polishing fixture for polishing the fibers 312 flush to the surface of the base 302, eliminating the need to pre-polish the fibers prior to fiber termination into the finger clip base. The shroud 306 can cover the upper or dorsal portion of the roller ring 308 to prevent inadvertent rotation of the roller ring, e.g., when the assembly 300 contacts portions of the rectum other than the palpable surface of the prostate. In some embodiments, the shroud 306 can be omitted.

The proximal portion of the measurement assembly 300 can include a distal sleeve 328, a proximal sleeve 330, a first ring 332, a second ring 334, and an inflation tube 326. The inflation tube 326 can provide a path for routing the fibers 312 to the distal portion of the measurement assembly 300 and can define an inflation lumen through which a fluid can be delivered to the interior of the balloon portion of the assembly to inflate the balloon 336. The sleeves 328, 330 and the rings 332, 334 can provide a fluid-tight seal between the user's finger and the balloon 336, such that the balloon can be pressurized and inflated without leakage back along the user's finger. The sleeves 328, 330 and the rings 332, 334 can also clamp the balloon 336 tightly to the user's finger to prevent the balloon 336 from rotating relative to the user's finger or slipping off of the user's finger. The sleeve 332 and the ring 334 can also provide an anti-torque connection between the glove 330, the human finger, and the balloon 336 such that movement of the finger and finger clip assembly does not impart any unwanted twisting torque to the balloon assembly.

In some embodiments, the proximal portion of the measurement assembly 300 can include an inner member and an outer member rotatably coupled to one another. The inner member can be rotationally fixed to the user's finger, e.g., via frictional engagement directly with the user's finger or with an intervening membrane. The outer member can be rotationally fixed to the balloon 336, e.g., via frictional engagement or an adhesive connection directly with the balloon or with an intervening membrane. The outer member can be configured to rotate relative to the inner member to allow the user to rotate their finger within the balloon 336.

The balloon portion of the measurement assembly can include an inflatable membrane 336 and a balloon constraint member 338. The inflatable membrane 336 can have a tapered or tear-drop shaped distal portion, a narrower central waist portion, and a flared proximal portion. The shape of the membrane 336 can advantageously promote the desired void geometry for accurate measurement, e.g., by promoting a large interior void in the vicinity of the roller ring 308. The distal portion of the inflatable membrane 336 can have a greater thickness than the remainder of the membrane, or can have a different material composition to make the distal end less elastic and less likely to deform distally when inflated, up into the cavity in which the measurement is being performed. In some embodiments, the inflatable membrane 336 can be formed from synthetic latex.

The balloon constraint member 338 can be configured to control the direction and/or degree to which the inflatable membrane 336 expands as it is inflated. In the illustrated embodiment, the balloon constraint member 338 is an adhesive strip or band of material that extends longitudinally along the dorsal surface of the membrane 336, wraps around the closed distal end of the membrane, and returns along the ventral surface of the membrane. The balloon constraint member 338 can be substantially resistant to stretching, and can therefore prevent the inflatable membrane 336 from stretching longitudinally during inflation. Instead, the inflatable membrane 336 can tend to expand radially when inflated. In addition, the balloon constraint member 338 can resist deformation of the balloon 336 in the ventral and dorsal directions, and instead urge the membrane to inflate laterally. This can give the inflated membrane 336 an asymmetrical shape (e.g., a shape having an oval transverse cross-section) which can advantageously prevent the inflated membrane from rotating within the rectum or other cavity in which the measurement is being performed. The balloon constraint member 338 can be a length of single or double sided tape adhered to the outside of the membrane 336 and bonded thereto by a thin layer of adhesive applied over the top of the balloon constraint member and the membrane. In some embodiments, the balloon constraint member 338 is just a smear of glue applied in a longitudinal stripe on the membrane 336. The balloon constraint member 338 can be embedded within the wall of the membrane 336.

In use, a user can insert their finger through the measurement assembly 300 such that the distal tip of the finger is seated against the distal end of the finger clip cap 304. As shown, the lower distal portion of the finger clip cap 304 can be open to allow the user to directly palpate the measurement area (through the balloon) if desired. The user can then swipe their finger laterally across the measurement area (e.g., the palpable surface of the prostate) to cause the roller ring 308 and the measurement pattern 310 attached thereto to rotate relative to the finger clip base 302 and the one or more optical fibers 312. Changes in detected light that occur as the measurement pattern 310 rotates in front of the fibers 312 can be processed by the controller to calculate a measurement distance which can in turn be used to estimate prostate volume. The one or more optical fibers 312 can include multiple receiver fibers, as described above, to allow the direction in which the roller ring 308 is rotating to be determined, which can allow for error detection or compensation. The fibers 312 can be positioned in a triangle configuration as described above. The measurement assembly 300 can be worn directly on the skin surface of the user without any additional glove or membrane, as shown, or can be used with one or more gloves. For example, the user can first don a glove and then insert their gloved finger into the measurement assembly 300 such that the measurement assembly is disposed over an exterior of the glove. By way of further example, the user can insert their finger into the measurement assembly 300 and then don a glove such that the glove is disposed over the exterior of the measurement assembly.

The measurement assembly 300 can, in at least some embodiments, provide a number of advantages. The structure of the measurement assembly 300 can maintain the fibers 312 at a minimal, fixed distance from the measurement pattern 310, regardless of variables such as user finger size, rectum dimensions, user movement, etc. which can improve measurement accuracy. The measurement pattern 310 can also be less susceptible to deformation or inadvertent movement, which can likewise improve measurement accuracy. The design of the measurement assembly 300 can also eliminate sharp bends in the fibers 312 which can reduce failure rate and make manufacturing easier. The shroud 306 can prevent the top surface of the roller ring 308 from contacting anything, so that the ring only rotates when the bottom surface is dragged across the prostate or other measurement target. The roller ring 308 can provide a continuous measurement pattern 310 to allow for infinite measurement distance, which can avoid the need to have different sized measurement patterns for different sized patients. The shroud 306 and finger clip cap 304 can have a tapered distal end shape to provide an atraumatic lead-in surface for initial insertion into the cavity in which the measurement is to be performed. The interior of the finger clip cap 304 can help retain the user's finger and the closed distal end can provide a positive indication that the user's finger is fully seated in the measurement assembly 300. The measurement assembly can include a large ventral window to give the user good tactile feedback when palpating the prostate. In other words, substantially the entire pad of the user's finger can be exposed via the window to facilitate palpation. The inside of the finger clip cap 304 can include a boss or ramped projection that acts to wedge the user's finger inside of the cap and provide a snug, secure fit.

Measurement Assembly

FIGS. 21-28 illustrate an alternate measurement assembly 400 that can be used in the system 100 described above. For example, the measurement assembly 400 can be coupled to the controller 106 by the connector system 200 or another connector system of the type described herein, and can be used substantially as described above with respect to the measurement assembly 104 or the measurement assembly 300 to measure an object (e.g., a prostate 102). The measurement assembly 400 can include any of the features described above with respect to the measurement assembly 104 or the measurement assembly 300.

The measurement assembly 400 can include a glove 410 with a membrane 412 disposed over a digit extension 414 thereof to define a closed volume 416 between the glove 410 and the membrane 412. The digit extension 414 can be a separate component from the rest of the glove. The digit extension can be attached to the glove, for example via first and second rings 428, 430. A finger clip assembly 420 can be disposed over the digit extension 414, beneath the membrane 412. The finger clip assembly 420 can include a roller wheel 432 with a reference pattern 418 formed thereon or coupled thereto. One or more optical fibers 422 can be mounted in a channel or lumen formed in the finger clip assembly 420. The optical fibers 422 can be configured to transmit light generated by a light source in the controller 106 to the reference pattern 418, and to transmit light reflected from the reference pattern to an optical sensor in the controller. The measurement assembly 400 can also include an inflation tube 424 extending into the closed volume 416 and configured to supply an inflation medium to the closed volume to inflate the membrane 412 and expand the closed volume, or to extract an inflation medium from the closed volume to deflate the membrane 412 and reduce the closed volume. The optical fibers 422 can extend through the inflation tube 424, and a suitable connector (e.g., a connector assembly 202B of the type described above) can be provided at a proximal end of the inflation tube for coupling the inflation tube and the optical fibers to the controller 106.

In an exemplary method of operation, the measurement assembly 400 can be worn by a user (e.g., disposed over the user's hand). The user can then position the membrane 412 in proximity to an area to be measured (e.g., a patient's rectal wall, adjacent the prostate). The membrane 412 can be inflated using the controller 106. With the membrane 412 remaining substantially stationary and the light source activated, the user can swipe their gloved finger and the finger clip assembly 420 attached thereto from a first lateral margin of the prostate to a second lateral margin of the prostate. As the finger clip assembly 420 moves across the prostate, the roller wheel 432 rotates to move the reference pattern 418 across the sight line of the fibers 422 such that light reflected from the reference pattern can be transmitted to the controller 106, where it can be processed to determine or estimate various properties of the prostate, such as the palpable surface width of the prostate or the volume of the prostate.

The glove 410 can include one or more digit extensions 414 corresponding to, and configured to receive, the fingers of a human hand. The glove 410 can thus be configured to be removably disposed around a human hand or a portion thereof. The glove 410 can be formed from any of a variety of materials suitable for use in a medical environment, including latex, natural rubber latex, neoprene, nitrile, vinyl, Vytex, and so forth. In some embodiments, the glove 410 can be a standard exam glove or surgical glove. In the illustrated embodiment, a complete glove is shown (e.g., a glove having five digit extensions and configured to envelop the entirety of a human hand). It will be appreciated, however, that in some embodiments less than a complete glove can be used. For example, the glove can be in the form of a finger cot configured to cover only a single finger or portion thereof. In other embodiments, the glove can be omitted altogether and the membrane 412 can be sealed directly around the user's finger.

The membrane 412 can be disposed over a portion of the glove 410 (e.g., one or more digit extensions 414 thereof), or can be disposed over the entirety of the glove 410. In some embodiments, the membrane 412 can be defined by a finger cot having an elongate tubular structure with a closed distal end and an open proximal end. The membrane 412 can have any of the features of the balloon 336 and/or constraint member 338 described above. The membrane 412 can be positioned over a digit extension 414 of the glove 410, such as the forefinger digit extension as shown, and the open proximal end of the membrane can be sealed circumferentially around the digit extension.

The measurement assembly 400 can include anti-torque features configured to isolate movement (e.g., rotation) of a digit extension from the rest of the glove. For example, in the illustrated embodiment, first and second anti-torque rings 428, 430 are used to attach the forefinger digit extension 414 to the rest of the glove 410. The digit extension 414 can be mated to a sealing surface 434 defined by a distal portion of the exterior surface of the first ring 428, for example using an adhesive. The open stub 436 on the glove 410 can be mated to a sealing surface 438 defined by a proximal portion of the interior surface of the second ring 430, for example using an adhesive. The first ring 428 can include an internal groove 440 configured to receive an external rib 442 formed on the second ring 430, such that the second ring can be at least partially received within the first ring and can be rotatably coupled to the first ring. Accordingly, the digit extension 414 can be free to rotate about its longitudinal axis with respect to the rest of the glove 410 by rotating the first ring 428 relative to the second ring 430. Decoupling rotation of the digit extension 414 from the rest of the glove 410 can advantageously allow the digit extension to move with a finger disposed therein without wrinkling, rotating, or twisting relative to the finger as the finger is moved relative to the rest of the glove. The first ring 428 can provide a fluid-tight seal between the digit extension 414 and the membrane 412, such that the interior volume 416 can be pressurized and inflated without leakage. The rings 428, 430 can clamp the digit extension 414 tightly to the user's finger to prevent the digit extension from rotating relative to the user's finger or slipping off of the user's finger.

The membrane 412 can be sealed directly to the glove 410, or the membrane can be sealed to the anti-torque assembly as described above. For example, the open proximal end of the membrane 412 can be sealed to a mating groove 444 formed in the exterior of the first ring 428. The membrane 412 can be sealed to the first ring 428 using any of a variety of techniques, including UV-curable and/or biocompatible cements or adhesives. Exemplary adhesives include Dymax 1202-M-SC and Dymax 222/450 (available from Dymax Corporation of Torrington, Conn.). The membrane 412 can be sealed to the first ring 428 and, by extension, to the digit extension 414 sealed to the first ring, such that a closed, fluid-tight volume 416 is defined between the membrane and the digit extension. In some embodiments, the membrane 412 can be rotatably coupled to the digit extension 414 and/or to the user's finger. In some embodiments, the membrane 412 can be sealed directly to the user's finger, without an intervening glove or digit extension.

The inflation tube 424 can extend through a cradle 446 formed in the first ring 428. The inflation tube 424 can be sealed between the membrane 412 and the first ring 428, such that the inflation tube extends into the closed volume 416 and a distal outlet of the inflation tube is disposed within the closed volume. The membrane 412 can be configured to expand or inflate when an inflation medium is supplied through the inflation tube 424, and to contract or deflate when an inflation medium is removed through the inflation tube. Like the glove 410, the membrane 412 can be formed from any of a variety of materials suitable for use in a medical environment, including latex, natural rubber latex, neoprene, nitrile, vinyl, Vytex, synthetic Polyisoprene, and so forth. In some embodiments, the membrane 412 is formed from the same material as the glove 410 and is configured to withstand strain forces applied thereto during inflation. The membrane 412 can have a thickness of about 0.010 inches. The thickness can be uniform along an entire area of the membrane 412, or the thickness can vary. The exterior surface of the membrane 412 can be knurled or otherwise textured to enhance grip with the surrounding cavity during a measurement.

The finger clip assembly 420 is shown in more detail in FIGS. 25-28. The finger clip assembly 420 can be configured to hold one or more optical fibers 422 in a fixed position relative to the user's finger, in a fixed position relative to one another, and/or in a fixed alignment relative to the reference pattern 418.

As shown, the finger clip assembly 420 can include a base portion 448 configured to substantially conform to the dorsal surface of a user's finger (or a user's gloved finger as the case may be). The base portion 448 can include a curved or bent distal end configured to substantially conform to the distal tip of the user's finger. Thus, the finger clip assembly 420 can be attached to the digit extension 414 of the glove 410 such that it extends along a dorsal surface of the digit extension and down across a distal tip of the digit extension. It will be appreciated that the finger clip assembly 420 can be adhered or otherwise attached to the digit extension 414, such that the finger clip assembly remains in a fixed position relative to a user's finger when the glove is worn by the user. Inflation pressure within the closed volume 416 can also be effective to retain the finger clip assembly 420 on the user's finger by pressing the digit extension 414 to which the finger clip assembly is attached down on to the user's finger.

The finger clip assembly 420 can include a fiber guide 450 that defines one or more paths through which one or more optical fibers 422 can be routed. For example, the fiber guide 450 can include an open channel, a closed tunnel, or a combination thereof through which the optical fibers 422 extend. The fiber guide 450 can be attached to a dorsal surface of the base portion 448, e.g., via a male projection that is snap-fit or adhered to a female recess defined in the base portion. The distal end of the fiber guide 450 can be curved upward in a dorsal direction to orient the optical windows of the fibers 422 with respect to the measurement pattern 418. For example, the fiber guide 450 can be shaped to orient the distal ends of the fibers 422 such that they extend perpendicular to the plane of the measurement pattern 418. The distal end of the fiber guide 450 can also be configured to maintain the distal end of the fibers 422 at a fixed distance from the reference pattern 418, which can improve measurement accuracy.

The fiber guide 450 can include a proximally-extending trough that receives the distal end of the inflation tube 424 and acts as a stress relief. The fiber guide 450 can also serve as a polishing fixture for polishing the fibers 422 flush to the surface of the fiber guide, eliminating the need to pre-polish the fibers prior to fiber termination into the finger clip assembly 400.

The measurement pattern 418 can be adhered or otherwise attached to a proximal facing surface of a roller ring 432. In some embodiments, the measurement pattern 418 is formed integrally with the roller ring 432, e.g., by printing or engraving the measurement pattern directly on the roller ring. The measurement pattern 418 can include a continuous sequence of alternating light and dark regions. For example, the measurement pattern 418 can be a planar, ring-shaped member with a plurality of radially-extending white and black stripes arranged an a continuous manner about the circumference of the measurement pattern.

The roller ring 432 can be rotatably mounted to the base portion 448 of the finger clip. For example, the roller ring 432 can include a central opening sized to receive a cylindrical protrusion 452 formed on the base portion 448 that serves as an axle. The roller ring 432 can be retained on the axle 452 by a locking pin 454. The locking pin 454 can include a proximally-extending post that is received within a female recess of the axle 452, e.g., via a threaded, snap-fit, or adhesive engagement. The locking pin 454 can have a blunt, rounded, or otherwise atraumatic distal-facing surface to reduce or prevent patient discomfort or irritation during use.

The roller ring 432 can be configured to rotate about a central longitudinal axis of the axle 452 while maintaining the roller ring at a substantially fixed longitudinal position with respect to the base portion 448. The outer surface of the roller ring 432 can have a textured coating or other surface features (e.g., ribs, teeth, grooves, etc.) to provide additional friction when the roller ring is rolled across a surface to be measured. The engagement surface of the roller ring 432 can be disposed distal to a distal-most extent of the user's finger. The central longitudinal axis of the axle 452 (and thus the axis of rotation of the roller ring 432) can be disposed at any of a variety of angles with respect to a central longitudinal axis of the user's straightened finger. The angle can be an oblique angle. The angle can be between about 0 degrees and about 90 degrees. The angle can be between about 30 degrees and about 60 degrees. The angle can be between about 40 degrees and about 50 degrees. The angle can be about 45 degrees. Angling the roller ring 432 can advantageously allow for the ring to be positioned substantially perpendicular to the rectal wall when the user's finger is bent to a typical palpation/examination position.

The finger clip assembly 420 can be disposed entirely within the closed volume 416 defined between the membrane 412 and the digit extension 414, such that its proximal end is adjacent to the distal outlet of the inflation tube 424. The inflation tube 424 can terminate a distance from the proximal end of the finger clip assembly 420, such that inflation media directed through the inflation tube 424 can exit the tube at its distal end and enter the closed volume 416 without being obstructed by the finger clip assembly 420.

The measurement assembly 400 can include one or more optical fibers 422 configured to transmit light generated by a light source to the reference pattern 418, and/or to transmit light reflected from the reference pattern to an optical sensor. The optical fibers 422 can extend through the inflation tube 424 and can be routed through the fiber path defined by the finger clip assembly 420. The optical fibers 422 can be secured within the fiber path, for example using a friction fit or a suitable adhesive.

In use, a user can insert their finger through the measurement assembly 400 such that the distal tip of the finger is seated against the distal end of the base portion 448 of the finger clip assembly 420. The ventral portion of the finger clip assembly 420 can be open to allow the user to directly palpate the measurement area (through the digit extension 414 and membrane 412) if desired. The user can then swipe their finger laterally across the measurement area (e.g., the palpable surface of the prostate) to cause the roller ring 432 and the measurement pattern 418 attached thereto to rotate relative to the fiber guide 450 and the one or more optical fibers 422. Changes in detected light that occur as the measurement pattern 418 rotates in front of the fibers 422 can be processed by the controller 106 to calculate a measurement distance which can in turn be used to estimate prostate volume. The one or more optical fibers 422 can include multiple receiver fibers, as described above, to allow the direction in which the roller ring 432 is rotating to be determined, which can allow for error detection or compensation. The fibers 422 can be positioned in a triangle configuration as described above. The measurement assembly 400 can include a shroud as described above.

The measurement assembly 400 can, in at least some embodiments, provide a number of advantages. The structure of the measurement assembly 400 can maintain the fibers 422 at a minimal, fixed distance from the measurement pattern 418, regardless of variables such as user finger size, rectum dimensions, user movement, etc. which can improve measurement accuracy. The measurement pattern 418 can be less susceptible to deformation or inadvertent movement, which can likewise improve measurement accuracy. The design of the measurement assembly 400 can also eliminate sharp bends in the fibers 422 which can reduce failure rate and make manufacturing easier. The roller ring 432 can provide a continuous measurement pattern 418 to allow for infinite measurement distance, which can avoid the need to have different sized measurement patterns for different sized patients. The finger clip assembly 420 can have a tapered distal end shape to provide an atraumatic lead-in surface for initial insertion into the cavity in which the measurement is to be performed. The interior of the base portion 448 can help retain the user's finger and the curved distal end can provide a positive indication that the user's finger is fully seated in the measurement assembly 400. The finger clip assembly 420 can include a large ventral window to give the user good tactile feedback when palpating the prostate. In other words, substantially the entire pad of the user's finger can be exposed via the window to facilitate palpation.

FIGS. 29-34 illustrate an alternative finger clip assembly 520 that can be used in place of the finger clip assembly 420 above. Except as indicated below and as will be readily apparent to a person having ordinary skill in the art viewing the drawings, the structure and operation of the finger clip assembly 520 is substantially the same as that of the finger clip assembly 420 described above. The illustrated finger clip assembly 520 generally includes an integral base portion/fiber guide 548, a roller ring 532 with a measurement pattern 518, and a locking pin 554, and can be coupled to an inflation tube 524 with optical fibers 522 extending therethrough. As shown, the roller ring 532 can have an increased proximal-distal dimension and can include a series of protrusions or gripping features 556 to promote rolling of the ring instead of sliding. The protrusions 556 can be spaced about the circumference of the roller ring and arranged in a plurality of rings or rows. While five rows of protrusions 556 are shown in the illustrated embodiment, it will be appreciated that the roller ring 532 can include any number of rows or any number of protrusions. The roller ring 532 can include various other gripping features instead or in addition, such as teeth, knurling, grooves, coatings, roughening, etc. The contact surface of the roller ring 532 can define a section of a sphere. The contact surface of the roller ring 532 can have a convexly curved exterior surface.

Connector System

As noted above, the system 100 can include one or more multiplex connector systems for coupling a measurement assembly (e.g., the measurement assemblies 104, 300, 400) to the controller 106. FIGS. 35A-35H illustrate an exemplary embodiment of a connector system 600 in which a first fluid lumen and a first set of optical fibers (which can be disposed in the controller 106) can be selectively coupled to a second fluid lumen and a second set of optical fibers (which can be disposed in the measurement assembly 104). The illustrated connector system 600 can advantageously ensure proper alignment between the inflation and optical systems of the controller 106 and the measurement assembly 104. The connector system 600 can also allow the optical fibers to transition from a position outside of the inflation lumen to a position within the inflation lumen. The connector system 600 can also help ensure a repeatable positive face-to-face contact/mating of the fibers regardless of any differences in the connector dimensions and final latched position.

Except as indicated below and as will be readily apparent to a person having ordinary skill in the art viewing the drawings, the structure and operation of the connector system 600 is substantially the same as that of the connector system 200 described above.

As shown, the connector system 600 can include a first connector assembly 602A, a second connector assembly 602B, and a connector housing 604.

The first connector assembly 602A can include a base 686, a slider 688, and a bias element or spring 690. A first set of optical fibers 122A (e.g., of the controller 106) can be secured to the slider 688. For example, the ends of the fibers 122A can be inserted through a slot formed in the slider 688 and secured in place using an adhesive or other attachment. Once inserted through and secured to the slider 688, the ends of the fibers 122A can be cut and polished using the slider as a fixture.

A first inflation tube 124A (e.g., of the controller 106) can be secured to the slider 688. For example, a distal end of the inflation tube 124A can be inserted into a proximal opening of the slider 688 and secured in place using an adhesive or other attachment. A nipple 692 can be secured in a distal opening of the slider 688, opposite to and in fluid communication with the proximal opening. The nipple 692 can be secured in place using an adhesive or other attachment. In some embodiments, the nipple 692 can be a short length of brass tubing. A seal or O-ring 694 can be positioned around the nipple 692. The slider 688 can thus define a first mating interface 624A at which the fibers 122A and a fluid lumen of the inflation tube 124A are presented for connection to the second connector assembly 602B.

The slider 688 can be configured to longitudinally translate within the connector housing 604. The slider 688 can include protrusions 696 which can be received in corresponding tracks formed in the interior of the housing 604 to guide sliding of the slider relative to the housing. It will be appreciated that, in alternative configurations, the protrusions can be formed in the housing 604 and the tracks can be formed in the slider 688. The fibers 122A and the inflation tube 124A can be fixedly coupled to the slider 688 such that, when the slider translates relative to the housing 604, the fibers 122A and the inflation tube 124A likewise translate relative to the housing.

The base 686 can include throughbores or tracks therein to guide sliding of the fibers 122A and the inflation tube 124A relative to the housing 604. The base 686 can be fixed to the housing 604, for example via one or more protrusions that engage corresponding slots formed in the housing. The base 686 can be secured to the housing 604 using an adhesive. The base 686 can be non-movably coupled to the housing 604, such that the base does not move relative to the housing when the slider 688, the fibers 122A, and the inflation tube 124A slide relative to the housing.

The bias element or spring 690 can be positioned between the slider 688 and the base 686. As shown, a first end of the spring 690 can be received within an indentation or pocket formed in the distal surface of the base 686 and a second, opposite end of the spring can be received within an indentation or pocket formed in the proximal surface of the slider 688. The spring 690 can be configured to bias the slider 688 away from the base 686. While a coil spring 690 is shown, it will be appreciated that any of a variety of elements for biasing the slider 688 away from the base 686 can be used instead or in addition, such as leaf springs, wave springs, and the like.

The second connector assembly 602B can include a connector body 606B, a key plate 608B, an internal overmold 610B, a gasket 612B, and an external overmold 614B. The second connector assembly 602B can be substantially the same as the second connector assembly 202B described above.

The connector housing 604 can include a proximal opening 654 in which the slider 688 and base 686 are disposed and a distal opening 656 for receiving the second connector assembly 602B. The connector housing 604 can include any of the features of the connector housing 204 described above. For example, the connector housing 604 can be mounted in the chassis wall of the controller 106.

As shown in FIGS. 35C-35D, the first mating interface 624A of the slider 688 and the second mating interface 624B of the second connector body 606B can be placed in apposition such that fibers 122A extending through the slider are placed in optical communication with fibers 122B extending through the second connector body, and such that a fluid lumen 124A extending through the slider is placed in fluid communication with a fluid lumen 124B extending through the second connector body. The first mating interface 624A can be maintained in alignment with the second mating interface 624B by the connector housing 604.

As the second connector body 606B is advanced into the connector housing 604, it can contact the slider 688 and urge the slider proximally relative to the housing, thereby compressing the spring 690 against the base 686. Accordingly, when the second connector assembly 602B is seated within the housing 604, the slider 688 and the fibers 122A and fluid lumen 124A attached thereto are urged firmly into contact with the second connector assembly by the spring 690. This can help ensure that a fluid-tight seal is formed at the mating between the first and second fluid lumens 124A, 124B and that a solid optical coupling is formed at the mating between the first and second fiber groups 122A, 122B. The spring-biased slider 688 can take up any slack in the system that may exist, e.g., due to manufacturing tolerances or variations in connector seating, thereby ensuring a repeatable positive face to face contact/mating of the fibers and fluid-tight connection of the inflation path. The gasket or seal 694 can be compressed against the second connector assembly 602B under the force of the spring 690 to fortify the fluid-tight connection of the inflation lumens 124A, 124B. Movement of the slider 688 relative to the housing 604 as the connector system 600 is connected is further illustrated in FIG. 35E, which shows the system in a partially connected state, and FIG. 35F, which shows the system in a fully connected state.

While the systems and methods disclosed herein are generally described in connection with measuring a human prostate for diagnostic purposes, it will be appreciated that many other applications exist for such systems and methods. For example, the systems and methods disclosed herein can be used to measure any object, including any portion of a human or animal body. In addition, the systems and methods disclosed herein can be used to measure colorectal cancers or lesions that are within a finger's length into the rectum or to check for benign prostatic hyperplasia.

As used herein, the term "fluid" refers to both liquids (e.g., water or saline) and gasses (e.g., air, nitrogen, or carbon dioxide).

Although specific embodiments are described above, it should be understood that numerous changes may be made within the spirit and scope of the concepts described.

The invention claimed is:

1. A measurement device, comprising:
a ring that defines a measurement pattern on a surface thereof;
a finger clip on which the ring is rotatably mounted; and
one or more optical fibers mounted in the finger clip such that the ring rotates with respect to the fibers as the ring rotates relative to the finger clip and such that the fibers are held at a substantially fixed distance from the measurement pattern as the ring rotates relative to the finger clip;
wherein the finger clip comprises a base portion having an axle on which the ring is rotatably mounted, a fiber guide in which the fibers are fixedly mounted, and a locking pin that retains the ring on the axle.

2. The device of claim 1, further comprising an inflatable membrane disposed over the finger clip.

3. The device of claim 2, wherein the inflatable membrane has a textured or knurled outer surface.

4. The device of claim 2, wherein the inflatable membrane includes a constraint member configured to control the direction and/or degree to which the inflatable membrane inflates when an inflation medium is delivered to an interior thereof.

5. The device of claim 4, wherein the constraint member comprises a band that extends along a dorsal surface of the membrane, across a closed distal end of the membrane, and returns along a ventral surface of the membrane.

6. The device of claim 1, further comprising an inflation tube in which the fibers are disposed, the inflation tube being configured to deliver an inflation medium to an interior of an inflatable membrane disposed over the finger clip.

7. The device of claim 1, wherein the measurement pattern is formed on or coupled to a proximal-facing surface of the ring.

8. The device of claim 1, wherein the finger clip comprises a finger clip cap on which the ring is rotatably mounted and a finger clip base in which the fibers are fixedly mounted.

9. The device of claim 1, further comprising a shroud coupled to the finger clip to cover a dorsal portion of the ring.

10. The device of claim 1, further comprising a proximal sleeve configured to form a seal between an inflatable membrane disposed over the finger clip and a finger of a user.

11. The device of claim 1, wherein a surface of the ring that engages a membrane during a measurement is disposed distal to a distal-most extent of a user's finger when the measurement device is worn by the user.

12. The device of claim 1, wherein the ring and the finger clip are disposed in a closed volume defined between a digit extension of a glove and an outer membrane disposed over the digit extension.

13. The device of claim 12, wherein the digit extension is coupled to the glove by first and second rings.

14. The device of claim 13, wherein the membrane is sealed to the first ring, the digit extension is sealed to the first ring, the glove is sealed to the second ring, and the second ring is rotatable with respect to the first ring.

15. The device of claim 1, wherein the one or more optical fibers comprises:
a first transmitting fiber configured to direct light generated by an external light source onto the measurement pattern;
a first receiver fiber configured to direct light reflected by the measurement pattern to a first external optical detector; and
a second receiver fiber configured to direct light reflected by the measurement pattern to a second external optical detector.

16. The device of claim 15, wherein an output window of the first transmitting fiber, an input window of the first receiver fiber, and an input window of the second receiver fiber are disposed adjacent to one another in a delta configuration.

17. A measurement device comprising:
a ring that defines a measurement pattern on a surface thereof;
a finger clip on which the ring is rotatably mounted, wherein a rotation axis of the ring is oriented at an oblique angle with respect to a longitudinal axis of a base portion of the finger clip; and
one or more optical fibers mounted in the finger clip such that the ring rotates with respect to the fibers as the ring rotates relative to the finger clip and such that the fibers are held at a substantially fixed distance from the measurement pattern as the ring rotates relative to the finger clip.

18. The device of claim 17, further comprising an inflatable membrane disposed over the finger clip.

19. The device of claim 18, wherein the inflatable membrane has a textured or knurled outer surface.

20. The device of claim 18, wherein the inflatable membrane includes a constraint member configured to control the direction and/or degree to which the inflatable membrane inflates when an inflation medium is delivered to an interior thereof.

21. The device of claim 20, wherein the constraint member comprises a band that extends along a dorsal surface of the membrane, across a closed distal end of the membrane, and returns along a ventral surface of the membrane.

22. The device of claim 17, further comprising an inflation tube in which the fibers are disposed, the inflation tube being configured to deliver an inflation medium to an interior of an inflatable membrane disposed over the finger clip.

23. The device of claim 17, wherein the measurement pattern is formed on or coupled to a proximal-facing surface of the ring.

24. The device of claim 17, wherein the finger clip comprises a finger clip cap on which the ring is rotatably mounted and a finger clip base in which the fibers are fixedly mounted.

25. The device of claim 17, further comprising a shroud coupled to the finger clip to cover a dorsal portion of the ring.

26. The device of claim 17, further comprising a proximal sleeve configured to form a seal between an inflatable membrane disposed over the finger clip and a finger of a user.

27. The device of claim 17, wherein the one or more optical fibers comprises:
a first transmitting fiber configured to direct light generated by an external light source onto the measurement pattern;
a first receiver fiber configured to direct light reflected by the measurement pattern to a first external optical detector; and a second receiver fiber configured to direct light reflected by the measurement pattern to a second external optical detector.

28. The device of claim 27, wherein an output window of the first transmitting fiber, an input window of the first receiver fiber, and an input window of the second receiver fiber are disposed adjacent to one another in a delta configuration.

29. A measurement device comprising:
   a ring that defines a measurement pattern on a surface thereof;
   a finger clip on which the ring is rotatably mounted, wherein a rotation axis of the ring is oriented at an oblique angle with respect to a longitudinal axis of a user's finger when the user's finger is disposed in the finger clip; and
   one or more optical fibers mounted in the finger clip such that the ring rotates with respect to the fibers as the ring rotates relative to the finger clip and such that the fibers are held at a substantially fixed distance from the measurement pattern as the ring rotates relative to the finger clip.

30. The device of claim 29, wherein the oblique angle is between about 40 degrees and about 50 degrees.

* * * * *